US010011868B2

(12) United States Patent
Liu et al.

(10) Patent No.: US 10,011,868 B2
(45) Date of Patent: Jul. 3, 2018

(54) REACTIVITY-DEPENDENT AND INTERACTION-DEPENDENT PCR

(71) Applicant: President and Fellows of Harvard College, Cambridge, MA (US)

(72) Inventors: David R. Liu, Lexington, MA (US); David Gorin, Cambridge, MA (US); Adam Kamlet, Somerville, MA (US); Lynn Marie McGregor, Cambridge, MA (US); Christoph Erich Dumelin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 265 days.

(21) Appl. No.: 14/931,782

(22) Filed: Nov. 3, 2015

(65) Prior Publication Data

US 2016/0186238 A1 Jun. 30, 2016

Related U.S. Application Data

(62) Division of application No. 13/505,872, filed as application No. PCT/US2010/002732 on Oct. 13, 2010, now Pat. No. 9,175,340.

(60) Provisional application No. 61/257,983, filed on Nov. 4, 2009.

(51) Int. Cl.

*C12Q 1/686* (2018.01)
*C12N 15/10* (2006.01)
*C12Q 1/6853* (2018.01)

(52) U.S. Cl.

CPC ......... *C12Q 1/686* (2013.01); *C12N 15/1075* (2013.01); *C12Q 1/6853* (2013.01)

(58) Field of Classification Search

CPC ............ C12Q 1/6853; C12Q 2525/301; C12Q 2563/131; C12Q 2563/179; C12Q 1/686; C12N 15/1075

USPC ........................................................ 435/91.2

See application file for complete search history.

(56) References Cited

U.S. PATENT DOCUMENTS

| | | | |
|---|---|---|---|
| 9,175,340 | B2 | 11/2015 | Liu et al. |
| 2009/0053710 | A1 | 2/2009 | Fujihara et al. |
| 2010/0267585 | A1 | 10/2010 | Terbrueggen |
| 2011/0039735 | A1 | 2/2011 | Yamada et al. |
| 2011/0183331 | A1 | 7/2011 | Doi et al. |
| 2016/0083786 | A1 | 3/2016 | Liu et al. |

FOREIGN PATENT DOCUMENTS

| | | | |
|---|---|---|---|
| WO | WO 2011/056185 | A2 | 5/2011 |
| WO | WO 2014/176355 | A1 | 10/2014 |

OTHER PUBLICATIONS

Brindley., https://www.chemistryworld.com/news/chemical-speed-dating-even-faster/3000856.article, publisehd Jun. 18, 2009.*

Invitation to Pay Additional Fees for PCT/US2010/002732, dated Mar. 1, 2011.

International Search Report and Written Opinion for PCT/US2010/002732, dated May 9, 2011.

International Preliminary Report on Patentability for PCT/US2010/002732, dated May 18, 2012.

International Search Report and Written Opinion for PCT/US2014/035177, dated Aug. 18, 2014.

International Preliminary Report on Patentability for PCT/US2014/035177, dated Nov. 5, 2015.

Agrawal et al., A pocket-sized convective PCR thermocycler. Angew Chem Int Ed Engl. 2007;46(23):4316-9.

Angenendt et al., Generation of high density protein microarrays by cell-free in situ expression of unpurified PCR products. Mol Cell Proteomics. Sep. 2006;5(9):1658-66. Epub Jul. 5, 2006.

Baker et al., An electronic, aptamer-based small-molecule sensor for the rapid, label-free detection of cocaine in adulterated samples and biological fluids. J Am Chem Soc. Mar. 15, 2006;128(10):3138-9.

Bartel et al., Isolation of new ribozymes from a large pool of random sequences. Science. Sep. 10, 1993;261(5127):1411-8.

Bowley et al., Libraries against libraries for combinatorial selection of replicating antigen-antibody pairs. Proc Natl Acad Sci U S A. Feb. 3, 2009;106(5):1380-5. Epub Jan. 12, 2009.

Breaker et al., A DNA enzyme that cleaves RNA. Chem Biol. Dec. 1994;1(4):223-9.

Chandra et al., DNA and RNA can be equally efficient catalysts for carbon-carbon bond formation. J Am Chem Soc. Mar. 12, 2008;130(10):2936-7. Epub Feb. 14, 2008.

Clark et al., Design, synthesis and selection of DNA-encoded small-molecule libraries. Nat Chem Biol. Sep. 2009;5(9):647-54. Epub Aug. 2, 2009.

Doyon et al., Highly sensitive in vitro selections for DNA-linked synthetic small molecules with protein binding affinity and specificity. J Am Chem Soc. Oct. 15, 2003;125(41):12372-3.

Dumelin et al., Selection of streptavidin binders from a DNA-encoded chemical library. Bioconjug Chem. Mar.-Apr. 2006;17(2):366-70.

(Continued)

*Primary Examiner* — Cynthia B Wilder

(74) *Attorney, Agent, or Firm* — Wolf, Greenfield & Sacks, P.C.

(57) ABSTRACT

Methods, reagents, compositions, and kits for reactivity-dependent polymerase chain reaction (RD-PCR) and interaction-dependent polymerase chain reaction (ID-PCR) are provided herein. RD-PCR is a technique useful for determining whether a reactive moiety can form a covalent bond to a target reactive moiety, for example, in screening a library of candidate reactive moieties for reactivity with a target reactive moiety, and in identifying an enzyme substrate, for example, in protease substrate profiling. ID-PCR is a technique useful for determining whether a ligand can non-covalently bind to a target molecule, for example, in screening a library of candidate ligands for non-covalent interaction with a target molecule. RD-PCR and ID-PCR are also useful in detecting the presence of an analyte or an environmental condition.

20 Claims, 27 Drawing Sheets

(56) References Cited

OTHER PUBLICATIONS

Ellington et al., In vitro selection of RNA molecules that bind specific ligands. Nature. Aug. 30, 1990;346(6287):818-22.
Evans et al., Integrated, nontargeted ultrahigh performance liquid chromatography/electrospray ionization tandem mass spectrometry platform for the identification and relative quantification of the small-molecule complement of biological systems. Anal Chem. Aug. 15, 2009;81(16):6656-67.
Fredriksson et al., Protein detection using proximity-dependent DNA ligation assays. Nat Biotechnol. May 2002;20(5):473-7.
Gartner et al., The generality of DNA-templated synthesis as a basis for evolving non-natural small molecules. J Am Chem Soc. Jul. 18, 2001;123(28):6961-3.
Gartner et al., DNA-templated organic synthesis and selection of a library of macrocycles. Science. Sep. 10, 2004;305(5690):1601-5. Epub Aug. 19, 2004.
Gartner et al., Expanding the reaction scope of DNA-templated synthesis. Angew Chem Int Ed Engl. May 17, 2002;41(10):1796-800.
Gevaert et al., Exploring proteomes and analyzing protein processing by mass spectrometric identification of sorted N-terminal peptides. Nat Biotechnol. May 2003;21(5):566-9. Epub Mar. 31, 2003.
Gopinath, Methods developed for SELEX. Anal Bioanal Chem. Jan. 2007; 387(1):171-82. Epub Oct. 28, 2006. Review.
Gorin et al., Reactivity-dependent PCR: direct, solution-phase in vitro selection for bond formation. J Am Chem Soc. Jul. 8, 2009;131(26):9189-91.
Gorin et al., Reactivity-dependent PCR: direct, solution-phase in vitro selection for bond formation. J Am Chem Soc. Supporting Information: S1-S13.
Gorska et al., DNA-templated homo- and heterodimerization of peptide nucleic acid encoded oligosaccharides that mimick the carbohydrate epitope of HIV. Angew Chem Int Ed Engl. 2009;48(41):7695-700.
Green, Avidin and streptavidin. Methods in Enzymol. 1990;184:51-67.
Gustafsdottir et al., Use of proximity ligation to screen for inhibitors of interactions between vascular endothelial growth factor A and its receptors. Clin Chem. Jul. 2008;54(7):1218-25.
Halpin et al., DNA display II. Genetic manipulation of combinatorial chemistry libraries for small-molecule evolution. Biol. 2004; 2:1022-30.
Hammond et al., Profiling cellular protein complexes by proximity ligation with dual tag microarray readout. PLoS One. 2012;7(7):e40405.
Hansen et al., A yoctoliter-scale DNA reactor for small-molecule evolution. J Am Chem Soc. Jan. 28, 2009;131(3):1322-7.
Haruki et al., Exploiting ligand-protein conjugates to monitor ligand-receptor interactions. PLoS One. 2012;7(5):e37598.
Heck, Palladium-catalyzed vinylation of organic halides. Org. React. 1928;27:345-90.
Hill et al., Nonenzymatic detection of bacterial genomic DNA using the bio bar code assay. Anal Chem. Dec. 1, 2007;79(23):9218-23. Epub Oct. 10, 2007.
Hill et al., The bio-barcode assay for the detection of protein and nucleic acid targets using DTT-induced ligand exchange. Nat Protoc.2006;1(1):324-36.
Himo et al., Copper(I)-catalyzed synthesis of azoles. DFT study predicts unprecedented reactivity and intermediates. J Am Chem Soc. Jan. 12, 2005;127(1):210-6.
Hinner et al., How to obtain labeled proteins and what to do with them. Curr Opin Biotechnol. Dec. 2010;21(6):766-76.
Höbartner et al., Site-selective depurination by a periodate-dependent deoxyribozyme. Chem Commun (Camb). Jun. 14, 2007;(22):2255-7.Epub May 10, 2007.
Hofstadler et al., Analysis of noncovalent complexes of DNA and RNA by mass spectrometry. Chem Rev. Feb. 2001;101(2):377-90. Review.
Inglese et al., High-throughput screening assays for the identification of chemical probes. Nat Chem Biol. Aug. 2007;3(8):466-79. Review.
Jain et al., Identification of two hydrophobic patches in the active-site cavity of human carbonic anhydrase II by solution-phase and solid-state studies and their use in the development of tight-binding inhibitors. J Med Chem. Jun. 24, 1994;37(13):2100-5.
Jeffreys et al., Repeat unit sequence variation in minisatellites: a novel source of DNA polymorphism for studying variation and mutation by single molecule analysis. Cell. Feb. 9, 1990;60(3):473-85.
Johnston et al., RNA-catalyzed RNA polymerization: accurate and general RNA-templated primer extension. Science. May 18, 2001;292(5520):1319-25.
Joshi et al., A simple and sensitive color test for the detection of human chorionic gonadotropin. Obstet Gynecol. Feb. 1981;57(2):252-4.
Joyce, Directed evolution of nucleic acid enzymes. Annu Rev Biochem. 2004;73:791-836. Review.
Kanan et al., Reaction discovery enabled by DNA-templated synthesis and in vitro selection. Nature. Sep. 30, 2004;431(7008):545-9.
Kleiner et al., In vitro selection of a DNA-templated small-molecule library reveals a class of macrocyclic kinase inhibitors. J Am Chem Soc. Aug. 25, 2010;132(33):11779-91.
Kubista et al., The real-time polymerase chain reaction. Mol Aspects Med. Apr.-Jun. 2006;27(2-3):95-125. Epub Feb. 3, 2006. Review.
Kunishima et al., Synthesis and characterization of 4-(4,6-Dimethoxy-1,3,5-triazin-2-yl)-4methylmorpholinium chloride. Tetrahedron Lett. 1999;40:5327-30.
Li et al., DNA-templated organic synthesis: nature's strategy for controlling chemical reactivity applied to synthetic molecules. Angew Chem Int Ed Engl. Sep. 20, 2004;43(37):4848-70. Review.
Li et al., Translation of DNA into synthetic N-acyloxazolidines. J Am Chem Soc. Apr. 28, 2004;126(16):5090-2.
Lundberg et al., Homogeneous antibody-based proximity extension assays provide sensitive and specific detection of low-abundant proteins in human blood. Nucleic Acids Res. Aug. 2011;39(15):e102.
Mahrus et al., Global sequencing of proteolytic cleavage sites in apoptosis by specific labeling of protein N termini. Cell. Sep. 5, 2008;134(5):866-76. Epub Aug. 21, 2008.
Makrigiorgos, PCR-Based detection of minority point mutations. Human Mut. 2004;23(5):406.
Mannocci et al., High-throughput sequencing allows the identification of binding molecules isolated from DNA-encoded chemical libraries. Proc Natl Acad Sci U S A. Nov. 18, 2008;105(46):17670-5. Epub Nov. 10, 2008.
McDonald et al., Positional proteomics: selective recovery and analysis of N-terminal proteolytic peptides. Nat Methods. Dec. 2005;2(12):955-7. Epub Nov. 18, 2005.
McGregor et al., Identification of ligand-target pairs from combined libraries of small molecules and unpurified protein targets in cell lysates. J Am Chem Soc. Feb. 26, 2014;136(8):3264-70. With supporting information.
McGregor et al., Interaction-dependent PCR: identification of ligand-target pairs from libraries of ligands and libraries of targets in a single solution-phase experiment. J Am Chem Soc. Nov. 10, 2010;132(44):15522-4.
Melkko et al., Encoded self-assembling chemical libraries. Nat Biotechnol. May 2004;22(5):568-74. Epub Apr. 18, 2004.
Melkko et al., Isolation of high-affinity trypsin inhibitors from a DNA-encoded chemical library. Angew Chem Int Ed Engl. 2007;46(25):4671-4.
Mincione et al., Carbonic anhydrase inhibitors: 4-sulfamoyl benzenecarboxamides and 4-chloro-3-sulfamoyl-benzenecarboxamides with strong topical antiglaucoma properties. Bioorg Med Chem Lett. Jul. 9, 2001;11(13):1787-91.
Niemeyer, Semisynthetic DNA-protein conjugates for biosensing and nanofabrication. Angew Chem Int Ed Engl. Feb. 8, 2010;49(7):1200-16.

(56) References Cited

OTHER PUBLICATIONS

Ogawa et al., Aptazyme-based riboswitches as label-free and detector-free sensors for cofactors. Bioorg Med Chem Lett. Jun. 1, 2007;17(11):3156-60. Epub Mar. 15, 2007.
Otto et al., Cysteine Proteases and Their Inhibitors. Chem Rev. Feb. 5, 1997;97(1):133-171.
Pocker et al., The catalytic versatility of erythrocyte carbonic anhydrase. 3. Kinetic studies of the enzyme-catalyzed hydrolysis of p-nitrophenyl acetate. Biochemistry. Mar. 1967;6(3):668-78.
Pradeepkumar et al., DNA-catalyzed formation of nucleopeptide linkages. Angew Chem Int Ed Engl. 2008;47(9):1753-7.
Robertson et al., Selection in vitro of an RNA enzyme that specifically cleaves single-stranded DNA. Nature. Mar. 29, 1990;344(6265):467-8.
Rose et al., Sensitivity gains in chemosensing by lasing action in organic polymers. Nature. Apr. 14, 2005;434(7035):876-9.
Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.
Rozenman et al., DNA-templated synthesis in organic solvents. Chembiochem. Feb. 2006;7(2):253-6.
Rozenman et al., Solving chemical problems through the application of evolutionary principles. Curr Opin Chem Biol. Jun. 2007;11(3):259-68. Epub Jun. 4, 2007. Review.
Schwake et al., A carboxy-terminal domain determines the subunit specificity of KCNQ K+ channel assembly. EMBO Rep. Jan. 2003;4(1):76-81.
Seelig et al., A small catalytic RNA motif with Diels-Alderase activity.Chem Biol. Mar. 1999;6(3):167-76.
Shamah et al., Complex target SELEX. Acc Chem Res. Jan. 2008;41(1):130-8. Review.
Sharon et al., Impedimetric or ion-sensitive field-effect transistor (ISFET) aptasensors nanostructures. Electroanal. 2009;21:1291-6.
Sheppard et al., A DNA enzyme with N-glycosylase activity. Proc Natl Acad Sci U S A. Jul. 5, 2000;97(14):7802-7.
Silverman, Catalytic DNA (deoxyribozymes) for synthetic applications-current abilities and future prospects. Chem Commun (Camb). Aug. 14, 2008;(30):3467-85. Epub Jul. 1, 2008. Review.
Söderberg et al., Direct observation of individual endogenous protein complexes in situ by proximity ligation. Nat Methods. Dec. 2006;3(12):995-1000.
Sprinz et al., Self-assembly of bivalent protein-binding agents based on oligonucleotide-linked organic fragments. Bioorg Med Chem Lett. Sep. 1, 2005;15(17):3908-11.
Suebert et al., Isolation and quantification of soluble Alzheimer's beta-peptide from biological fluids. Naure. 1992;359:325-327.
Swensen et al., Continuous, real-time monitoring of cocaine in undiluted blood serum via a microfluidic, electrochemical aptamer-based sensor. J Am Chem Soc. Apr. 1, 2009;131(12):4262-6.
Tarasow et al., RNA-catalysed carbon-carbon bond formation. Nature. Sep. 4, 1997;389(6646):54-7.
Torreggiani et al., The binding of biotin analogues by streptavidin: a Raman spectroscopic study. Biospectroscopy. 1998;4(3):197-208.
Troutt et al., Ligation-anchored PCR: a simple amplification technique with single-sided specificity. Proc Natl Acad Sci U S A. Oct. 15, 1992;89(20):9823-5.
Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008.
Tuerk et al., Systematic evolution of ligands by exponential enrichment: RNA ligands to bacteriophage T4 DNA polymerase. Science. Aug. 3, 1990;249(4968):505-10.
Vignali. Multiplexed particle-based flow cytometric assays. J Immunol Methods. Sep. 21, 2000;243(1-2):243-55. Review.
Vijayendran et al., A quantitative assessment of heterogeneity for surface-immobilized proteins. Anal Chem. Feb. 1, 2001;73(3):471-80.
West et al., Thermodynamic analysis of protein stability and ligand binding using a chemical modification- and mass spectrometry-based strategy. Anal Chem. Jun. 1, 2008;80(11):4175-85. Epub May 6, 2008.
Wilson et al., In vitro selection of functional nucleic acids. Annu Rev Biochem. 1999;68:611-47. Review.
Wlotzka et al., In vivo properties of an anti-GnRH Spiegelmer: an example of an oligonucleotide-based therapeutic substance class. Proc Natl Acad Sci U S A. Jun. 25, 2002;99(13):8898-902. Epub Jun. 17, 2002.
Wochner et al., A DNA aptamer with high affinity and specificity for therapeutic anthracyclines. Anal Biochem. Feb. 1, 2008;373(1):34-42. Epub Sep. 12, 2007.
Wrenn et al., Chemical evolution as a tool for molecular discovery. Annu Rev Biochem. 2007;76:331-49. Review.
Wrenn et al., Synthetic ligands discovered by in vitro selection. J Am Chem Soc. Oct. 31, 2007;129(43):13137-43. Epub Oct. 6, 2007.
Zhu et al., Review article: high-throughput affinity-based technologies for small-molecule drug discovery. J Biomol Screen. Dec. 2009;14(10):1157-64. Epub. Review.
Extended European Search Report for EP 14788205.4, dated Nov. 25, 2016.

* cited by examiner

| architecture | overlap (bp) | threshold cycle ($C_T$) |
|---|---|---|
| 8a | 10 | 16 |
| 8b | 8 | 18 |
| 8c | 6 | 21 |
| 4a | 0 | 34 |
| 4a+5a | 10 | 29 |
| 4a+5b | 8 | 33 |

| architecture | overlap (bp) | threshold cycle ($C_T$) |
|---|---|---|
| S4 | 10 | 17 |
| 9a | 8 | 18 |
| S5 | 6 | 28 |
| 4a | 0 | 32 |
| 4a+S3 | 10 | 26 |
| 4a+10a | 8 | 28 |

| DMTMM | $C_T$ |
|---|---|
| + | 18 |
| - | 29 |
| +[a] | 25 |
| -[a] | 25 |

a) 3'-OH-DNA (4a) in place of 4c.

| DNA-ligand | DNA-target | SA | overlap (nt) | threshold cycle ($C_T$) |
|---|---|---|---|---|
| **2** | **1** | + | 6 | 21 |
| **2a-biotin** | **1** | + | 6 | 21 |
| **2** | **1e-biotin** | + | 6 | 21 |
| **2a-biotin** | **1e-biotin** | + | 6 | 14 |
| **2a-biotin** | **1e-biotin** | - | 6 | 20 |

REACTIVITY-DEPENDENT AND INTERACTION-DEPENDENT PCR

RELATED APPLICATIONS

This application is a divisional of and claims priority under 35 U.S.C. § 120 to U.S. Application, U.S. Ser. No. 13/505,872, filed Jul. 16, 2012, now U.S. Pat. No. 9,175, 340, which is a national stage filing under 35 U.S.C. § 371 of international PCT application, PCT/US2010/002732, filed Oct. 13, 2010, which claims priority under 35 U.S.C. § 119(e) to U.S. provisional patent application, U.S. Ser. No. 61/257,983, filed Nov. 4, 2009, each of which is incorporated herein by reference.

GOVERNMENT SUPPORT

This invention was made with Government support under grant R01GM065865 awarded by the National Institute of General Medical Sciences and grant GM065865 awarded by the National Institutes of Health. The Government has certain rights in this invention.

BACKGROUND OF THE INVENTION

Current approaches for identifying functional nucleic acids and small molecules from libraries of such molecules are generally indirect. They require the synthesis of tagged substrates and typically involve multiple manipulations. Thus, current approaches leave much to be desired for the efficient screening of libraries of rapidly increasing complexity.

In vitro selection is a key component of efforts to discover functional nucleic acids and small molecules from libraries of DNA, RNA, and small molecules.(1) When the desired activity is binding affinity, as is the case for aptamer evolution(2) or for the discovery of DNA-linked small molecules that bind to a particular target,(3) a direct selection is possible; the library is typically incubated with immobilized target molecules, and bound library members are washed and eluted before being subjected to PCR amplification (FIG. 1*a*).

In vitro selections have also been developed to evolve RNA and DNA catalysts(4) and, more recently, to discover new reactions from DNA-encoded libraries of potential substrates.(5) In these selections, library members may undergo bond formation or bond cleavage. Selections for reactivity are significantly more complicated than selections for binding affinity. Typically, libraries are incubated with biotinylated substrates or potential reaction partners. Bond formation results in the attachment of biotin to a library member, which in turn enables its capture by immobilized avidin (FIG. 1*b*).(6) For bond cleavage, an inverse approach is commonly used in which immobilized, biotinylated library members are liberated upon bond scission.(7) While effective, such selections for chemical reactivity are indirect, require the synthesis of biotin-linked substrates, and involve multiple solution-phase and/or solid-phase manipulations. Therefore, better approaches to selection for chemical reactivity are needed to more efficiently screen complex libraries of chemical compounds for the discovery of new chemical reactions and interactions. References (1)-(7) are identified in Example 1.

SUMMARY OF THE INVENTION

In vitro selection of reaction or binding partners is an important way of discovering molecules with desired properties from libraries of candidate molecules, for example, from DNA, RNA, protein, peptide, and small molecule libraries. Such selections have been widely used to evolve RNA and DNA catalysts and, more recently, to discover new reactions from DNA-encoded libraries of potential substrates. Based on the observation that the melting temperature ($T_m$) of a double-stranded nucleic acid is substantially higher when hybridization occurs intramolecularly as opposed to intermolecularly, the present invention provides a system for reactivity-dependent or interaction-dependent polymerase chain reaction, a new in vitro selection technology that more directly links bond formation, bond cleavage, or a molecular interaction with the amplification of a desired sequence. This new system obviates the need for solid-phase capture, washing, and elution steps. This technology can be used to select for bond formation in the context of reaction discovery. It can also be used to identify cleavage sites in the context of protease or nuclease activity profiling. For example, reactivity-dependent PCR (RD-PCR) can be used for the identification of protease substrate amino acid sequences and for the identification of nuclease substrate nucleotide sequences. RD-PCR can also be useful in the evolution of ribozymes and DNAzymes. Further, this technology can be useful in identifying DNA binding site preferences of transcription factors and other DNA-binding proteins, for example, zinc-finger endonucleases. ID-PCR can be used in the identification of ligands that bind therapeutically relevant targets. Accordingly, ID-PCR can be useful in identifying agonists and antagonists of therapeutic targets.

Some aspects of this invention are based on the melting temperature ($T_m$) difference between duplex DNA formed intramolecularly versus intermolecularly. This difference can be exploited to couple covalent bond formation or a non-covalent association with PCR amplification. This invention stems from the discovery that a nucleic acid template can be efficiently amplified in a polymerase chain reaction (PCR) using a primer that is conjugated to the template, for example, a primer that is covalently attached to the template or a primer that is non-covalently associated with the template, under suitable conditions (e.g., temperature, salt concentration), not allowing for annealing and efficient extension of a primer not conjugated to or associated (covalently or non-covalently) with the template.

Some aspects of this invention relate to exploiting this discovery to determine whether two reactive moieties, a candidate reactive moiety and a target reactive moiety, can form a covalent bond under certain test conditions (see FIG. 2). Reactivity-dependent PCR (RD-PCR) features efficient amplification of a PCR product only after a covalent bond is formed between a candidate reactive moiety coupled to a template and a target reactive moiety coupled to a primer. Reactive moieties may include, but are not limited to, such functional groups as amines, thiols, azides, hydroxyls, alkenes, alkynes, alkyl halides, dienes, acyl halides, esters, amides, etc. Some aspects of this invention relate to the application of RD-PCR to in vitro selection and chemical library screening. For example, RD-PCR may be used in the discovery and development of methods combining organic or bond-forming chemistry with PCR methodology. In certain embodiments, this invention relates to methods including coupling a candidate reactive moiety of a primer to a nucleic acid template including a sequence tag identifying its respective candidate reactive moiety. Some aspects of this invention relate to methods of contacting such nucleic acid templates with a target reactive moiety coupled to a primer and a subsequent amplification of only those nucleic acid templates coupled to a primer through a covalent bond formed between the two reactive moieties (see FIG. 2*b*).

In one aspect, this invention provides a method for determining whether a candidate reactive moiety can form a covalent bond with a target reactive moiety. In another aspect, the invention provides a method for screening a library of candidate reactive moieties for their ability to form a covalent bond with a target reactive moiety. In one aspect, the invention provides a method for determining whether a candidate ligand can bind to a target compound (e.g., a small molecule) or biomolecule (e.g., a peptide or nucleic acid), biomolecule derivative, or fragment thereof. In another aspect, the invention provides a method for screening a library of candidate ligands for their ability to bind a target compound or biomolecule, biomolecule derivative, or fragment thereof.

In one aspect, the present invention provides a method for screening a library of candidate structures, for example, polypeptide sequences or nucleotide sequences, to identify a structure, for example, an amino acid sequence or a nucleotide sequence, that is a substrate of an enzyme of interest. Such a method is, for example, particularly useful in determining the target sequence of a protease or a nuclease. Many proteases or nucleases cleave at a specific site within a target peptide or nucleotide sequence, but often a protease or nuclease recognizes a number of more or less similar target sequences. In certain embodiments, this invention provides methods to identify a protease-substrate peptide or a nuclease-substrate nucleotide sequence in a library of candidate substrates. In some embodiments, a library of nucleic acid templates coupled to candidate substrate peptides is provided and contacted with a protease of interest and a primer coupled to a reactive moiety. Cleavage of a candidate substrate peptide by the protease generates a reactive moiety (e.g., an amino group) that can subsequently form a covalent bond with a primer, while uncleaved candidate substrate peptides cannot form such a bond. PCR is then used to selectively amplify those nucleic acid templates coupled to candidate substrate peptides that have been cleaved and, thus, include a target sequence for the respective protease. In some embodiments, the sequence of the substrate peptides is determined by identifying the sequence tag of the amplified nucleic acid templates. Similarly, a library of candidate nucleic acid sequences may be screened in order to identify a target nucleic acid sequence for a given nuclease. In such embodiments, a library of nucleic acid templates coupled to a candidate nucleic acid substrate is provided, contacted with a nuclease of interest and target nucleotide sequences are identified by RD-PCR in analogy to the identification of protease substrate sequences described herein. A consensus target sequence and enzyme preference for variations of such a consensus sequence can be determined if multiple target sequences are discovered. Such protease or nuclease profiling information can be useful, for example, for predicting targets of a specific protease. Accordingly, in one embodiment, the invention provides a method for protease activity profiling, involving identifying a plurality of substrate polypeptides of a protease of interest. Further, other aspects of this invention provide a method for determining a consensus binding sequence of a protease of interest. In one embodiment, the invention provides a method for nuclease activity profiling, involving identifying a plurality of substrate polynucleotide sequences of a nuclease of interest. Further, other aspects of this invention provide a method for determining a consensus binding sequence of a nuclease of interest.

In some embodiments, RD-PCR may be used to identify a functional nucleic acid (e.g., a ribozyme or DNAzyme) that cleaves a given target or catalyzes the formation of a specific reactive moiety or covalent bond. In such embodiments, a library of templates may be provided, which include a candidate functional nucleic acid sequence (e.g., a ribozyme or DNAzyme), a first primer hybridization site, a PCR primer hybridization site, and, optionally, a reactive moiety, and a sequence tag. In some embodiments, a template including a candidate functional nucleic acid coupled to a specific substrate is contacted with a primer coupled to a reactive moiety that can form a covalent attachment to a substrate only after the substrate has been modified by the functional nucleic acid, for example, by hydrolysis, acylation, phosphorylation, dephosphorylation, ligation, or other enzymatic reaction. In some embodiments, the candidate functional nucleic acid is a cis-acting nucleic acid. In some embodiments, a library of templates including candidate functional nucleic acids is screened to identify a functional nucleic acid able to catalyze a specific reaction, for example, cleavage of a nucleic acid target sequence. If a given template includes a functional nucleic acid that can perform the desired function, e.g., cleave a specific target nucleotide sequence or modify a reactive moiety in a way that a covalent bond between the template and the first primer can be formed, then the respective template sequence can be amplified in an RD-PCR reaction. In certain embodiments, a functional nucleic acid is identified by the sequence tag associated with the template. In certain embodiments, a sequence tag may be dispensable if the sequence of the functional nucleic acid can directly be determined from the respective RD-PCR product.

In other aspects of the invention, methods are provided that depend on non-covalent binding or association of a template and a first primer for PCR amplification instead of covalent bond formation between the two. This technology, also referred to as interaction-dependent PCR (ID-PCR), is useful to determine whether a candidate molecule, for example, a peptide or small molecule, can bind to a target molecule, for example, a protein of interest. In certain embodiments, a library of candidate molecules is screened for molecules that can bind non-covalently to a target molecule. In some embodiments, methods are provided to screen a library of candidate ligands against a library of candidate binding molecules, for example, a library of small molecules is screened against a library of polypeptides, to identify pairs of binding partners. In some embodiments, these pairs of binding partners are relevant to a specific biological pathway, and the identified ligands can be used as leads for the development of drugs targeting that biological pathway.

Some aspects of the invention relate to the use of RD-PCR or ID-PCR as an environmental sensor or a chemical sensor. In some embodiments, an RD-PCR reaction strategy or an ID-PCR binding strategy is provided in which the formation of a covalent bond or a non-covalent association depends on the presence or absence of a particular agent or analyte, for example, an oxidant, an enzyme, or an ion. Because of the high sensitivity of PCR, RD-PCR and ID-PCR strategies are particularly useful for the detection of low-abundance analytes.

Some aspects of the invention relate to reagents and kits useful to perform RD-PCR and/or ID-PCR. Reagents useful for performing RD-PCR and/or ID-PCR include, for example, reactive moieties, ligands or target molecules, reagents necessary to couple such moieties, ligands, or target molecules to a nucleic acid, nucleic acids, nucleic acids coupled to target reactive moieties, nucleic acids coupled to candidate reactive moieties, nucleic acids including a primer hybridization site and/or a sequence complementary to a primer hybridization site, and/or PCR reagents (e.g., buffer, polymerase, and/or nucleotides). Such reagents or a subset thereof may be conveniently packaged in a kit for use by a researcher. The kit may include instructions for using the components in RD-PCR and/or ID-PCR.

DEFINITIONS

Figure 1:
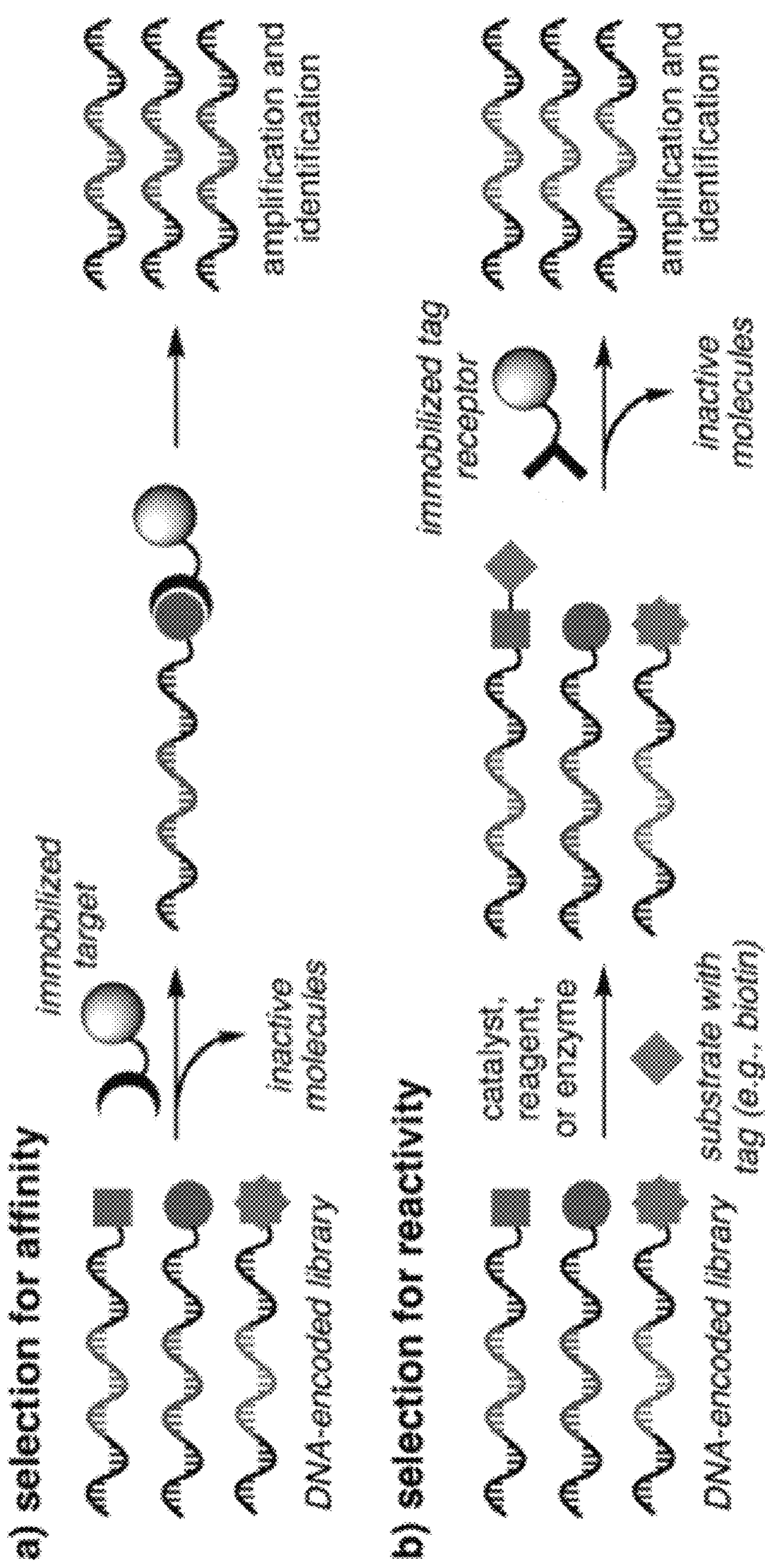
FIG. 1. Traditional approaches to in vitro selection.

As used herein and in the claims, the singular forms "a," "an," and "the" include the plural reference unless the context clearly indicates otherwise. Thus, for example, a reference to "an agent" includes a plurality of such agents.

As used herein, the term "amplicon" refers to a nucleic acid molecule that is amplified in a polymerase chain reaction. In RD-PCR and ID-PCR reactions, an amplicon is typically the nucleic acid template or a portion thereof. In library screening RD-PCR or ID-PCR reactions, the amplicon typically includes the sequence tag of the nucleic acid template.

As used herein, the term "analyte," interchangeably used with the term "environmental parameter," refers to a component of a sample (e.g., an environmental or biological sample), the presence or absence of which can be determined by an RD-PCR or ID-PCR assay. In some RD-PCR embodiments, the analyte is a cofactor to a reaction, for example a molecule or condition without which a covalent bond between two reactive moieties is not efficiently formed. In some ID-PCR embodiments, the analyte is a cofactor to an interaction, for example a molecule or condition without which a non-covalent interaction between a ligand and a binding molecule is not efficiently formed. Non-limiting examples for analytes are a cofactor to an enzymatic reaction, an enzyme, a binding molecule, a catalyst of a chemical reaction, and oxidizing conditions.

As used herein, the term "catalyst" refers to a chemical substance able to increase or decrease the rate of a chemical reaction. A catalyst may be heterogeneous (existing in a different phase than the substrate) or homogeneous (existing in the same phase as the substrate). For example, if the reaction is, for example, a covalent bond-forming reaction between two reactive moieties that takes place in an aqueous solution, a catalyst may be, for example, in solution, a solid, or in colloidal form. A catalyst may be an inorganic catalyst, for example, an ion or a metal surface; an organometallic catalyst; or an organic catalyst. A catalyst may include, for example, an ion, for example, a Cu, Mg, Zn, Pb, Pd, Pt, Ca, or Fe ion; a protein, for example, an enzyme; a nucleic acid, for example, a ribozyme or DNAzyme; or a small molecule. The choice of a suitable catalyst will depend, of course, on the specific chemical reaction and the reactants. Catalysts for many different chemical reactions are well known in the art.

As used herein, the term "contacting" refers to bringing a first molecule, for example, a nucleic acid molecule (e.g., a nucleic acid template including a reactive moiety), and a second molecule, for example, a second nucleic acid molecule (e.g. a primer), optionally including a second reactive moiety, together in a manner that the molecules can bind, hybridize, and/or react. Contacting may be accomplished in a cell-free system, for example, by adding a second molecule to a solution including a first molecule under suitable conditions. Conditions suitable for nucleic acid hybridization and various chemical reactions are well known in the art.

As used herein, the term "covalent bond" refers to a form of chemical bonding that is characterized by the sharing of one or more pairs of electrons between atoms. Reactions forming a covalent bond between two reactive moieties are well known in the art, and include, for example, acylation reactions, addition reactions, nucleophilic substitution reactions, cycloaddition reactions, carbonyl chemistry reactions, "non aldol"-type carbonyl chemistry reactions, carbon-carbon bond forming reactions, and addition reactions to carbon-carbon double or triple bonds. A covalent bond formed between two reactive moieties may, for example, be an amide bond, an acyl bond, a disulfide bond, an alkyl bond, an ether bond, or an ester bond. A covalent bond formed between two reactive moieties may be, for example, a carbon-carbon bond, a carbon-oxygen bond, a carbon-nitrogen bond, a carbon-sulfur bond, a sulfur-sulfur bond, a carbon-phosphorus bond, a phosphorus-oxygen bond, or a phosphorus-nitrogen bond.

As used herein the term "enzyme" refers to a molecule, for example, a peptide, a protein, or a nucleic acid (for example, a ribozyme or DNAzyme) that catalyzes a chemical reaction. An enzyme may be a biomolecule (a molecule made by a living organism), a derivative of a biomolecule (e.g., a mutated biomolecule, a fragment of a biomolecule, and/or a fusion product of a biomolecule, or fragment thereof, with a second molecule), or an artificially made molecule (e.g., a synthetic protein or nucleic acid). An enzyme may be an oxidoreductase, transferase, polymerase, hydrolase lyase, synthase, isomerase, or ligase. Accordingly, a protease and a nuclease are non-limiting examples of enzymes. In certain embodiments, the enzyme is a protein. In certain embodiments, the enzyme is a nucleic acid. In certain embodiments, the enzyme is RNA. In certain embodiments, the enzyme is DNA.

As used herein, the term "enzyme substrate" is a molecule upon which an enzyme acts. An enzyme substrate is bound by an enzyme and transformed into one or more products in a chemical reaction catalyzed by the enzyme. The reaction product or products are usually released from the enzyme. For example, a protease catalyzes the hydrolysis of an amide bond in a protease substrate peptide or protein. The substrate peptide of a protease is generally bound specifically, meaning that only a peptide of a certain amino acid sequence or with a sequence similar to a consensus sequence is bound by the protease and cleaved into two or more fragments in a hydrolysis reaction.

As used herein, the term "functional nucleic acid" refers to a nucleic acid with enzymatic activity, binding activity, or biological activity. Ribozymes and DNAzymes are non-limiting examples for functional nucleic acids.

As used herein, the term "interaction-dependent polymerase chain reaction" (ID-PCR) refers to a PCR assay in which amplification of a nucleic acid template depends upon the nucleic acid template having a non-covalent association with a PCR primer. The non-covalent association is preferably a high-affinity association, for example, characterized by a $K_D$ of $10^{-6}$ or less. The non-covalent association may be formed between a ligand attached to the nucleic acid template and a binding molecule attached to the primer.

The term "ligand" as used herein, refers to a binding molecule that binds non-covalently to a second binding molecule with high affinity. In some embodiments, a high-affinity bond is characterized by a $K_D<10^{-6}$, a $K_D<10^{-7}$, a $K_D<10^{-8}$, a $K_D<10^{-9}$, a $K_D<10^{-10}$, a $K_D<10^{-11}$, or a $K_D<10^{-12}$. In some embodiments, the ligand is a small molecule. In some embodiments, the ligand is a peptide or protein. In some embodiments, the ligand is a nucleic acid.

As used herein, the term "library of nucleic acid templates" refers to a plurality of nucleic acid templates. In some embodiments, each nucleic acids template of a library of nucleic acid templates is bound to one of various reactive moieties. In some embodiments, a library of nucleic acid templates includes nucleic acid templates bound to the same type of reactive moiety, for example, a library of polypeptide-associated nucleic acid templates may include only nucleic acid templates bound to polypeptides. In some embodiments, each nucleic acid template is bound to a specific reactive moiety, wherein the specific reactive moiety a nucleic acid template is bound to can be identified by the nucleic acid template's sequence tag. For example, a specific sequence tag may identify a peptide-associated nucleic acid template to be bound to the peptide Ala-Pro-Gly-Phe-Ala (SEQ ID NO: 1), whereas a different nucleic acid template of the same library with a different sequence tag is bound to a different peptide.

The term "melting temperature" ($T_m$) is an art-recognized term and refers to the temperature at which hybridization of two nucleotide strands is destabilized so that the two nucleotide strands separate (or dissociate). In PCR, the melting temperature is the temperature at which a primer hybridized to a template dissociates from the template.

As used herein, the term "non-covalent bond", interchangeably used with the term "non-covalent interaction" herein, refers to a type of interaction between two molecules that does not involve the sharing of electrons between the molecules, but involves variations of electromagnetic, electrostatic, or hydrophobic interactions.

As used herein, the term "nucleic acid," interchangeably used with the terms "nucleic acid template," "nucleic acid molecule," "polynucleotide," and "oligonucleotide," refers to a polymer of nucleotides. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), and/or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., *Proc. Natl. Acad. Sci. USA,* 2002, 99(13): 8898, the entire contents of which are incorporated herein by reference. A nucleic acid may further include a non-nucleic acid moiety or molecule, for example, a reactive moiety or a binding molecule, such as a ligand.

As used herein, the term "nucleic acid linker" refers to a nucleic acid molecule including a primer hybridization site. A nucleic acid linker may be single-stranded or double-stranded. A double-stranded nucleic acid linker may include a nucleic acid overhang compatible with a specific restriction site in a ligation reaction. Alternatively, a double-stranded nucleic acid linker may be blunt-ended. A nucleic acid linker may be ligated to a nucleic acid molecule in order to add a primer hybridization sites or a restriction site.

The term "polymerase chain reaction" (PCR) is an art recognized term and refers to a method of amplifying a nucleic acid molecule. PCR uses thermal cycling, consisting of cycles of repeated heating and cooling of a PCR sample including the nucleic acid molecule to be amplified. A typical PCR cycle includes a denaturation (or melting) step, an annealing step, and an elongation (or extension) step. A typical PCR includes between 12 and 40 cycles. A PCR may further include an initialization step, for example, if each activation of a hot start polymerase is performed, a hold step, a final extension or hold step, and a final cooling step. PCR reagents include a buffer, for example, a buffer including $Mg^{2+}$ ions, one or more primers, nucleotides, and a thermophilic polymerase, for example, Taq, Pfu, Pwo, Tfl, rTth, Tli, Tma, Bst, 9° $N_m$, Vent, or Phusion polymerase. A PCR product is a nucleic acid generated as a result of a PCR. PCR protocols are well known in the art, for example, as described in Chapter 8 ("In vitro amplification of DNA by the polymerase chain reaction") of Sambrook et al., *Molecular Cloning: A laboratory Manual, Volumes* 1-3, *Cold Spring Harbor Laboratory Press,* 2001. Reagents and reagent kits for PCR are available from numerous commercial suppliers.

The term "quantitative PCR" (qPCR) refers to a method used to measure the quantity of a PCR product. If the quantity of a PCR product is measured in real time, the method is referred to as "quantitative, real-time PCR".

A "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

As used herein, the term "primer" refers to a nucleic acid molecule that can hybridize to a primer hybridization site of a nucleic acid template via base pairing and that can be elongated by a polymerase, for example, Taq, Pfu, Pwo, Tfl, rTth, Tli, Tma, Bst, 9° $N_m$, Vent, or Phusion polymerase during a PCR. A primer, accordingly, includes a free 3'-OH group or other group amenable to the addition of nucleotide monomers by a polymerase. In some embodiments, only a 3' portion of the primer hybridizes to the primer hybridization site. In other embodiments, the whole primer hybridizes to the primer hybridization site. A primer includes a nucleotide sequence complementary to that of the primer hybridization site it hybridizes to. It should be noted, that primer hybridization may tolerate nucleotide-nucleotide mismatches, and, therefore, "complementary" does not require complete complementarity, but only a degree of complementarity sufficient for hybridization. Typically, a primer includes between 18 to 35 nucleotides. However, a primer may be longer or shorter than that, for example, ranging in length from 5-100 nucleotides. In a PCR, a primer hybridizes with a primer hybridization site of a nucleic acid template during the annealing step, is elongated by nucleotide addition in the elongation step, and the hybridization of elongated primer and template are broken during the denaturing step. If a primer is covalently bound to the nucleic acid molecule including the primer hybridization site, the sequence hybridizing with the nucleic acid template may be as short as 5-10 nucleotides, for example, the hybridizing sequence of the primer may be 5, 6, 7, 8, 9, or 10 nucleotides long.

As used herein, the term "primer extension," interchangeably used with the term "primer elongation", refers to the extension of a primer that hybridizes to a nucleic acid template by the addition of nucleotides complementary to the nucleic acid sequence of the template. In a PCR, this primer extension is usually performed by a thermophilic polymerase, for example, Taq, Pfu, Pwo, Tfl, rTth, Tli, Tma, Bst, 9° $N_m$, Vent, or Phusion polymerase.

As used herein, the term "primer hybridization site" refers to a nucleotide sequence that a primer can hybridize to. A primer hybridization sites may be part of a nucleic acid template. The primer hybridization site may be 100% homologous to the primer sequence, or may be less than 100% homologous (e.g., 99.9%, 99%, 98%, 97%, 96%, 95%, 90%, 85% homologous). The length and sequence of a primer hybridization site is dependent on the specific application. Length and nucleotide sequence can impact PCR parameters such as annealing temperature and cycle length. Usually, a primer hybridization site is between 10-40 bases long. In some embodiments, a primer hybridization site may be shorter than that, depending on primer sequence and intended hybridization parameters. Methods to design primers for annealing and extension in view of hybridization and extension parameters and methods of adapting hybridization and extension conditions in view of specific primer length and/or sequence are well known in the art.

As used herein, the term "protease", refers to any enzyme that catalyzes a proteolysis reaction, for example, hydrolysis of a peptide bond. Protease substrates are typically polypeptides or proteins. A protease may specifically bind only a polypeptide or protein including a specific amino acid sequence, the binding motif, or, alternatively, a protease may bind a plurality of polypeptides or proteins including different binding motif amino acid sequences that are similar to a consensus sequence of the binding motif. A protease binding motif consensus sequence can be determined by methods known to those of skill in the art, once a plurality of binding motifs has been identified. A binding motif consensus sequence determination may also include a quantitative analysis of binding protease binding motif preferences among a plurality of binding motifs, for example, by measuring reaction rates for different binding motifs.

The term "protease substrate profile" refers to a list of identified substrate binding motifs of a specific protease. Such a list may include weighted binding information for each identified protease binding motif and/or a binding motif consensus sequence.

The term "protein," used interchangeably with the term "polypeptide" herein, refers to a molecule including a polymer of amino acid residues linked together by peptide bonds. The term, as used herein, refers to proteins, polypeptides, and peptide of any size, structure, or function. Typically, a protein or polypeptide will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination thereof.

As used herein, the term "reactive moiety" refers to a molecular entity or functional group able to form a covalent bond with another reactive moiety. Accordingly, a reactive moiety may include a reactive functional group, for example, an alkenyl, alkynyl, phenyl, benzyl, halo, hydroxyl, thiol, carbonyl, aldehyde, carbonate ester, carboxylate, carboxyl, ether, ester, carboxyamide, amine, ketimine, aldimine, imide, azido, diimide, cyanate, isocyanide, isocyanate, isothiocyanate, nitrile, sulfide, or disulfide group. A reactive moiety may be part of a compound. The term "compound" refers to any molecule that is to be tested, for example, for the ability of a reactive moiety of a compound to form a covalent bond with a second reactive moiety. A reactive moiety or a compound containing such a moiety can be randomly selected or rationally selected or designed.

As used herein, the term "reactivity-dependent polymerase chain reaction" (RD-PCR) refers to a PCR assay in which amplification of a nucleic acid template depends upon the nucleic acid template forming a covalent bond with a primer. The covalent bond may be formed between a reactive moiety of the nucleic acid template and a reactive moiety of the primer.

As used herein, the term "screening of a reactive moiety library" refers to an experiment to identify a reactive moiety with a specific characteristic in a reactive moiety library. Depending on the screening assay to be performed, as well as the format of the library, the experimental design of a library screen may vary. For example, a reactive moiety library screen may include contacting a plurality of candidate reactive moieties in a library in parallel, for example, in a single solution, with a screening reagent, for example, a target reactive moiety. As another example, a reactive moiety library screen may include contacting the plurality of reactive moieties of the library individually, for example, contacting a first candidate reactive moiety in a first solution, a second candidate reactive moiety in a second solution, and so forth, for example, in a microtiter-plate format, wherein a well is used to contact an individual candidate reactive moiety.

As used herein, the term "sequence tag" refers to a nucleotide sequence used to identify a candidate reactive moiety bound to a nucleic acid molecule or nucleic acid template. For example, in a library screening experiment, a nucleic acid template with a specific first sequence tag may include a specific candidate reactive moiety, while a nucleic acid template with a different sequence tag may include a different candidate reactive moiety. This way, a specific reactive moiety that forms a covalent bond with a target reactive moiety, for example, in a library screen, in which the nucleic acid templates of the library are contacted in parallel, can be identified by sequencing the sequence tag of an RD-PCR product obtained in the screen. Depending on the complexity of the library to be screened, the length of the sequence tag may vary. A single nucleotide in a DNA sequence tag including naturally occurring nucleotides can represent one out of four bases A, C, G and T. Thus, a sequence tag will allow for the identification of $4^n$ nucleic acid templates with n being the number of nucleotides of the sequence tag. For example, a sequence tag including 4 nucleotides could theoretically identify 256 different nucleic acid templates/reactive moieties, a sequence tag including 10 nucleotides could theoretically identify 1,048,576 nucleic acid templates/reactive moieties. In practice, some theoretically possible sequence tags, for example, an all-G tag, may interfere with RD-PCR template amplification. Sequence tags with very high (>80%) or very low (<20%) GC content may cause problems in nucleic acid amplification during RD-PCR or ID-PCR, as may sequence tags showing self-complementarity or complementarity to any part of the nucleic acid template or other nucleic acids used in the RD-PCR or ID-PCR reaction. It is well known to those in the art how to design sequence tags and how to avoid high and low GC-content in designing nucleic acid components, for example, primers and templates, for PCR. As a result, the practical amount of useful tags for a given sequence tag length is lower than the theoretical number of possible sequence tags. Sequence tag length may be determined, for example, by the number of reactive moieties to be tagged and/or the sequencing technology to be used in RD-PCR product sequencing. A library of nucleic acid molecules including sequence tags may include sequence tags of different length, thus increasing the number of usable sequence tags at any given maximum sequence tag length. The term "identifying a sequence tag" refers to determining the nucleotide sequence of a sequence tag.

As used herein, the term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and/or other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. Preferred small molecules are biologically active in that they produce a biological effect, for example, a kinase inhibitor produces inhibition of a kinase, in animals, preferably mammals, more preferably humans. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. § § 330.5, 331 through 361, and 440 through 460, incorporated herein by reference; drugs for veterinary use are listed by the FDA under 21 C.F.R. § § 500 through 589, incorporated herein by reference. All listed drugs are considered acceptable for use in accordance with the present invention.

As used herein, the term "suitable conditions," interchangeably used with the term "conditions suitable," refers to conditions that are suitable for a specific reaction, interaction, or other event to take place. For example, conditions suitable to form a covalent bond between two reactive moieties may include both reactive moieties, a suitable medium allowing both reactive moieties to interact, for example, an aqueous solution, a reaction cofactor or catalyst, if necessary, a buffering agent, a certain temperature, pH, or osmolarity. The suitable conditions for any given reaction or interaction will, of course, depend on the specific reaction or interaction. Suitable conditions for the reactions or interactions described herein are well known to those in the relevant chemical and molecular biological arts. For example, suitable conditions for nucleic acid hybridization, primer extension, restriction digestion, and linker ligation are described herein and in Sambrook et al., *Molecular Cloning: A Laboratory Manual, Volumes* 1-3, *Cold Spring Harbor Laboratory Press,* 2001, incorporated herein by reference. Further, suitable conditions for various chemical reactions are described herein and, for example, in Smith and March, *March's Advanced Organic Chemistry: Reactions, Mechanisms, and Structure*, Wiley-Interscience, 6$^{th}$ edition, 2007, incorporated herein by reference. Suitable conditions for covalent bond formation, enzymatic catalysis, and PCR are described herein and well known to those of skill in the art. In some embodiments, suitable conditions for hybridization of a nucleic acid template's primer hybridization site and a primer including a complementary nucleic acid sequence and/or primer extension are conditions allowing for efficient primer site hybridization and/or primer extension if the primer is covalently bound to the nucleic acid template, but not allowing for efficient primer site hybridization and/or primer extension if the primer is not covalently bound to the nucleic acid template.

The term "template," as used herein, refers to a nucleic acid molecule including a primer hybridization site. A template may also include (e.g., be coupled to) a candidate reactive moiety and may include a tag, such as a sequence tag, identifying the attached candidate reactive moiety. A template is typically a DNA molecule.

DETAILED DESCRIPTION OF THE INVENTION

Recent advances in genome and proteome research have led to a dramatic increase in the number of targets of interest to the life sciences. The rapid identification of reaction partners and ligands to this expanding number of targets is a major scientific and technological challenge. To this end, a variety of target-oriented high-throughput screening methods have been developed. Two fundamental limitations to target-oriented screening methods are (i) the requirement that each target of interest must successively be assayed against libraries of potential ligands; and (ii) the general reliance on immobilized targets or ligands. The first constraint limits assay throughput significantly when researchers are interested in multiple targets or in ligand specificity. The second limitation adds immobilization, washing, and/or elution steps to the screening process and is a source of artifacts that arise, for example, from matrix binding, multivalent binding, or loss of native target structure. A solution-phase method to simultaneously reveal all reactive pairs or ligand-target binding pairs from a single solution containing libraries of candidate reactive agents or ligands and libraries of targets could in principle overcome both limitations and significantly increase the efficiency and effectiveness of target-oriented screening efforts. This invention provide such systems, for example, RD-PCR and ID-PCR.

Reactivity-dependent PCR (RD-PCR) and interaction-dependent PCR (ID-PCR), in general, exploit the discovery that a primer that is bound to a nucleic acid template can more efficiently hybridize to the template and initiate replication of the template than a non-covalently bound primer. That is, the melting temperature of a double-stranded nucleic acid is substantially higher when hybridization is intramolecular as opposed to intermolecular.

RD-PCR and ID-PCR are systems that are useful in identifying reaction partners or binding partners, respectively, from combined libraries of candidate reactive molecules or binding molecules. Formation of a covalent bond between a DNA template-linked reactive moiety and a primer-linked reactive moiety or of a non-covalent association between a DNA template-linked target and a primer-linked ligand results in the formation of a molecule in which the primer can hybridize with the target intramolecularly, which induces formation of an extendable duplex. If the DNA-template comprises an identifiable tag, extension links codes identifying the reactive moiety or the target molecule into one selectively amplifiable DNA molecule.

Some RD-PCR methods described herein include (a) contacting a template (including a candidate reactive moiety) with a primer (including a target reactive moiety) under conditions suitable for candidate reactive moiety and target reactive moiety to form a covalent bond, (b) a primer hybridization and extension step, and (c) a subsequent PCR amplification step.

Some ID-PCR methods described herein include (a) contacting a template (including a candidate ligand) with a primer (including a target molecule) under conditions suitable for a candidate ligand to bind to the target molecule, (b) a primer hybridization and extension step, and (c) a subsequent PCR amplification step.

Some aspects of the invention relate to strategies for the identification of bond-forming and bond-cleaving reactivity in a single-phase format. Some aspects of the invention relate to strategies for the identification of ligand binding activity in a single-phase format. Some aspects of this invention provide methods that obviate the need for time- and/or work-intensive manipulations that conventional selection strategies are burdened with. Some aspects of this invention provide systems for reactivity-dependent and interaction-dependent polymerase chain reaction, reactivity and interaction identification strategies, that directly link bond formation, bond cleavage, or ligand interaction with the amplification of desired sequences.

In some embodiments, RD-PCR includes the steps of (i) providing a nucleic acid template including a first primer hybridization site, a sequence tag, a second primer hybridization site, and a candidate reactive moiety; (ii) contacting the nucleic acid template with a first primer including a sequence complementary to the first primer hybridization site, a third primer hybridization site, and a target reactive moiety; (iii) incubating the nucleic acid template contacted with the first primer under conditions suitable for the candidate reactive moiety to form a covalent bond with the target reactive moiety; (iv) incubating the nucleic acid template contacted with the first primer under conditions suitable for covalently bound first primer to hybridize with the first primer hybridization site of the nucleic acid template it is covalently bound to and for primer extension; (v) contacting the nucleic acid template contacted with the first primer with a PCR primer complementary to the second primer hybridization site and a PCR primer complementary to the third primer hybridization site or with a PCR primer complementary to the second and third primer hybridization site; and (vi) performing a polymerase chain reaction to amplify the template, or a portion of the template, including the sequence tag.

Figure 12:
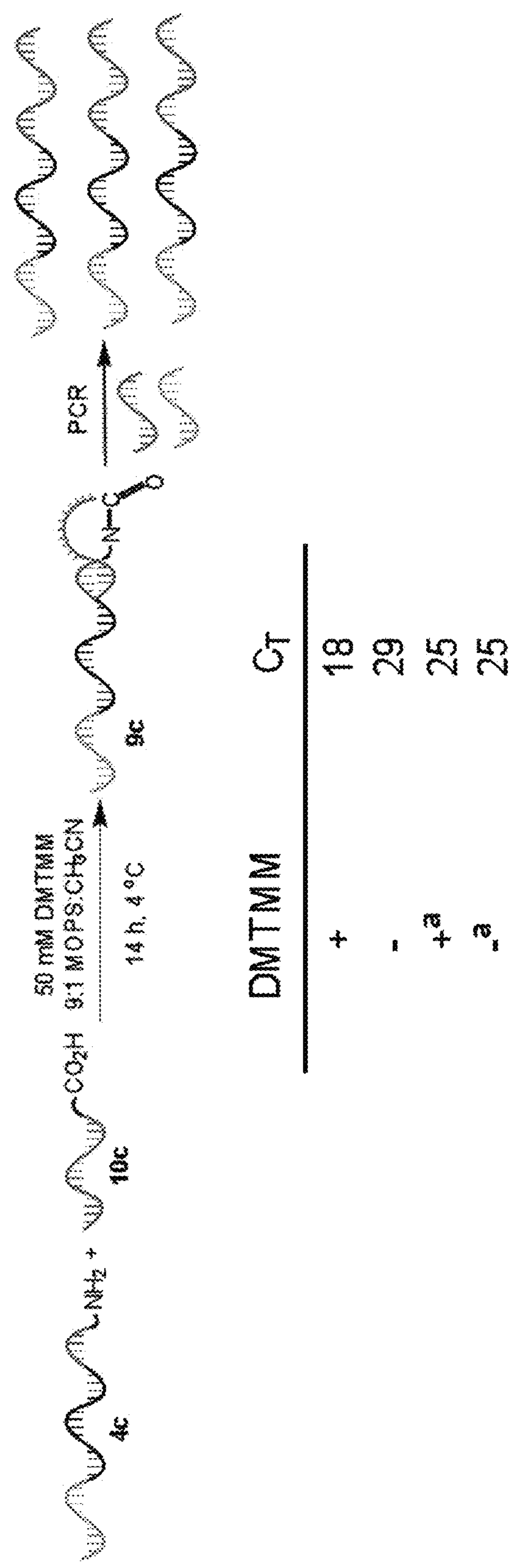
FIG. 12. An example of amide formation-dependent PCR.

In some embodiments, both the candidate and the target reactive moiety are provided in a reactive form (see, for example, amide-formation dependent RD-PCR described in FIG. 12 and related text in the Example section below). In some embodiments, the candidate reactive moiety is provided in an inactive form (see, for example, FIG. 7 and related text in the Example section). Such embodiments, generally, include an additional step of exposing the reactive moiety to conditions and/or a reagent suitable to render the inactive reactive moiety active (i.e., deprotecting).

Design of the template and primer may follow the specific parameters exemplified herein or may follow parameters for PCR template and primer design well known to those of skill in the art. Template design depends on the specific RD-PCR application to be performed. For example, in some embodiments, only a single reactive moiety may be tested for its ability to form a covalent bond with a target reactive moiety. In these embodiments, a template may be designed that does not include a sequence tag identifying the reactive moiety.

In some embodiments, a template may include a second primer hybridization site in addition to the primer hybridization site complementary to a primer including a target reactive moiety (the first primer hybridization site). The second primer hybridization site may be complementary to a PCR primer (a PCR primer hybridization site). In some embodiments, the template may include only one primer hybridization site and a linker including the primer hybridization site complementary to a PCR primer may be ligated to the template at some point before PCR amplification.

In some embodiments, the primer including the target reactive moiety includes a PCR primer hybridization site. In some embodiments, the primer including the target reactive moiety does not include a PCR primer hybridization site.

Figure 6:
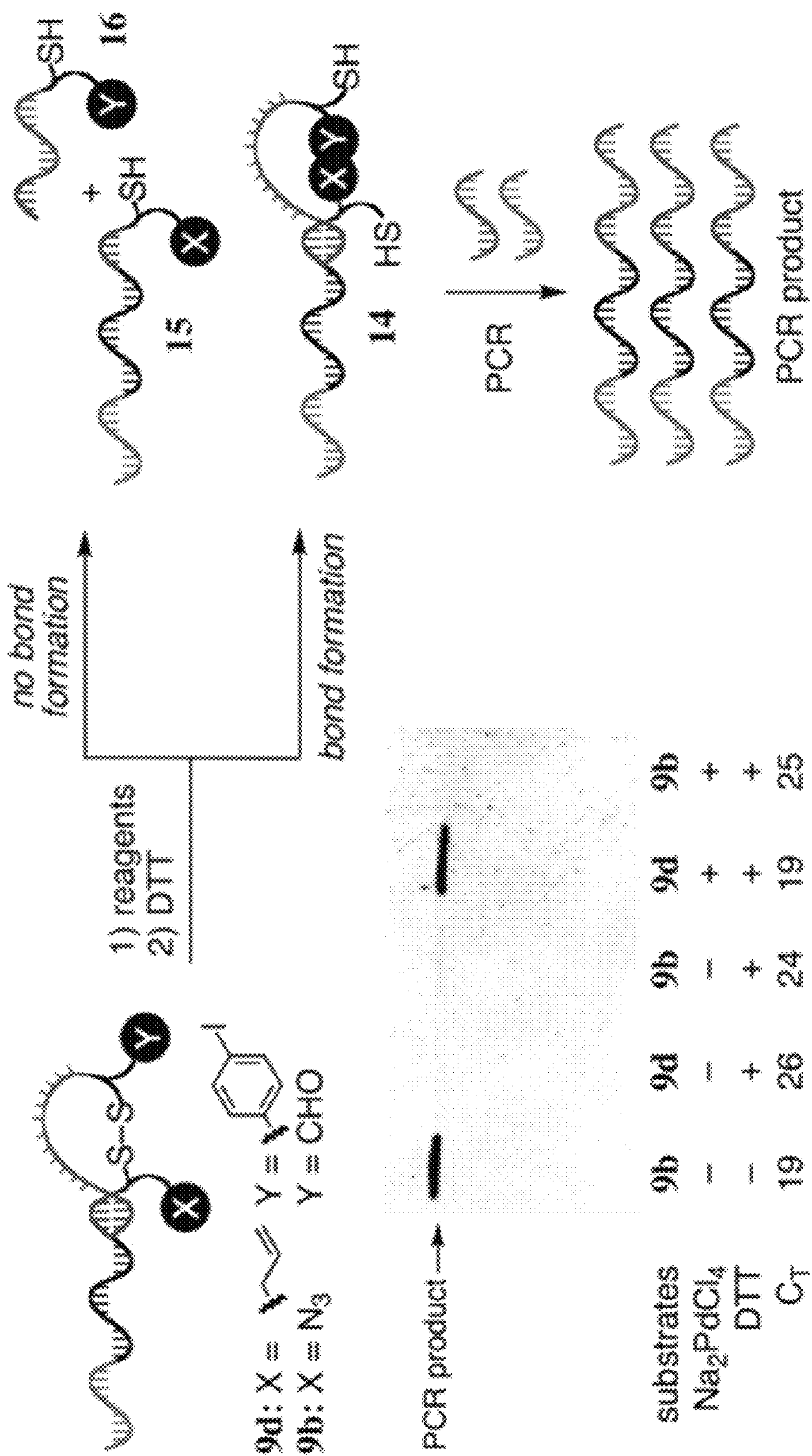
FIG. 6. RD-PCR-based DNA-encoded reaction discovery selection. PCR conditions for PAGE samples: 1 fmol of 9 in 20 μL, 23 cycles.

In some embodiments, the end-product of the covalent binding of target moiety to candidate moiety, first primer hybridization and extension is a molecule including a sequence tag flanked by PCR primer hybridization sites (see, for example, FIG. 6, #14). In some embodiments, the PCR primer hybridization sites include the same sequence. In some embodiments, only one PCR primer that hybridizes to the PCR primer hybridization sites flanking the sequence tag of the template is used in the PCR step. In some embodiments, (a) a PCR primer that hybridizes to a PCR primer hybridization site flanking the sequence tag of the template, and (b) a PCR primer that hybridizes to a PCR primer hybridization site on the other side of the sequence tag of the template is used in the PCR step. In some embodiments, a PCR primer hybridizes to the first primer hybridization site (i.e., the site that the first primer hybridizes to. In such embodiments, a first primer may be provided that does not include a second primer hybridization site.

In some embodiments, a template is provided that includes a spacer sequence between the first primer hybridization site and the candidate reactive moiety. In some embodiments, a first primer is provided that includes a spacer sequence between the sequence complementary to the first primer hybridization site and the target reactive moiety. In some embodiments both template and first primer include a spacer sequence between the respective reactive moiety and a sequence involved in primer hybridization. In some embodiments, the spacer sequence is designed to allow the first primer to hybridize with the first primer hybridization site of the template. A spacer sequence may be designed by methods well known to those of skill in the art. In general, a spacer sequence should not be complementary to any sequence of the template or the primer.

Primer extension is generally carried out by a nucleic acid polymerase, for example, a DNA or RNA polymerase. In some embodiments, a template and an extended primer are contacted with a PCR primer and exposed to conditions suitable to perform a polymerase chain reaction. Reagents and conditions for primer hybridization and extension are well known to those of skill in the art.

In some embodiments, a nucleic acid template including a candidate reactive moiety and a primer including a target reactive moiety are provided as separate (not covalently linked) molecules. In some embodiments, a nucleic acid template including a candidate reactive moiety and a primer including a target reactive moiety are provided as temporarily linked (e.g., covalently or non-covalently linked) molecules, wherein the linkage is not via a covalent bond between the candidate and the target reactive moiety and the template and primer are contacted or exposed to conditions suitable to undo the linkage before the primer extension step. For an example of an embodiment including temporarily linked template and primer, see FIG. 6.

In some embodiments, the ability of a single candidate reactive moiety to bind to a target reactive moiety is determined. In such embodiments, a template may be used that does not include a sequence tag. In such embodiments, the amplification of a template sequence during the PCR step, for example, at a cycle number at which non-covalently bound primer does not yield an amplified template sequence, may indicate that the candidate reactive moiety can covalently bind to the target reactive moiety under the respective conditions.

In some embodiments, the ability of a plurality of candidate reactive moieties to bind to a target reactive moiety is determined. In some such embodiments, a plurality of nucleic acid templates, each linked to a candidate reactive moiety, is contacted with a first primer. In some embodiments, the sequence tag of each template identifies the candidate reactive moiety it includes. In some embodiments, the sequence tag sequence of a PCR product is determined, for example, by sequencing methods well known to those of skill in the art, and a reactive moiety able to covalently bind to the target reactive moiety provided in the respective RD-PCR reaction is identified.

In some embodiments, RD-PCR is used to identify a substrate of an enzyme. In some embodiments, a template is provided that includes a candidate enzyme substrate, for example, a polypeptide or nucleic acid sequence. In some embodiments, the reaction catalyzed by the enzyme to be investigated results in the formation of a reactive moiety as part of the candidate enzyme substrate. For example, hydrolysis of a covalent bond within the substrate may leave a reactive moiety, (e.g., an amino group, a carboxyl group, or a hydroxyl group) at the cleavage site. For another example, phosphorylation or methylation of a candidate substrate may generate a reactive moiety as part of the respective candidate enzyme substrate.

Figure 7:
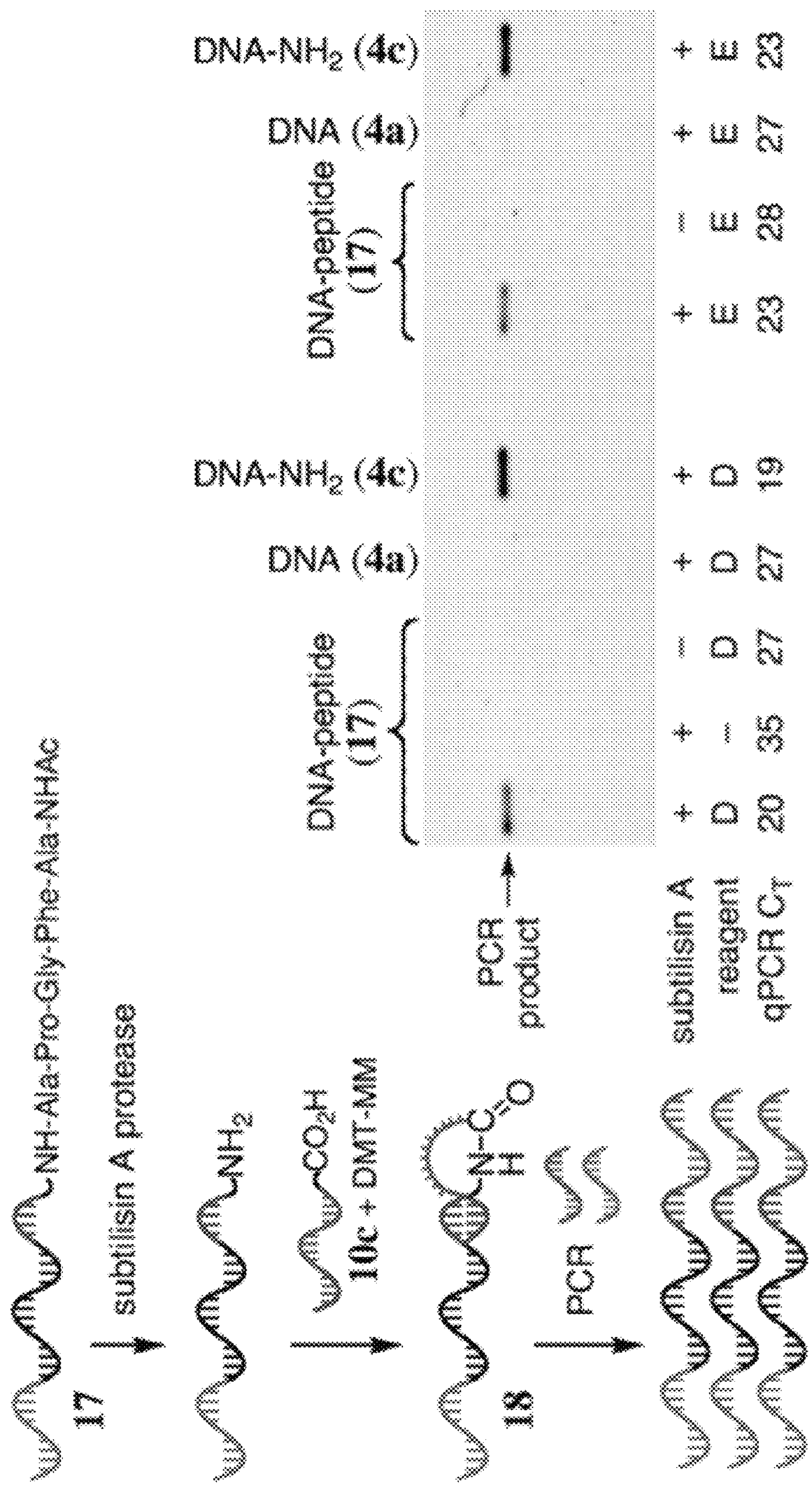
FIG. 7. RD-PCR-based protease-mediated peptide cleavage selection. PCR conditions for PAGE samples: 19 fmol of DNA in 30 μL, 23 cycles (lanes 1-5) or 25 cycles (lanes 6-9). D=DMT-MM; E=EDC+sNHS.

In some embodiments, RD-PCR is used to identify a substrate of a protease (for example, see FIG. 7 and related text in the Example section). In some embodiments, a template is provided including a candidate amino acid sequence for a protease. In some embodiments, hydrolysis of a covalent bond within a candidate amino acid sequence by a protease results in the formation of a reactive moiety, for example, an amine group, able to form a covalent bond with a target reactive moiety, for example, a carboxyl group. In some embodiments, a plurality of templates including a candidate protease substrate peptide are provided and contacted with a protease under conditions suitable for the protease to bind and cleave its target peptides. Suitable conditions for in vitro protease binding and activity are well known to those of skill in the art for many different proteases. For example, suitable conditions for various proteases are described in Antalis et al., *Proteases in Cancer: Methods and Protocols* (*Methods in molecular biology*), Humana Press, 1$^{st}$ edition, 2009. In some embodiments, a library of candidate protease substrate peptides is screened for their ability to be cleaved by a specific protease and the specific candidate substrate is identified by the sequence tag of the template. In some embodiments, a specific candidate protease substrate peptide may be included in a template including a specific sequence tag, thus allowing for identification of a candidate substrate that is a target of a specific protease by the sequence tag sequence of a RD-PCR product resulting from an RD-PCR procedure employing the protease. In some embodiments, a plurality of identified protease substrate sequences for a specific protease are combined into a list, or a substrate profile, of the protease. The identification of a protease substrate sequence, or the generation of a protease substrate profile may be useful in predicting protease target structures and/or identifying a molecular in vivo target of a protease. In some embodiments, where a plurality of candidate substrates is screened, a plurality of RD-PCR products with different sequence tag sequences is amplified, and a plurality of protease substrate sequences are identified, the sequences may be compared and aligned, and/or a consensus sequence may be generated from the sequences identified. Methods to generate consensus sequences from a list of sequences are well known to those of skill in the art. Quantitative information from the RD-PCR procedure, for example, the relative amounts of a template with a specific sequence tag among all amplified templates, may be used to determine enzyme preference for a specific substrate. Methods of reflecting enzyme preference in consensus sequence calculations are well known to those in the art.

In some embodiments, RD-PCR is used to identify a substrate of a functional nucleic acid (e.g., a ribozyme or a DNAzyme). In some embodiments, a template is provided including a candidate substrate for a functional nucleic acid. In some embodiments, hydrolysis of a covalent bond within a candidate substrate by a functional nucleic acid results in the formation of a reactive moiety, for example, an amine group, a carboxyl group, a phosphate group, or a hydroxyl group, able to form a covalent bond with a target reactive moiety. In some embodiments, a plurality of templates including a candidate substrate are provided and contacted with a functional nucleic acid under conditions suitable for the functional nucleic acid to bind its substrate and catalyze the desired reaction (e.g. cleavage or formation of a covalent bond). Suitable conditions for in vitro nucleic acid enzyme binding and activity are well known to those of skill in the art for various functional nucleic acids, such as ribozymes and DNAzymes. For example, suitable conditions for various ribozymes and DNAzymes are described in Sioud, *Ribozymes and siRNA protocols*, Humana Press, 2004, and Brakmann et al., *Evolutionary methods in Biotechnology*, Wiley-VCH, 2004, both of which are incorporated herein by reference. In some embodiments, a library of candidate substrates, for example, a variety of candidate nucleic acid or amino acid sequences, is screened for an actual substrate of a specific functional nuclei acid. An actual substrate can be identified by the sequence tag of the template it was coupled to after amplification of the template in a polymerase chain reaction. If a plurality of actual substrates is identified for a given functional nucleic acid, enzyme profiling and determination of consensus substrate sequence, if applicable, may be performed as outlined above.

For example, in some embodiments, a nucleic acid template is provided that includes a first primer hybridization site, a sequence tag, a candidate substrate nucleic acid sequence, and a PCR primer hybridization site. In some embodiments, the template is contacted with a primer that includes a reactive moiety that can form a covalent bond to a nucleic acid. In some embodiments, the template is designed in a manner that the end at which the candidate substrate is situated is modified in a manner precluding the formation of a covalent bond between the reactive moiety of the first primer and the template. In some embodiments, the template is contacted with an endonuclease that catalyzes the cleavage (e.g., by hydrolysis) of an internucleotide bond in its substrate sequence. In some embodiments, cleavage of an internucleotide bond within a substrate nucleic acid sequence leaves an unmodified nucleic acid end (e.g., a free hydroxyl group) to which the reactive moiety of the first primer can form a covalent bond. In some embodiments, a part of the template that included actual substrate nucleic acid sequences is then amplified in the polymerase chain reaction and the sequence of the substrate nucleic acid sequence is identified by the sequence tag of the template.

In some embodiments, RD-PCR is used to identify a functional nucleic acid that can catalyze a specific reaction on a given substrate. In some embodiments, a template is provided including a candidate functional nucleic acid, a first primer hybridization site, and, optionally, a sequence tag, and a PCR primer hybridization site. In some embodiments, the functional nucleic acid is a cis-acting nucleic acid and the template also includes a specific substrate. In such embodiments, the template is contacted with a first primer coupled to a reactive moiety able to form a covalent bond to the template only if the candidate functional nucleic acid has catalyzed a specific reaction on the substrate. In other embodiments, a specific substrate is provided coupled to the first primer. In such embodiments, the template comprises a reactive moiety able to form a covalent bond to the first primer only after the candidate functional nucleic acid has catalyzed a reaction on the substrate. In some embodiments, a part of the template including the functional nucleic acid is amplified in the polymerase chain reaction. In some embodiments, the functional nucleic acid sequence is determined by the sequence tag of the template. In some embodiments, the sequence of the functional nucleic acid is amplified as part of the template in the polymerase chain reaction and can be determined directly by sequencing.

In some embodiments, a library of templates is provided including a candidate functional nucleic acid, for example, a ribozyme or a DNAzyme, a first primer hybridization site, a reactive moiety able to form a covalent bond with a nucleic acid, but not with any other nucleic acid template provided in the library, and, optionally, a sequence tag. In some embodiments, the template is contacted with a first primer including a specific substrate, for example, a specific nucleic acid sequence, wherein the first primer is designed in a manner that it cannot form a covalent bond with the provided template unless the substrate is modified. For example, in some embodiments, the 5'-end of the first primer includes a protecting group precluding ligation of the first primer to a template molecule. Only after modification of the substrate, for example, by cleavage of an internucleotide bond by a functional nucleic acid, can a covalent bond be formed. In some embodiments, the template is contacted with the first primer under conditions suitable for a functional nucleic acid to bind its substrate and catalyze a chemical reaction, for example, cleavage of an internucleotide bond, and for ligation of the first primer to the nucleic acid template. In some embodiments, a part of the template is amplified in a subsequent polymerase chain reaction, and the sequence of a functional nucleic acid is determined by the sequence tag associated with it, or by directly sequencing the functional nucleic acid portion of the template.

Suitable conditions for an enzyme to bind and react with a substrate molecule depend, of course, on the nature of the enzyme and the substrate and the reaction being catalyzed. Suitable conditions for many enzymes and enzyme types are known to those of skill in the art. For example, suitable conditions for various proteases are described in Antalis et al., *Proteases in Cancer: Methods and Protocols* (*Methods in molecular biology*), Humana Press, $1^{st}$ edition, 2009. Similarly, suitable conditions for enzymes the activity of which has been examined in a published in vitro assay, can be extrapolated from the respective publication. Conditions for enzymes similar to those for which in vitro assay conditions are known, can be extrapolated from assay parameters of closely related enzymes. In general, mimicking aspects of the physiological conditions under which an enzyme functions in vivo will provide suitable conditions for an in vitro assay and, thus, for RD-PCR.

Figure 16:
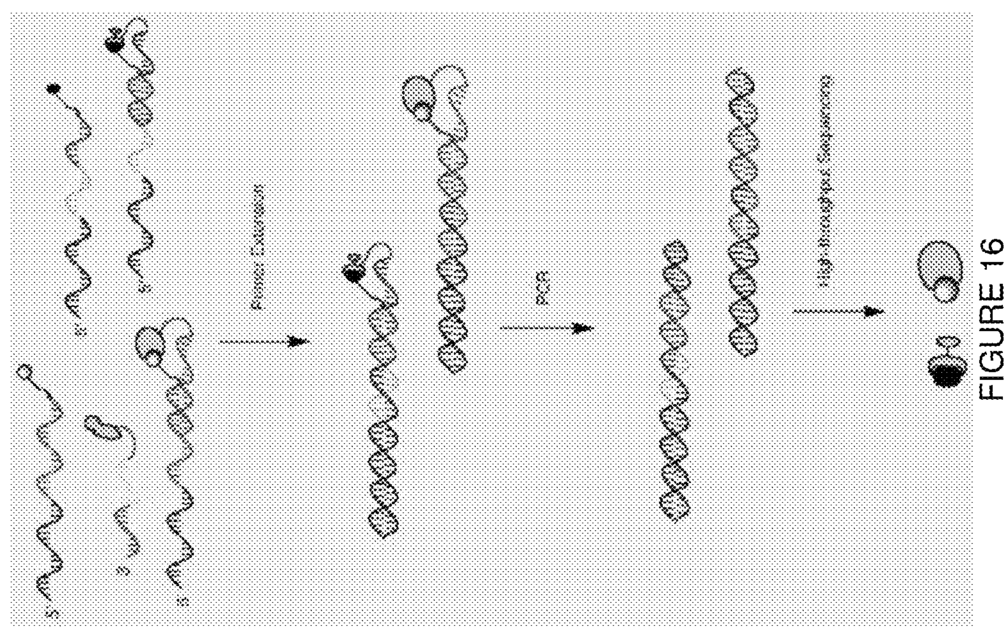
FIG. 16. Principles underlying interaction-dependent PCR (ID-PCR). Non-covalent binding between a candidate ligand and a target are displayed as examples of ID-PCR.

In some embodiments, a PCR is performed with a template and a primer that interact not via covalent, but via non-covalent interaction, as shown in FIG. 16. Such embodiments are referred to as “interaction-dependent PCR,” or ID-PCR. Non-covalent interactions suitable for ID-PCR reactions include, for example, interactions of chemical or biological ligands (e.g., interactions between a protein and a small chemical compound, between two chemical compounds, between an enzyme and its substrate, between a protein and its ligand, between an antibody and its epitope, etc.). Non-limiting examples of interactions suitable for ID-PCR include hydrogen bonds, electrostatic interactions, magnetic interactions, π-stacking interactions, dipole-dipole interactions, hydrophobic interactions, van der Waals interactions, or combinations thereof. In some embodiments, the non-covalent interaction is a direct interaction between a ligand coupled to a nucleic acid template and a target molecule coupled to a first primer. In some embodiments, the non-covalent interaction is an indirect interaction between a ligand coupled to a nucleic acid and a target molecule coupled to a first primer, for example, via a third molecule that both (ligand and target molecule) interact with. In some such embodiments, ligand and target molecule are of identical structure and bind to a multivalent binding molecule. Typically, non-covalent interactions suitable for ID-PCR are characterized by a $K_D<10^{-6}$. In some ID-PCR embodiments, such non-covalent interactions are characterized by a $K_D<10^{-7}$. In some ID-PCR embodiments, such non-covalent interactions are characterized by a $K_D<10^{-8}$. In some ID-PCR embodiments, such non-covalent interactions are characterized by a $K_D<10^{-9}$. In some ID-PCR embodiments, such non-covalent interactions are characterized by a $K_D<10^{-10}$. In some ID-PCR embodiments, such non-covalent interactions are characterized by a $K_D<10^{-11}$. In some ID-PCR embodiments, such non-covalent interactions are characterized by a $K_D<10^{-12}$. In some ID-PCR embodiments including non-covalent interaction formation, the interaction between both binding partners (one coupled to the template, the other to the first primer) forms in the absence of any enzymatic activity. In some embodiments, a library of templates coupled to a candidate ligand, for example, a small compound candidate ligand, is screened using ID-PCR for an actual ligand of a given protein coupled to the first primer.

Suitable conditions for non-covalent interactions, primer hybridization and extension will depend, of course, on the nature of the non-covalent interaction to be screened for. Typical conditions for the screening of various types of non-covalent interactions are well known in the relevant arts and have been documented, for example, in numerous publications regarding screens of compound or protein libraries using conventional methodology, such as Cabilly, *Combinatorial Peptide Library Protocols*, Humana Press, 1998, and Janzen, *High Throughput Screening: Methods and Protocols*, Humana Press, 2002, both of which are incorporated herein by reference.

In some embodiments, ID-PCR is used to screen two libraries of binding partners against each other. For example, in some ID-PCR embodiments, a library of templates is provided including candidate polypeptides. In some embodiments, the specific candidate polypeptide a template is coupled to can be identified by the template's sequence tag. In some embodiments, the candidate polypeptides are rationally selected, for example, only polypeptides representing proteins, or fragments of proteins, from a biological pathway relevant for a specific disease may be included in a specific library. In some embodiments, only polypeptides that are either proteins, or fragments of proteins, that activate or inhibit of a specific biological pathway are included in the template library. In other embodiments, the template library is not rationally selected, but may, for example, be a library of randomized compounds, peptides, or nucleic acids. In some embodiments, the library of templates is contacted with a library of primers coupled to candidate ligands, for example, peptides or small chemical compounds. In some embodiments, the specific ligand a primer molecule is coupled to can be identified by a sequence tag included in the primer. In some embodiments, the library of candidate polypeptides is contacted with the library of candidate ligands under conditions suitable for binding of a polypeptide to a ligand. The ID-PCR reaction amplifies a sequence including a sequence tag from the template (identifying the polypeptide) and a sequence tag from the primer (identifying the ligand). In some embodiments, ID-PCR is used to identify polypeptide-ligand pairs in simultaneous screens of multiple libraries. Thus, ID-PCR is useful in identifying binding partners (targets) of leads in drug development.

In some embodiments, RD-PCR or ID-PCR is used as an environmental sensor. In some embodiments of RD-PCR, a template is provided including a reactive moiety that, under suitable conditions, only forms a covalent bond to a reactive moiety coupled to a first primer in the presence or absence of an environmental parameter or analyte, for example, in the presence of a specific metal ion, in the presence of an oxidizing environment, in the presence of an enzymatic activity, or in the presence of an environmental toxin or pathogen. In some embodiments of ID-PCR, a template is provided including a ligand that, under suitable conditions, only interacts with a target molecule coupled to a first primer in the presence or absence of an environmental parameter or analyte as described herein. In some ID-PCR embodiments, the template-coupled ligand does not directly interact with the primer-coupled target molecule, but interacts with the target molecule indirectly, for example, via a third molecule that interacts with both the ligand and the target molecule. In some such embodiments, the template-coupled ligand and the primer-coupled target molecule share the same binding domain structure and interact via a multivalent binding molecule. In some embodiments, the polymerase chain reaction depends on the formation or the cleavage of a covalent bond catalyzed by an enzyme only in the presence or the absence of an enzymatic co-factor. Co-factors of enzymes are well known in the art and include, for example, inorganic cofactors and organic cofactors. Inorganic cofactors include, for example, ions of Li, Na, K, Mg, Ca, Sr, Ba, Cr, Mn, Fe, Co, Ni, Cu, Zn, Cd. Organic cofactors are generally small organic molecules (typically with a mass of less than 1 kDa), and include, for example, vitamins and vitamin derivatives (e.g., thiamine, niacin, pyridoxine, lipoic acid, cobalamine, biotin, pantothenic acid, folic acid, menaquinone, ascorbic acid, riboflavin, and their derivatives), and other organic cofactors (e.g. ATP, coenzyme B, M, and Q, glutathione, tetrahydrobiopterin, and methanofuran). In some embodiments, a biosensor RD-PCR or ID-PCR reaction is designed in a manner that the formation of the covalent bond or the interaction between first primer and template depends on a reaction catalyzed only in the presence of a specific cofactor. In some embodiments, a sample from the environment to be tested is obtained and added to the RD-PCR or ID-PCR reaction either in its original form or in a processed form, depending on the nature of the environmental parameter to be investigated. In some embodiments, if the RD-PCR or ID-PCR reaction yields an amplicon at a predefined PCR cycle number, then it is determined that the environmental sample contained the environmental parameter or analyte at the time the sample was taken. In some embodiments, if the RD-PCR or ID-PCR reaction does not yield an amplicon at a predefined cycle number, then it is determined that the environment to be tested did not contain the environmental parameter or analyte or contained it only below threshold concentration at the time the sample was taken.

In some embodiments, a plurality of RD-PCR or ID-PCR template-primer pairs are provided in a multiplex reaction, wherein the reaction or interaction of different template-primer pairs depends on the presence or the absence of different analytes, thus allowing one to analyze multiple analytes or environmental parameters in parallel. For example, two template-primer pairs may be provided, wherein formation of a covalent bond between template and primer of the first pair depends on the presence of a first analyte and formation of a covalent bond between template and primer of the second pair depends on the presence of a second analyte. In some embodiments, a sequence tag is included in the template identifying the analyte involved in the reaction or the interaction between the template and the primer. In some embodiments, the presence or absence of a specific analyte is determined by identifying the sequence tag of an amplicon from a multiplex RD-PCR or ID-PCR reaction. In some embodiments, different template-primer pairs of a multiplex RD-PCR or ID-PCR reaction are designed to yield amplicons of different length, allowing a determination of the presence or absence of a specific analyte or environmental condition by the length of the amplicon yielded in the polymerase chain reaction. For example, a first template-primer pair may be designed to yield an amplicon of about 250 base pairs in the presence of a first analyte and a second template-primer pair may be designed to yield an amplicon of about 500 base pairs in the presence of a second analyte. In this exemplary embodiment, an amplicon of about 250 base pairs is indicative of the presence of the first analyte and an amplicon of about 500 base pairs is indicative of the presence of the second analyte. Methods for determining the length of a PCR amplicon are well known in the art and include, for example, gel-electrophoresis.

In some embodiments, a kit containing RD-PCR or ID-PCR reagents are provided. In some embodiments, a kit is provided containing a nucleic acid molecule, for example, a nucleic acid template or a primer. In some embodiments, a kit is provided containing a primer coupled with a target reactive moiety. In some embodiments, a kit is provided containing a nucleic acid template coupled with a candidate reactive moiety. In some embodiments, a kit is provided containing a library of candidate reactive moieties for RD-PCR or a library of candidate ligands for ID-PCR, for example, a plurality of nucleic acid templates coupled with a candidate reactive moiety or a candidate ligand. In some embodiments, a kit is provided containing a reagent for coupling a nucleic acid, for example, a nucleic acid template or primer, with a reactive moiety or a binding molecule, for example, a candidate or target reactive moiety or a candidate ligand or target molecule. In some embodiments, a catalyst or an enzyme are provided. In some embodiments, reagents to generate suitable conditions for a chemical reaction or interaction, or for a specific catalyst or enzyme are provided. In some embodiments, a kit is provided containing PCR reagents, for example, a PCR primer, a PCR buffer, a PCR enzyme, for example, a thermophilic DNA polymerase, and/or a salt or co-factor necessary for the function of the PCR enzyme, for example, $Mg^{2+}$. In some embodiments, instructions containing information or protocols for the use of the kit to perform RD-PCR or ID-PCR are provided.

EXAMPLES

Figure 2:
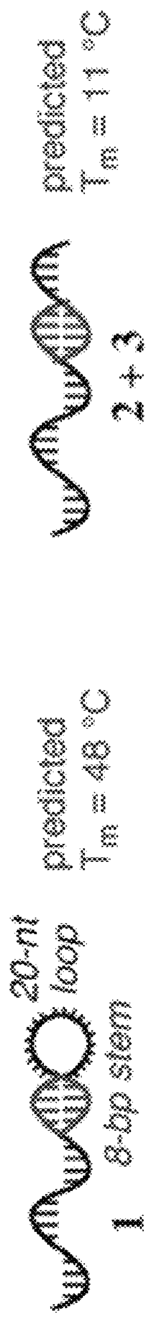
FIG. 2. Principles underlying reactivity-dependent PCR (RD-PCR). Conditions in (a): 10 nM DNA, 2 mM $Mg^{2+}$, 100 mM NaCl.
Figure 2:
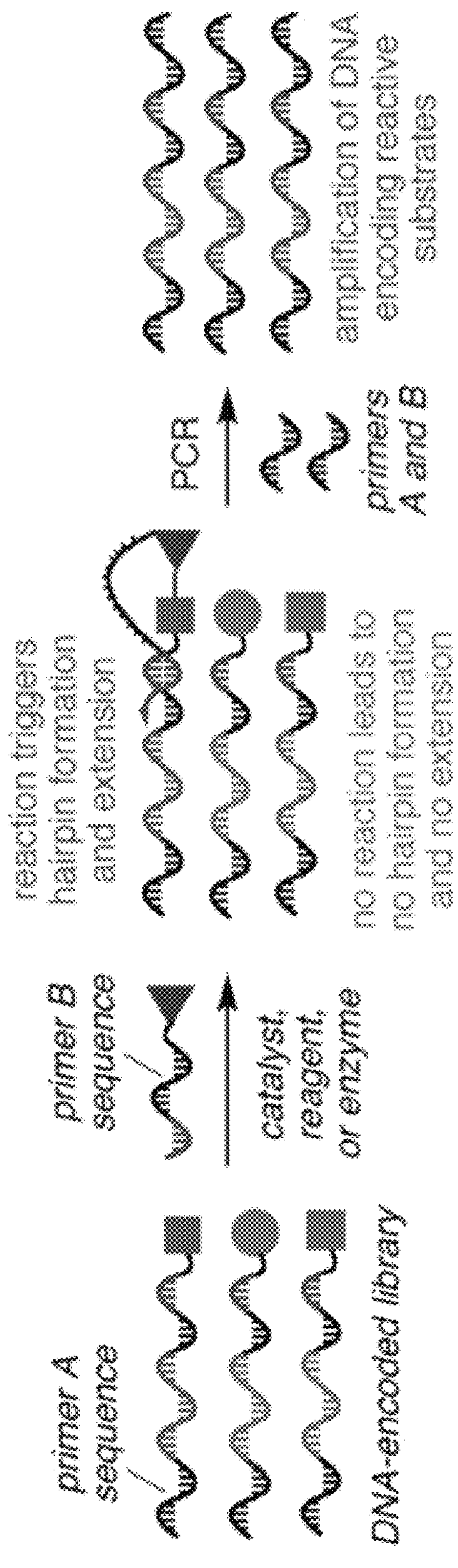

Example 1: Reactivity-Dependent PCR: Direct, Solution-Phase In Vitro Selection for Bond Formation RD-PCR is based on the well-established observation that the melting temperatures ($T_m$) of double-stranded nucleic acids are substantially higher when hybridization occurs intramolecularly as opposed to intermolecularly.(10) For example, the DNA hairpin 1 with an 8 bp stem is predicted (11) to exhibit a $T_m$ of 48° C., while the intermolecular hybridization of two DNA strands of the same sequence (2 and 3) is predicted to be far less favorable, with a $T_m$ of only 11° C. (FIG. 2). The significant difference in intramolecular versus intermolecular duplex stability could enable a new type of in vitro selection, wherein bond formation or bond cleavage is transduced into the formation of a self-priming DNA hairpin. This hairpin enables the selective PCR amplification of those DNA sequences that encode the reactive species (FIG. 2*b*).(12)

Figure 3:
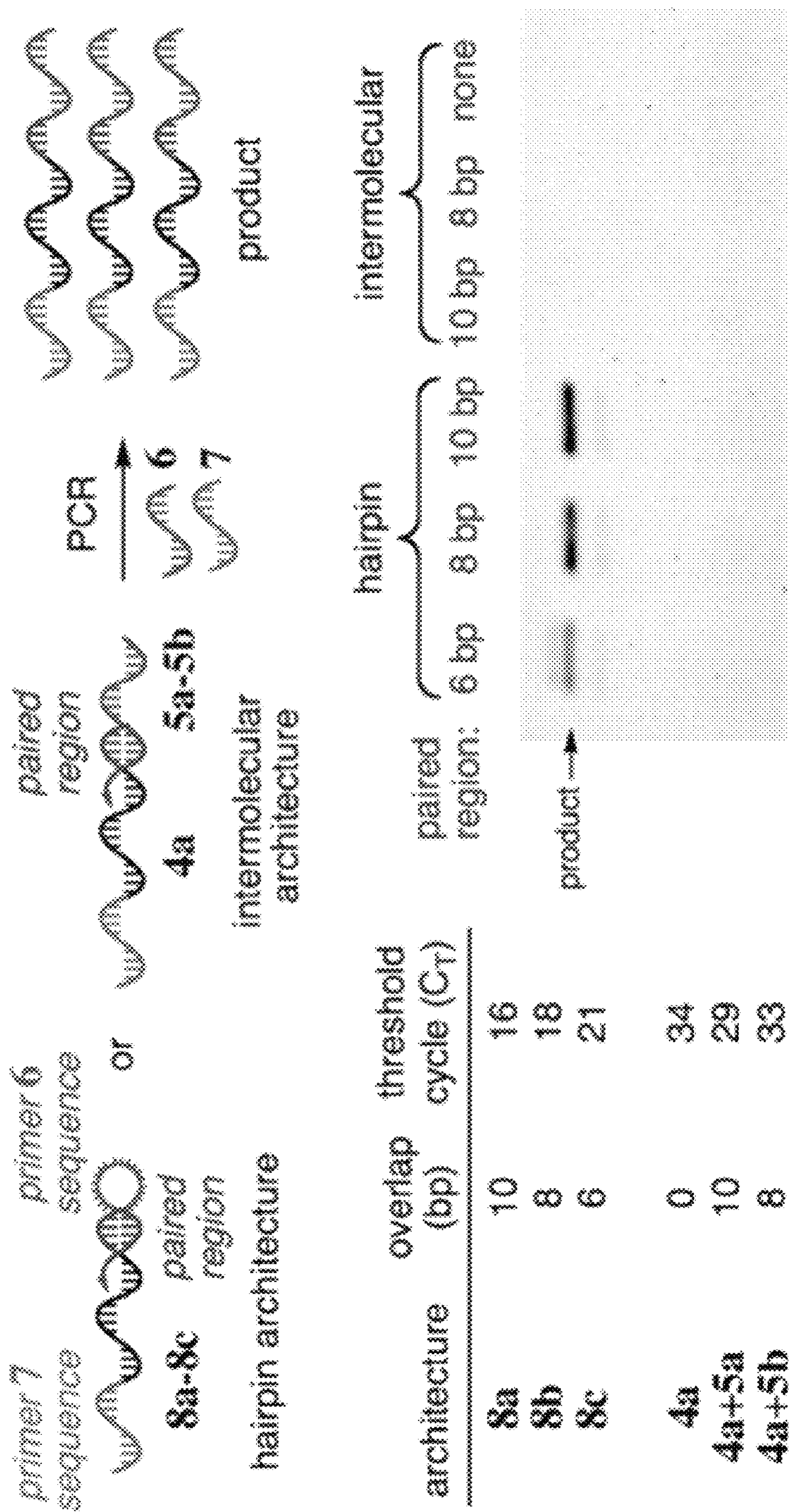
FIG. 3. Comparison of PCR efficiency of intramolecularly primed versus intermolecularly primed DNA templates. PCR conditions for PAGE samples: 19 fmol of 8 or 19 fmol of 4a+5 in 30 μL, 25 cycles.

The ability of intramolecular self-priming to result in preferential DNA amplification was assessed first. A series of oligonucleotide pairs was synthesized (4a+5), each predicted to hybridize intermolecularly at their 3' ends to form a short duplex region of 8 or 10 bp (FIG. 3).

The 5'-end of each DNA oligonucleotide in the pair contained a sequence identical to either primer 6 or primer 7. PCR amplification cannot occur until after DNA hybridization and 3' extension take place to generate a single-stranded DNA molecule containing both primer 6 and a sequence complementary to primer 7. This 3'-extended species can then hybridize with primer 7 and initiate PCR amplification.

An analogous series of DNA oligonucleotides capable of hybridizing intramolecularly to form hairpin structures with 10-, 8-, or 6-bp stems was prepared (8a-8c). As with the intermolecularly hybridizing oligonucleotides, PCR amplification must be initiated by primer extension of the 3'-end. Quantitative, real-time PCR(13) (qPCR) was used to compare the ability of these oligonucleotides to undergo PCR amplification.

Consistent with our initial hypothesis, under identical PCR conditions and with equal starting concentrations of DNA, the intramolecularly hybridizing templates were amplified much more efficiently than their intermolecular counterparts (8a vs 4a+5a, 8b vs 4a+5b). The intramolecularly hybridizing templates reached a threshold level of amplified product 13 to 15 PCR cycles ($C_T$) earlier than the intermolecular templates, corresponding to a >2(13)-fold (>8000-fold) difference in effective initial template abundance. These qPCR results were corroborated by PAGE analysis; after 25 cycles of PCR, amplified product was only detected in reactions containing hairpin DNA. Collectively, these findings demonstrate that intramolecularly hybridizing templates can be amplified to abundant levels under conditions that fail to appreciably amplify the corresponding intermolecularly hybridizing templates. Subsequent experiments in this work were carried out with an 8-base stem, which was found to optimally balance robust intramolecular priming and poor intermolecular priming (see below).

Figure 4:
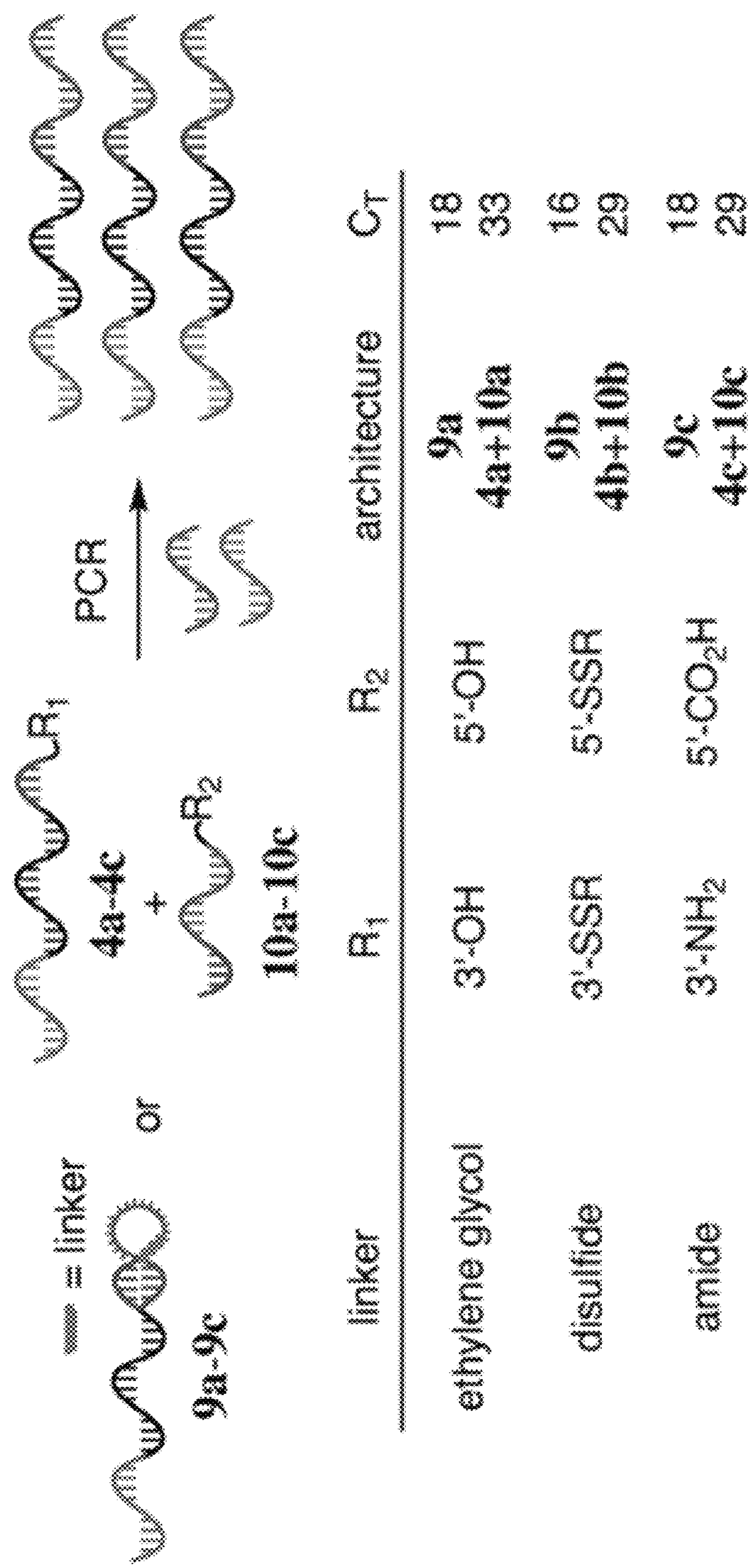
FIG. 4. Non-natural hairpin linkers support self-priming PCR. R=—$(CH_2)_6OH$.

To use RD-PCR in a general selection for bond formation, the covalently linked functional groups in the hairpin loop must not interfere with the required hybridization and 3'-extension events. To test the compatibility of non-natural linkers with the preferential amplification of self-priming templates, the qPCR experiment in FIG. 3 were repeated with a series of non-natural linker structures, including ether, disulfide, and amide hairpin linkers. In all cases tested, DNA templates containing non-natural linkers (9a-9c) were far more efficiently amplified than the analogous intermolecularly hybridizing templates (4+10) (FIG. 4).

Figure 5:
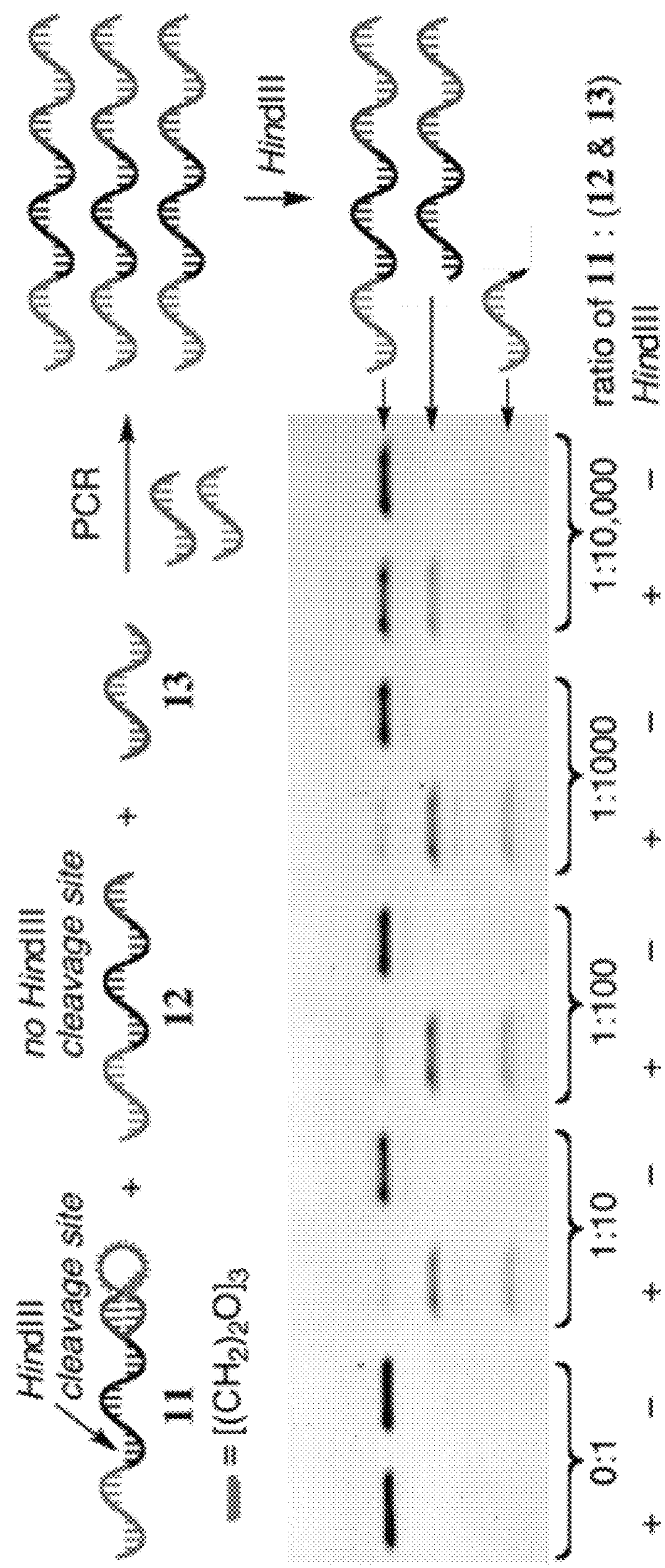
FIG. 5. Selectivity of RD-PCR in a library-format mock selection. PCR conditions: 19 fmol of 12 and 13 in 60 μL, 25-35 cycles.

Since RD-PCR will ultimately be applied to mixtures of both active (resulting in DNA hairpins) and inactive (resulting in separate linear oligonucleotides) library members, the ability of hairpin templates to undergo preferential amplification in the presence of large excesses of corresponding linear molecules was tested next (FIG. 5). For these library-format experiments, the hairpin (11) and linear (12) template sequences vary only by a single base, such that DNA amplified from the hairpin contains a cleavage site for the restriction enzyme HindIII, while DNA arising from 12 does not.

The quantity of 11 spiked into an equimolar mixture of 12 and 13 was varied to determine the selectivity of RD-PCR in a library format. As little as 1 attomol of 11 (600 000 molecules) could be selectively amplified in the presence of a 10 000-fold excess of 12 and 13. The use of larger quantities of hairpin (corresponding to a 10- to 1000-fold excess of 12 and 13) overwhelmingly provided the desired product. These results demonstrate the ability of hairpin templates to be preferentially amplified even in the presence of large excesses of linear templates and indicate that RD-PCR can be applied to library-format selections.(14)

Following these studies, RD-PCR was applied to two model in vitro selections. First, RD-PCR was validated as a bond-formation selection for DNA-encoded reaction discovery. Previously, DNA-encoded reaction discovery required the capture, washing, and elution of active library members on avidin-linked beads (FIG. 1*b*).(5) In a RD-PCR version of reaction discovery, pairs of functional groups are attached to encoding DNA strands (FIG. 6). A disulfide linker temporarily joins each substrate pair (9b, 9d). Exposure to a set of reaction conditions and subsequent cleavage of the disulfide bond provide one of two possible outcomes. If a new covalent bond has formed between the functional groups, the hairpin-forming nucleotides remain tethered together through the reaction product, leaving a self-priming DNA hairpin (14). If no bond has formed, then only intermolecular hybridization is possible (15+16), resulting in inefficient PCR amplification. In contrast with previous reaction discovery selections, the RD-PCR version requires no solid-phase steps and minimal manipulation.

To test the ability of RD-PCR to support reaction discovery, a disulfide-linked substrate (9d) with pendant alkene and aryl iodide groups was synthesized, which should undergo a Pd-mediated Heck-type reaction (FIG. 6).(15) An unreactive control substrate (9b) containing an azide and an aldehyde was similarly generated. Each substrate was treated with 1 mM $Na_2PdCl_4$ (which is reduced to Pd(0) in situ) in aqueous pH 7.5 buffer for 30 min at 65° C., followed by DTT to cleave the disulfide bond. The resulting material was subjected to PCR. The DNA attached to the alkene-aryl iodide pair (9d) amplified efficiently (FIG. 6). Omission of $Na_2PdCl_4$ resulted in much less efficient amplification. Likewise, the unreactive substrate pair 9b did not undergo PCR amplification after identical treatment. Omission of DTT, however, enabled the disulfide-linked starting substrate to amplify efficiently. Collectively, these results indicate that RD-PCR can selectively and efficiently amplify DNA templates that have undergone bond formation and that amplification is dependent on the intramolecularity of the resulting template-primer species.(16) These experiments were corroborated using an azide/alkyne substrate that undergoes a Cu(I)-catalyzed cycloaddition reaction (see below).

In principle, RD-PCR can also enable efficient selection for bond cleavage, which has yet to be studied in a DNA-encoded context. To explore this possibility, the ability of DNA-linked peptides to undergo cleavage mediated by a protease was evaluated (FIG. 7). Protease-mediated cleavage of a DNA-peptide conjugate would expose a primary amine group, which would then undergo DNA-templated amide bond formation to generate a hairpin template for efficient PCR.(17) In contrast, the absence of proteolysis should result in no amide formation and thus inefficient PCR amplification.

A DNA-N-acetyl-pentapeptide conjugate (17), synthesized by solid phase cosynthesis, was exposed to subtilisin A. The peptide sequence (Ac-N-AFGPA) was designed to include cleavage sites for subtilisin A.(18) The enzyme-treated DNA was combined with a carboxylic acid-linked DNA primer (10c) under conditions (DMT-MM or sNHS+EDC) that support DNA-templated amide bond formation. (19)

Addition of the protease-digested and carboxylate-ligated DNA-peptide conjugate (18) to a PCR reaction resulted in efficient PCR amplification. In contrast, no PCR product was detected by PAGE when unfunctionalized DNA (4a) was used in place of the pentapeptide or when subtilisin A was omitted. Likewise, omission of the amide formation reagents also resulted in inefficient PCR amplification, consistent with the necessity of intramolecular primer hybridization for rapid amplification. These findings together demonstrate the ability of RD-PCR to rapidly detect DNA-linked peptide substrates of protease enzymes.

In conclusion, RD-PCR was developed and validated as a new, entirely solution-phase method for the selective amplification of DNA sequences encoding molecules that undergo bond formation or bond cleavage.(9) By obviating the need to perform solid-phase capture, washing, and elution steps, RD-PCR can greatly streamline the selection process for applications such as DNA-encoded reaction discovery and protease activity profiling. Compared with the performance characteristics of previous in vitro selection methods,(3c, 5a) the data above suggest that RD-PCR may also offer superior enrichment factors (signal:background ratios).

Experimentals

General Methods.

DNA oligonucleotides were synthesized using standard automated solid-phase phosphoramidite coupling methods on a PerSeptive Biosystems Expedite 8909 DNA synthesizer or purchased from Integrated DNA Technologies. All reagents and phosphoramidites for DNA synthesis were purchased from Glen Research. Oligonucleotides were purified by reverse-phase high-pressure liquid chromatography (HPLC) using a C18 stationary phase and an acetonitrile/100 mM triethyl ammonium acetate gradient or by Oligonucleotide Purification Cartridge (Applied Biosystems). Oligonucleotide concentrations were quantitated by UV spectroscopy on a Nanodrop ND1000 Spectrophotometer. Non-commercial, modified oligonucleotides were characterized by LCMS on Waters Aquity UPLC equipped with a Waters Aquity UPLC BEH C18 column using an aqueous 6 mM tetraethyl ammonium bicarbonate/MeOH mobile phase. Electrospray mass spectrometry was carried out on a Waters Q-TOF premier instrument. All DNA sequences are written in the 5' to 3' orientation.

Gels stained with ethidium bromide were visualized on an Alpha Innotech AlphaImager HP. Fluorescence images were acquired on a GE Typhoon Trio variable mode imager. Solid phase peptide synthesis was carried out on an Applied Biosystems 433A peptide synthesizer using standard Fmoc chemistry. Water was purified with a Milli-Q purification system. All chemical reagents were purchased from Sigma-Aldrich, unless otherwise noted. DMT-MM was synthesized according to the method of Kunishima, M.; Kawachi, C.; Iwasaki, F.; Terao, K.; Tani, S. *Tetrahedron Lett.* 1999, 40, 5327. Subtilisin A was purchased from Sigma-Aldrich. HindIII and PvuII-HF were purchased from New England Biolabs.

General Method for PCR.

All PCR reactions were carried out with AmpliTaq Gold DNA Polymerase (0.1 μL/20 μL reaction volume, Applied Biosystems) in the provided buffer. PCR reactions included Mg2+ (3 mM), dNTPs (200 μM each, BioRad), and primers (500 nM each). Templates were amplified from a standard initial concentration of 625 pM, unless otherwise noted. The thermal cycling sequence was as follows: 95° C. for 10 minutes, then iterated cycles of 95° C. for 30 seconds, 58° C. for 30 seconds, and 72° C. for 30 seconds. In preparative PCR reactions, upon completion of the iterated cycles, a final incubation at 72° C. for 2 minutes was performed. For qPCR, conditions were identical to those above, except that Sybr Green I Nucleic Acid gel stain (0.5× final concentration from a 10,000× stock solution, Invitrogen) was added to the reaction mixture. Quantitative PCR experiments were performed in triplicate on a BioRad CFX96 Real-Time PCR Detection System.

Oligonucleotide Modeling Program (OMP) Calculation (FIG. 2*a*):

Sequence for Hairpin Architecture (Complementary Region in Bold)

1:
(SEQ ID NO: 2)
GCA GTA CCA ACC CTG TAC ACC ATC TCA AGT TCT ATG
TCT GAC TAC AGA GTG GGA TGC ATA GAA C

Sequences for Intermolecular Architecture 2:
(SEQ ID NO: 50)
GCA GTA CCA ACC CTG TAC ACC ATC TCA AGT TCT ATG

3:
(SEQ ID NO: 3)
TCT GAC TAC AGA GTG GGA TGC ATA GAA C

OMP calculation was performed using the following parameters: assay temperature: 37° C. Mg2+: 2 mM. Monovalent cations: 0.1 M. DNA concentration: 10 nM.

Hairpin Vs. Intermolecular Architecture Comparison (FIG. 3): Primer Sequences

6:
(SEQ ID NO: 4)
GCT GAC TAC AGA GTG GGA TG

7:
(SEQ ID NO: 5)
GCA GTA CCA ACC CTG TAC AC

Sequences for Intermolecular Architecture

4a:
(SEQ ID NO: 6)
GCA GTA CCA ACC CTG TAC ACC ATC TCA AGT TCT ATG

5a:
(SEQ ID NO: 7)
GCT GAC TAC AGA GTG GGA TGC ATA GAA CTT
(10 bp duplex)

5b:
(SEQ ID NO: 8)
GCT GAC TAC AGA GTG GGA TGC ATA GAA C
(8 bp duplex)

Sequences for Intramolecular Architecture

8a:
(SEQ ID NO: 9)
GCA GTA CCA ACC CTG TAC ACC ATC TCA AGT TCT ATG
GCT GAC TAC AGA GTG GGA TGC ATA GAA CTT
(10 bp duplex)

8b:
(SEQ ID NO: 10)
GCA GTA CCA ACC CTG TAC ACC ATC TCA AGT TCT ATG
GCT GAC TAC AGA GTG GGA TGC ATA GAA C
(8 bp duplex)

-continued

```
8c:
                                          (SEQ ID NO: 11)
GCA GTA CCA ACC CTG TAC ACC ATC TCA AGT TCT ATG
GCT GAC TAC AGA GTG GGA TGC ATA GA (6 bp duplex)
```

qPCR:

The appropriate hairpin 8 (625 pM) or a 1:1 mixture of 4a and 5 for the intermolecular cases (625 pM each) were subjected to qPCR under the standard conditions. PAGE: The appropriate hairpin 8 or a 1:1 mixture of 4a and 5 for the intermolecular cases were subjected to 25 cycles of PCR under the standard conditions. The reactions were analyzed by PAGE (10% TBE gel, 200 V, 20 minutes).

Non-Natural Linker Experiments: Oligo-Ethylene Glycol (FIG. 4)

Primer Sequences

```
S1:
                              (SEQ ID NO: 12)
GCA GTA CCA ACC CTG TAC AC

S2:
                              (SEQ ID NO: 13)
CCT GAC TAC AGA GTG GGA TG
```

Sequences for Intermolecular Architecture

```
4a:
                                          (SEQ ID NO: 14)
GCA GTA CCA ACC CTG TAC ACC ATC TCA AGT TCT ATG

10a:
                                          (SEQ ID NO: 15)
CCT GAC TAC AGA GTG GGA TGC ATA GAA C
(8 bp duplex)

S3:
                                          (SEQ ID NO: 16)
CCT GAC TAC AGA GTG GGA TGC ATA GAA TT
(10 bp duplex)
```

Sequences for Hairpin Architecture (s9=Spacer Phosphoramidite 9, Glen Research)

```
S4:
                                          (SEQ ID NO: 17)
GCA GTA CCA ACC CTG TAC ACC ATC TCA AGT TCT ATG s9
CCT GAC TAC AGA GTG GGA TGC ATA GAA CTT
(10 bp hairpin)

9a:
                                          (SEQ ID NO: 18)
GCA GTA CCA ACC CTG TAC ACC ATC TCA AGT TCT ATG s9
CCT GAC TAC AGA GTG GGA TGC ATA GAA C
(8 bp hairpin)

S5:
                                          (SEQ ID NO: 19)
GCA GTA CCA ACC CTG TAC ACC ATC TCA AGT TCT ATG s9
CCT GAC TAC AGA GTG GGA TGC ATA GA (6 bp hairpin)
```

Optimization of Stem Length

Figure 8:
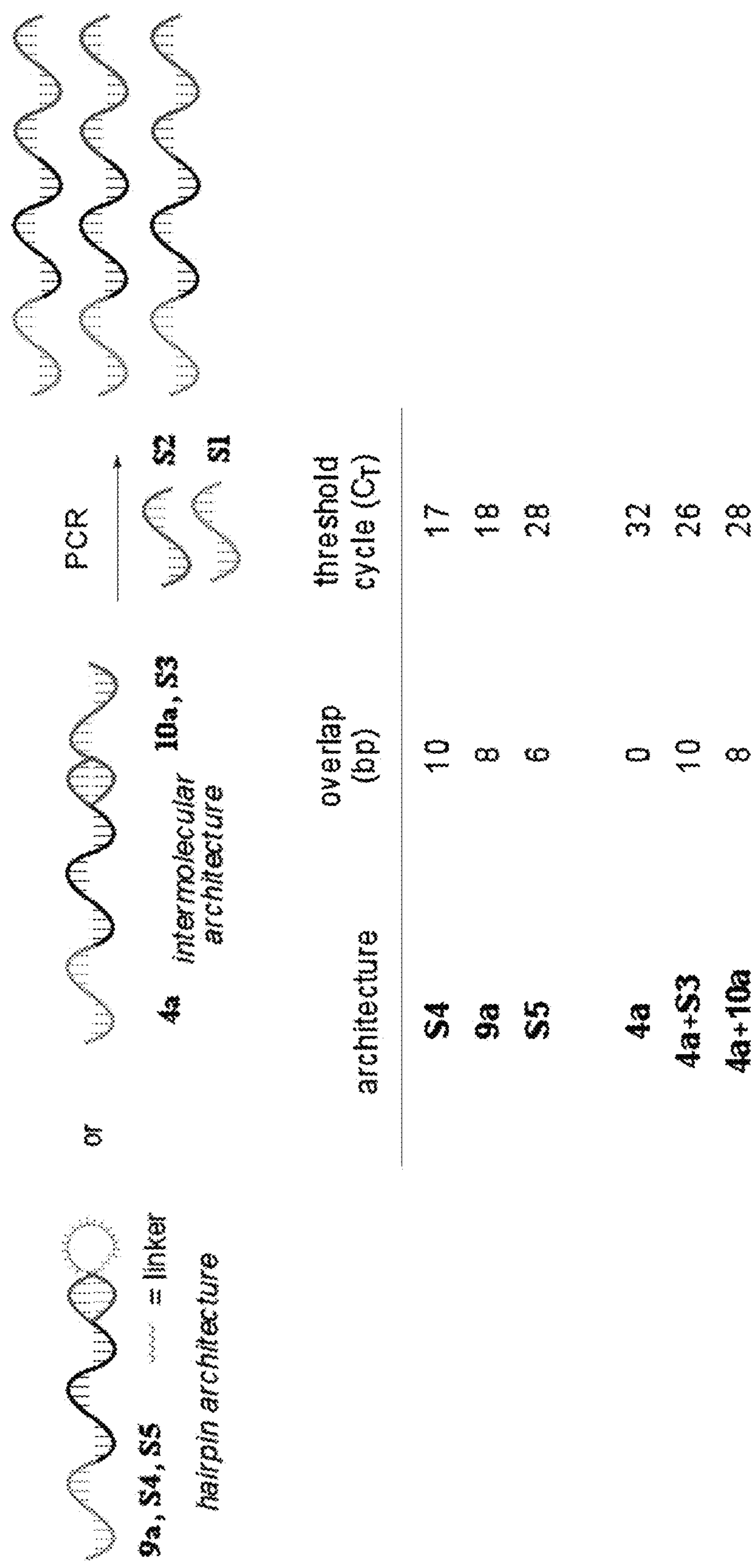
FIG. 8. Optimization of stem length.

The appropriate hairpin was subjected to qPCR under the standard conditions. The substrates with 10- and 8-bp stems were amplified to threshold detection levels in 17-18 cycles, while the 6-bp stem was far less efficient in initiating PCR (FIG. 8).

qPCR Standard Curve

Figure 9:
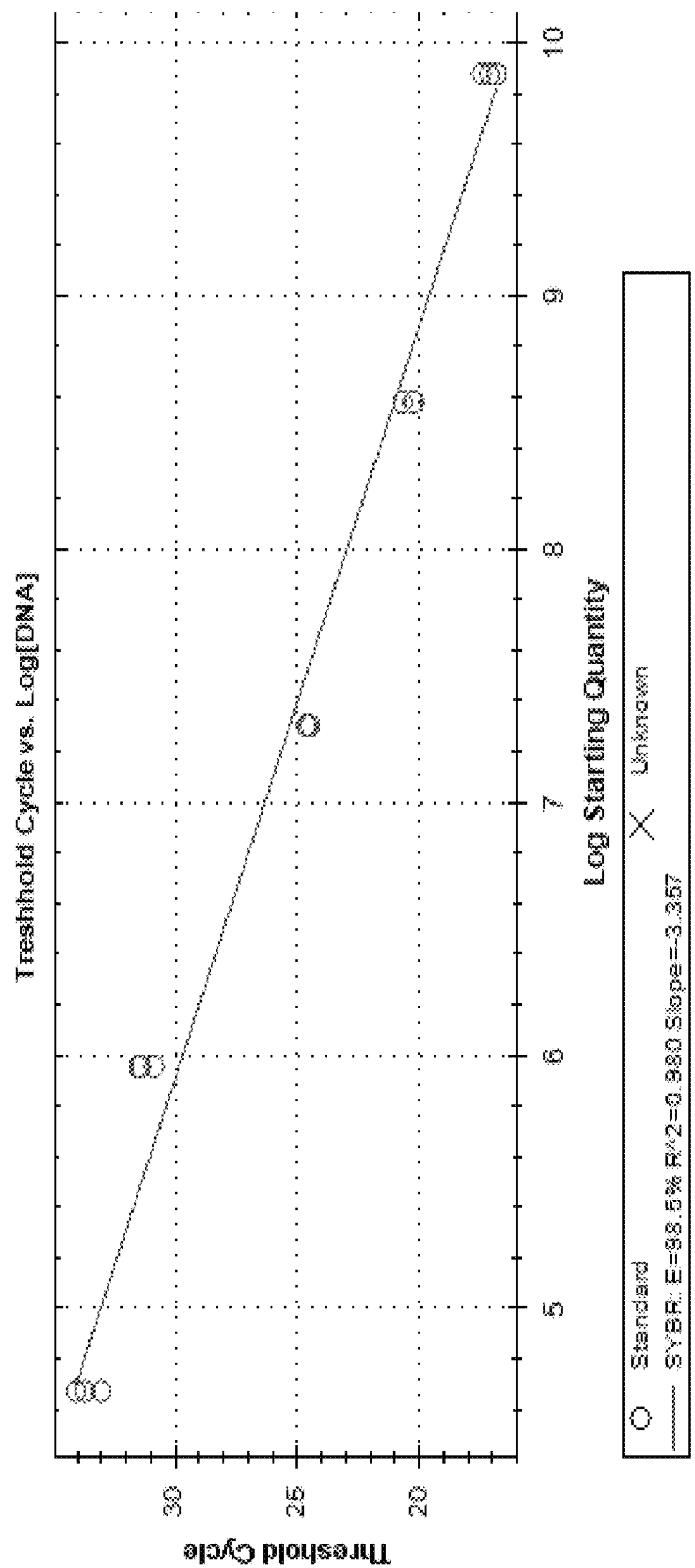
FIG. 9. Cycle Threshold (CT) is linearly correlated to initial log [9a].

To verify that the hairpin structures were well-behaved PCR templates over a range of concentrations, a standard curve was generated by qPCR. Five different concentrations of hairpin 9a (625 pM, 31 pM, 1.6 pM, 80 aM, 4 aM) were subjected to qPCR under the standard conditions, except that a 64° C. annealing step was used instead of 58° C. The log of starting copy number was plotted vs. threshold cycle, and a linear function was fit to the data (FIG. 9).

Non-Natural Linker Experiments: Disulfide (FIG. 4)

Sequences amine=Amino-Modifier Serinol Phosphoramidite;
3'thiol=3'-Thiol-Modifier C6 S-S CPG;
5'thiol=Thiol-Modifier C6 S-S

```
S6:
                                              (SEQ ID NO: 20)
GAG CTC GTT GAT ATC CGC AGA CAT GAG CCC CAC TAC ACA
CAC C (amine)(3' thiol)

S7:
                                              (SEQ ID NO: 21)
(5'thiol)(amine)ACC TAA AGC TAG CAG CTG GCC GTG ATC
AGC TTG GTG TGT G
```

Synthesis of 9b

Figure 10:
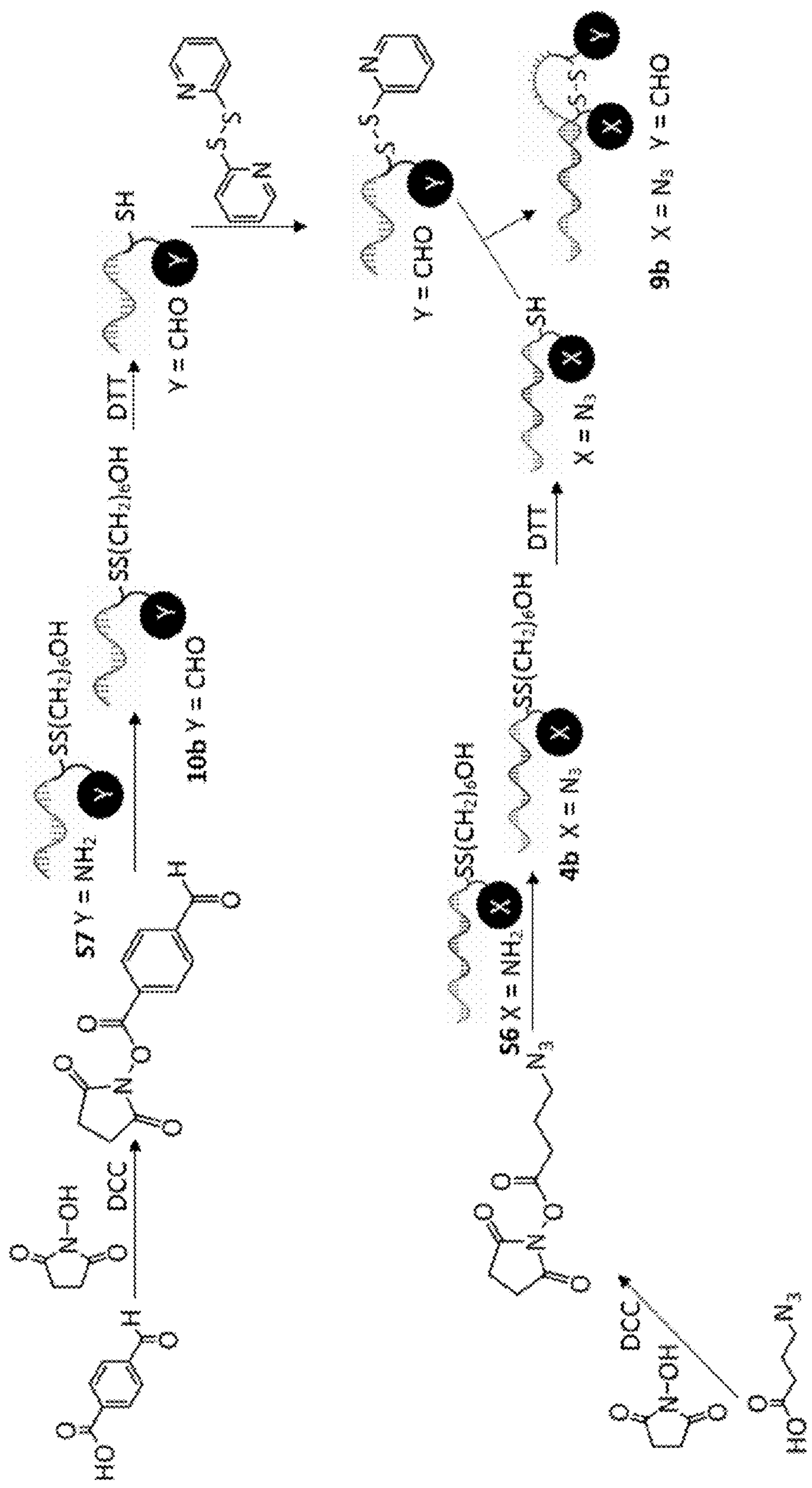
FIG. 10. Synthesis of 9b, a substrate containing an azide and an aldehyde reactive moiety.

The disulfide 9b was synthesized using the route shown in FIG. 10. S6 and S7 were first functionalized with small-molecule carboxylic acid derivatives, providing 4b and 10b. A mixed disulfide was then generated from 10b, which was reacted with the free thiol analog of 4b to yield 9b.

Acylation of S6 and S7

The appropriate carboxylic acid (0.1 mmol) and N-hydroxyl-succinimide (0.1 mmol) were dissolved in 0.1 mL DMF in a 1.5 mL eppendorf tube. N,N'-dicyclohexylcarbodiimide (DCC) (0.1 mmol) was added, and the resulting mixture was agitated at room temperature for 30 minutes. During this time, a white precipitate formed. The reaction was briefly centrifuged, and 0.05 mL of the supernatant was added to a solution of S6 or S7 (10 nmol) in 0.1 mL of 0.2 M phosphate buffer (pH 8) in a separate eppendorf tube. The resulting solution was vigorously agitated for 6 hours, and then diluted (0.5 mL total volume) prior to purification by Nap5 column. The recovered DNA was further purified by HPLC, typically yielding 1-2 nmol of the desired product (10b or 4b). 4-azidobutyric acid (Kanan, M. W.; Rozenman, M. M.; Sakurai, K.; Snyder, T. M.; Liu, D. R. *Nature* 2004, 431, 545) was coupled to S6 to give 4b. 4-formylbenzoic acid was coupled to S7 to give 10b.

Ligation of 4b and 10b

A solution of 4b (500 pmol) and DL-dithiothreitol (DTT, 0.3 M) in 0.1 mL of HEPES buffer (0.1 M, pH 8.5) was agitated for 30 minutes in a 1.5 mL eppendorf tube. A second solution with 10b (instead of 4b) was treated equivalently. The deprotected, thiol-containing DNA was precipitated with ethanol from each reaction. The residue containing 10b was taken up in 0.1 mL of 9:1 50 mM TrisHCl (pH 7.5):ethanol containing 10 mM 2,2'-dipyridyl disulfide. The resulting suspension was agitated for 1 hour, and the DNA was then recovered by ethanol precipitation. The activated residue containing 10b and the residue containing 4b were separately dissolved in 10 μL of 50 mM TrisHCl (pH 7.5), and the concentration of DNA in each solution was determined. An equimolar quantity of the 4b solution was added to the solution of 10b (the total volume did not exceed 20 μL), and the resulting solution was agitated at 4° C. for 12 hours. The DNA was precipitated with ethanol, and the desired product (9b) was isolated by gel purification (3% Ambion Agarose-HR gel). Typically, 100 pmol of disulfide 9b was obtained.

qPCR Analysis
Primer Sequences

```
S8:
                                  (SEQ ID NO: 22)
GAG CTC GTT GAT ATC CGC AG

S9:
                                  (SEQ ID NO: 23)
ACC TAA AGC TAG CAG CTG GC
```

Figure 11:
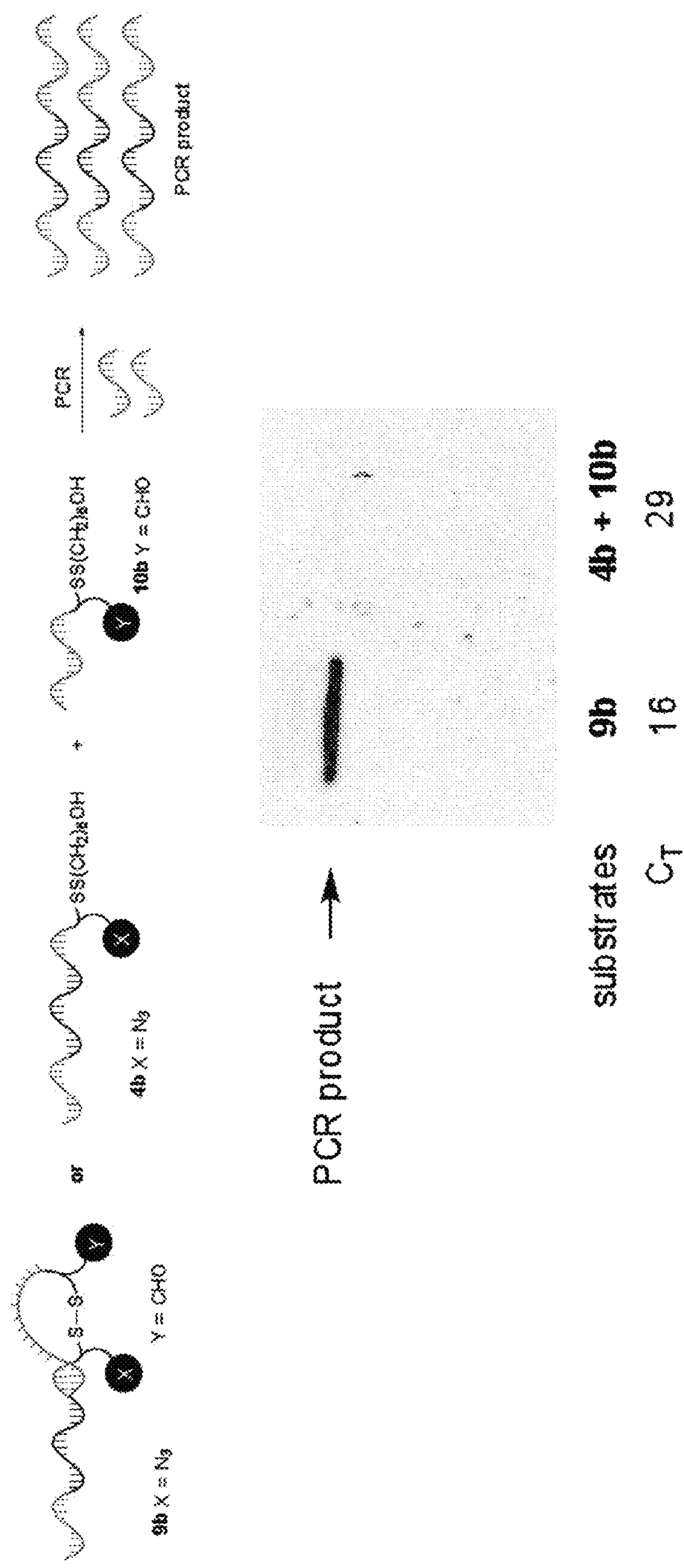
FIG. 11. Disulfide-linked hairpin supports self-priming PCR. PCR conditions: 500 pM 9b or 500 pM 4b and 500 pM 10b, 20 cycles.

The hairpin 9b (500 pM) or a 1:1 mixture of 4b and 10b (500 pM each) for the intermolecular case was subjected to qPCR under the standard conditions. PAGE analysis: The appropriate hairpin 9b (500 pM) or a 1:1 mixture of 4b and 10b for the intermolecular case was subjected to 20 cycles of PCR under the standard conditions. The reactions were analyzed by PAGE (10% TBE gel, 200 V, 20 minutes) (FIG. 11).

Non-Natural Linker Experiments: Amide (FIG. 4)

Sequences $NH_2$=3' amino modifier C7 CPG, $CO_2H$=5' carboxy modifier C10

4c.
(SEQ ID NO: 24)
GCA GTA CCA ACC CTG TAC ACC ATC TCA AGT TCT ATG-$NH_2$ 10c.
(SEQ ID NO: 25)
$CO_2H$-CTG AGC TCG TTG ATA TCC GCA GCA TAG AAC

Formation of 9c from 4c and 10c

To a 45 μL solution of 4c (2.5 pmol) and 10c (3.75 pmol) in 8:1 MOPS buffer (100 mM MOPS, 1 M NaCl, pH 7.5):$CH_3CN$ was added 5 μL of a 0.14 mg/μL solution of DMTMM in MOPS buffer. The resulting solution (50 μL total volume, 9:1 MOPS:$CH_3CN$) was briefly vortexed and then left at 4° C. for 14 hours. The reaction was allowed to warm to room temperature and diluted with 50 μL of 0.1M aqueous NaCl. The DNA was precipitated with ethanol prior to subsequent analysis. Control experiments were performed analogously, but with omission of DMT-MM or with substitution of the amine-terminated DNA (4c) for hydroxyl-terminated DNA (4a).

qPCR Analysis

Primer sequences

```
S1:
                                  (SEQ ID NO: 26)
GCA GTA CCA ACC CTG TAC AC

S10:
                                  (SEQ ID NO: 27)
CTG AGC TCG TTG ATA TCC GCA G
```

DNA from the acylation reaction (9c) was subjected to qPCR under the standard conditions. DNA from control reactions was identically treated. A dramatic dependence of CT upon addition of DMTMM was observed, consistent with acylation and subsequent intramolecular priming through the amide linker (FIG. 12). Upon replacement of amine-modified DNA 4c with unmodified, 3'-OH 4a, DMTMM did not influence PCR efficiency (FIG. 12).

Optimization of DNA-Templated Amide Bond Formation.

Experiments with fluorescently-tagged, amine-modified DNA enabled direct determination of conversion from amine-DNA to carboxylate-ligated DNA.

Sequences

Cy3=Cy3 Phosphoramidite (Glen Research)

S11:
(SEQ ID NO: 28)
Cy3-GCA GTA CCA ACC CTG TAC ACC ATC TCA AGT TCT ATC-$NH_2$

S12:
(SEQ ID NO: 29)
$CO_2H$-CCT GAC TAC AGA GTG GGA TGC ATA GAA C

S13:
(SEQ ID NO: 30)
$CO_2H$-CCT GAC TAC AGA GTG GGA TGT TGA CCG T

DMT-MM-Mediated Coupling of S11 and S12

To a 90 μL solution of S11 (5.0 pmol) and S12 (7.5 pmol) in 8:1 MOPS buffer (100 mM MOPS, 1 M NaCl, pH 7.5):$CH_3CN$ was added 10 μL of a 0.14 mg/μL solution of DMT-MM in MOPS buffer. The resulting solution (100 μL total volume, 9:1 MOPS:$CH_3CN$) was briefly vortexed and then left at the appropriate temperature (see conditions, FIG. 13) for 14 hours. The DNA was precipitated with ethanol prior to subsequent analysis.

sNHS/EDC-Mediated Coupling of S11 and S12

A 90 μL solution of S11 (5.0 pmol) and S12 (7.5 pmol) in 8:1 MES buffer (100 mM MES, 1 M NaCl, pH 6.0):$CH_3CN$ was added to 0.3 mg of sNHS in a 1.5 mL eppendorf tube. 10 μL of a 0.04 mg/μL solution of EDC in MES buffer was then added. The resulting solution (100 μL total volume, 9:1 MES:$CH_3CN$) was briefly vortexed and then left at the appropriate temperature for 14 hours. The DNA was precipitated with ethanol prior to subsequent analysis.

PAGE Analysis of Acylation Reactions

Figure 13:
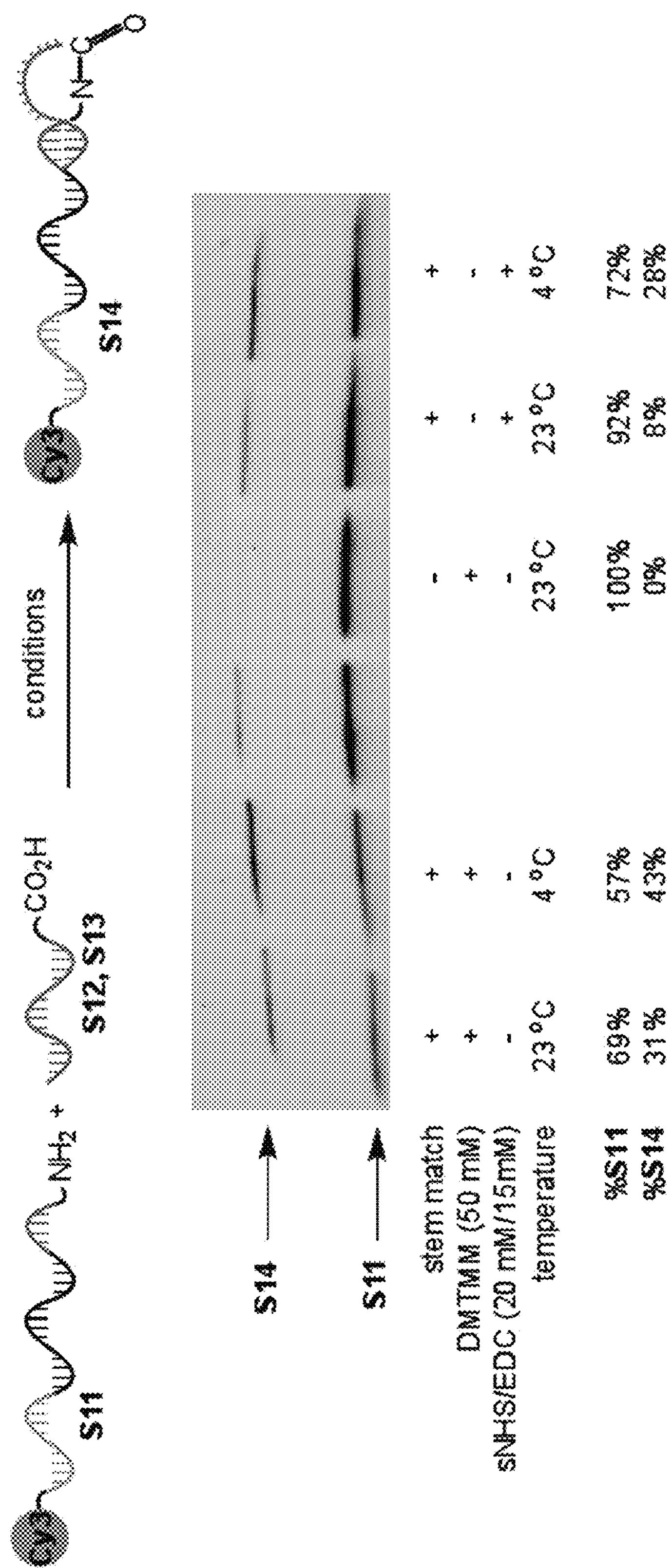
FIG. 13. Fluorescence quantitation of the DNA-templated acylation reaction.

Denaturing PAGE (15% TBE-urea gel, 300 V, 25 minutes) and subsequent fluorescence quantitation was used to monitor the acylation reactions. Regardless of the acylation reagent employed, amide bond formation was markedly more efficient at 4° C. compared with the room temperature reactions (FIG. 13, lanes 1 vs. 2, 5 vs. 6). This result was consistent with our expectation that the melting temperature of the 8 bp intermolecular duplex is ~10° C., and therefore lower temperature provides higher reactivity by stabilizing the duplex intermediate. Furthermore, an experiment with a mismatched stem sequence (S11+S13), such that no intermolecular hybridization is possible, resulted in no amide product, demonstrating that DNA hybridization is essential to the reaction under our experimental conditions (FIG. 13, lane 4).

Library-Format Experiments (FIG. 5)

Sequences:

Stem-forming nucleotides are in bold, point mutations are italicized, and the HindIII recognition site is underlined.

```
6:
                                  (SEQ ID NO: 31)
GCT GAC TAC AGA GTG GGA TG

S10:
                                  (SEQ ID NO: 32)
CTG AGC TCG TTG ATA TCC GCA G
```

Sequences for Intermolecular Architecture

12:
(SEQ ID NO: 33)
GCT GAC TAC AGA GTG GGA TGA ATC TTC ATC TCA AGT

-continued

TCT ATG

13:

(SEQ ID NO: 34)

CTG AGC TCG TTG ATA TCC GCA GCA TAG AAC

Sequences for Intramolecular Architecture

11:

(SEQ ID NO: 35)

GCT GAC TAC AGA GTG GGA TGA *AGC* TTC ATC TCA AGT TCT ATG-spacer9-CTG AGC TCG TTG ATA TCC GCA GCA TAG AAC

Restriction Digestion Experiments

PCR reactions (60 μL total volume) were performed with constant concentrations of 12 and 13 (625 pM) but varying concentrations of 11 (62.5 pM, 6.25 pM, 0.625 pM, 0.0625 pM). The appropriate cycle number for each reaction was determined by prior qPCR evaluation, such that each reaction proceeded while exponential amplification was occurring, but not beyond, in order to minimize dynamic compression. Following PCR, each reaction was split into two aliquots (40 and 20 μL, respectively). To the larger aliquot was added 1 μL of HindIII in glycerol (10,000 units/mL). The resulting solution was incubated at 37° C. for 1 h, and then heated to 65° C. for 20 minutes to deactivate the enzyme. The other aliquot was treated equivalently, but with omission of HindIII. The resulting samples were analyzed by PAGE (10% TBE, 175 V, 25 minutes).

Library-Format PvuII Experiments

A parallel set of experiments were carried out to corroborate the HindIII digestion results. All sequences and procedures were identical to the HindIII experiments, except for those noted below. A double point mutation was used to distinguish the intermolecular and intramolecular substrates to take into account the lower sequence fidelity of PvuII.

Sequences

Sequences for Intermolecular Architecture

S15:

(SEQ ID NO: 36)

GCT GAC TAC AGA GTG GGA TGC *AAG* TGC ATC TCA AGT TCT ATG

Sequences for Intramolecular Architecture

S16:

(SEQ ID NO: 37)

GCT GAC TAC AGA GTG GGA TGC *AGC* TGC ATC TCA AGT TCT ATG-spacer9-CTG AGC TCG TTG ATA TCC GCA GCA TAG AAC

Figure 14:
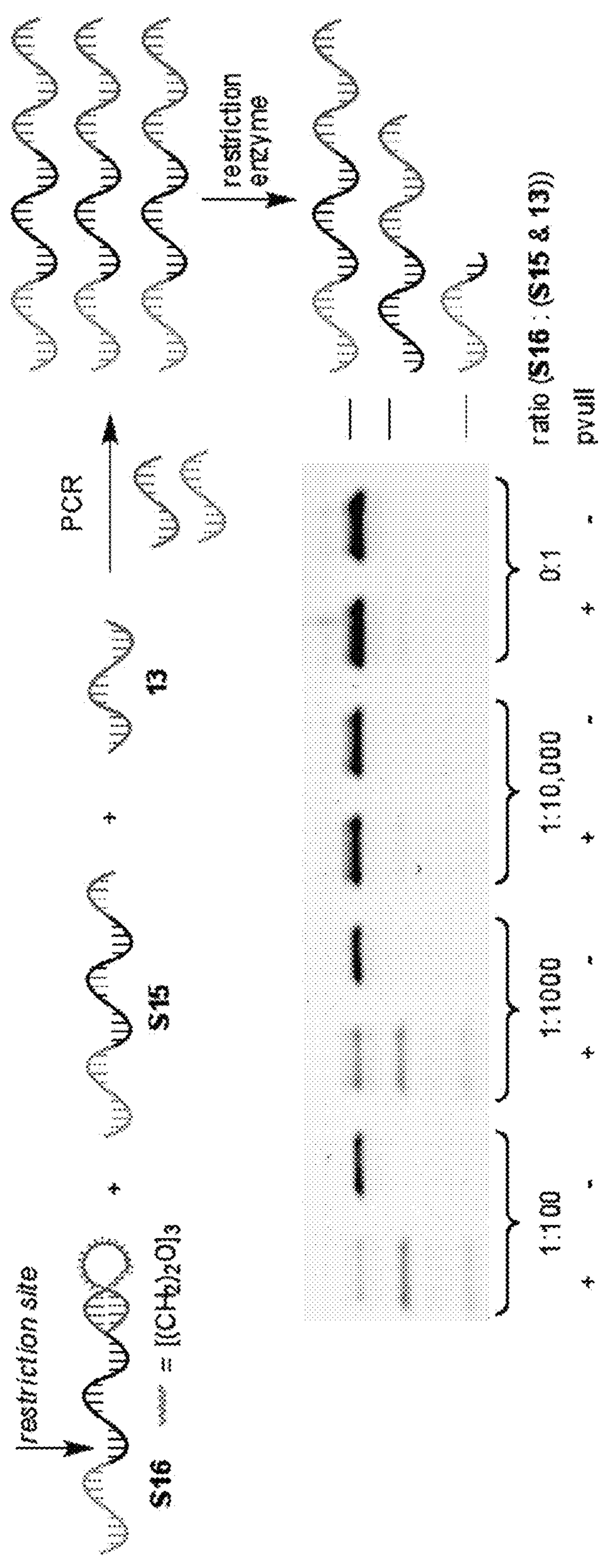
FIG. 14. Library-format experiment with PvuII.
Figure 15:
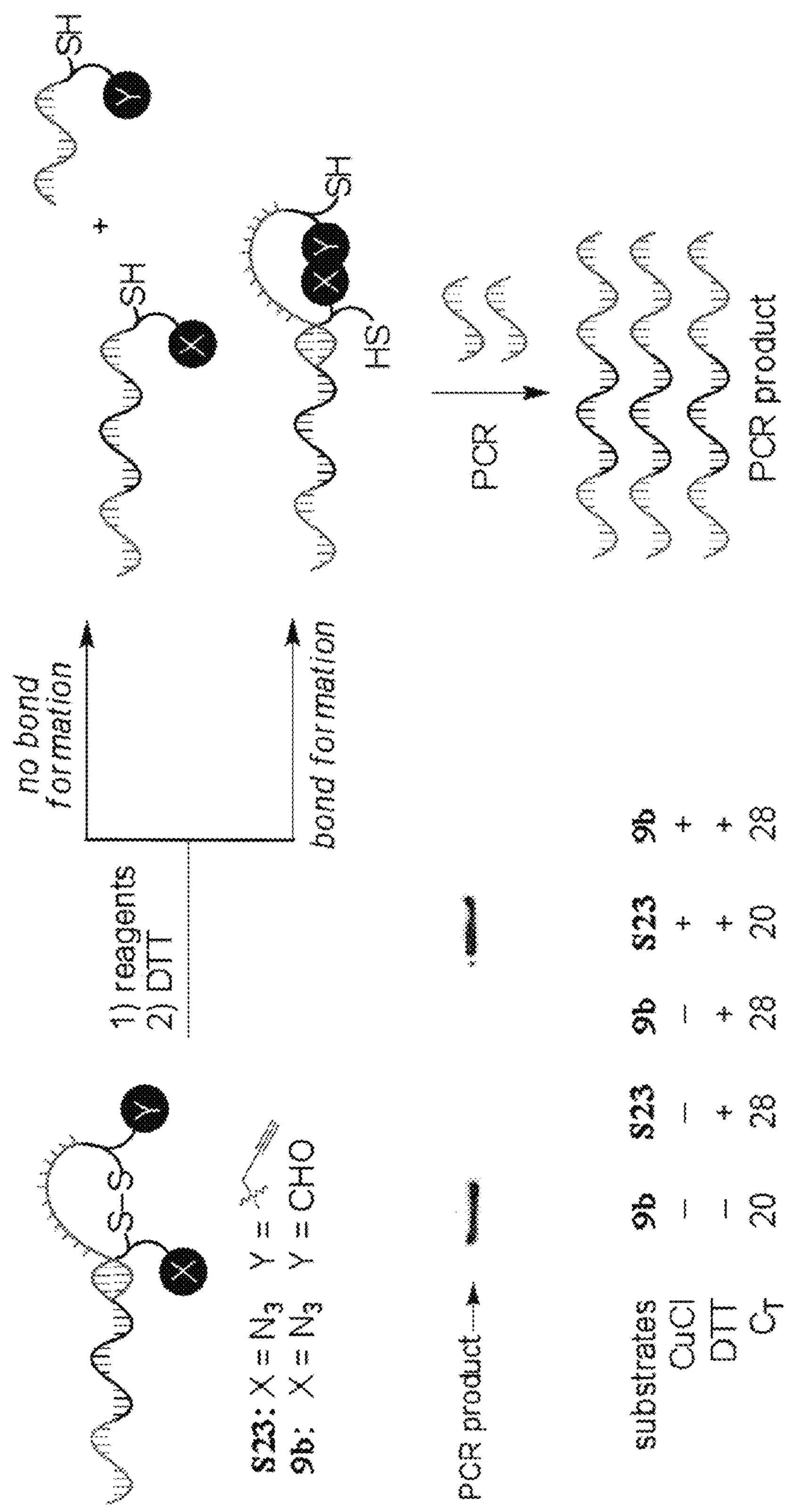
FIG. 15. RD-PCR-based DNA-encoded reaction discovery selection validation using a copper-catalyzed Huisgen cycloaddition reaction. PCR conditions: 5 pM template, 24 cycles.

Restriction digestion of the PCR reactions was carried out with 1 μL of PvuII-HF (10,000 units/mL stock in glycerol). Heat inactivation was achieved by incubation at 80° C. for 20 minutes following the 1 h incubation at 37° C. Reactions were analyzed as described above (FIG. 14).

Reaction Discovery Model System (FIG. 6)

Sequences

Amine=Amino-Modifier Serinol Phosphoramidite; 3'thiol=3'-Thiol-Modifier C6 S-S CPG; 5'thiol=Thiol-Modifier C6 S-S

S17:

(SEQ ID NO: 38)

GAG CTC GTT GAT ATC CGC AGA GCG TTA TGG TCC GAC ACA CAC C (amine)(3'thiol)

S18:

(SEQ ID NO: 39)

(5'thiol)(amine)ACC TAA AGC TAG CAG CTG GCG AGG TTC CAG ATG GTG TGT G

S19:

(SEQ ID NO: 40)

(5'thiol)(amine)ACC TAA AGC TAG CAG CTG GCC GCA CAC TTT CTG GTG TGT G

The free amine of each substrate above was coupled to a small-molecule carboxylic acid derivative as described earlier. For the reactions with 6-heptenoic acid and 10-undecynoic acid, the active ester was formed in 0.15 mL DMF, and 0.1 mL of the resulting soluble fraction was added to the DNA-$NH_2$, giving a total volume of 0.2 mL. This modification led to increased yields, presumably due to greater solubility of the hydrophobic carboxylic acids in DMF.

6-heptenoic acid was coupled to S17 to give S20.

4-iodophenylacetic acid was coupled to S18 to give S21.

10-undecynoic acid was coupled to S19 to give S22.

Three substrates were made by formation of a disulfide bond:

4b was coupled to 10b to give 9b.

S20 was coupled to S21 to give 9d.

4b was coupled to S22 to give S23.

Reaction of Disulfide-Linked DNA with Pd 5 pmol of the substrate oligo (9b or 9d) was added to 0.1 mL of a 1 mM disodium tetrachloropalladate solution in MOPS buffer (50 mM MOPS, 0.5 M NaCl, pH 7.5). The resulting solution was heated at 65° C. for 30 minutes. The DNA was recovered by ethanol precipitation, and then taken up in 0.1 mL of a 0.3 M DTT solution in HEPES buffer (0.1 M HEPES, pH 8.5). The reaction was left for 1 hour at 65° C. to ensure full cleavage of the disulfide bond, and the DNA was then recovered by ethanol precipitation. qPCR of Pd-treated DNA Primer Sequences

S8:

(SEQ ID NO: 41)

GAG CTC GTT GAT ATC CGC AG

S9:

(SEQ ID NO: 42)

ACC TAA AGC TAG CAG CTG GC

DNA recovered from the Pd reactions and various controls was subjected to qPCR under slightly modified conditions. The starting concentration of DNA was 50 pM.

PAGE Analysis

DNA recovered from the Pd reactions and various controls was subjected to 23 cycles of PCR under slightly modified conditions. The starting concentration of DNA was 50 pM. The reactions were analyzed by PAGE (10% TBE gel, 200 V, 20 minutes).

Detection of Cu(I)-Catalyzed Huisgen Cycloaddition**

1 pmol of the substrate oligo (9b or S23) was added to 0.1 mL of a 9:1 $H_2O$:$CH_3CN$ solution containing 2 mM Cu(I)Cl. After 30 minutes at room temperature, the reactions were subjected to ethanol precipitation. The DNA pellet was taken up in 0.1 mL of 0.3 M DTT in HEPES buffer (0.1 M HEPES, pH 8.5) and heated for 1 hour at 65° C. to ensure full cleavage of the disulfide bond. The DNA was then recovered by ethanol precipitation.

(**a) Himo, F.; Loveli, T.; Hilgraf, R.; Rostovtsev, V. V.; Noodleman, L.; Sharpless, K. B.; Fokin, V. V. *J. Am. Chem. Soc.* 2005, 127, 210. For validation of DNA-encoded reaction discovery with this reaction, see Kanan, M. W.; Rozenman, M. M.; Sakurai, K.; Snyder, T. M.; Liu, D. R. *Nature* 2004, 431, 545.)

qPCR of Cu-Treated DNA

Primer Sequences

```
S8:
                                  (SEQ ID NO: 43)
GAG CTC GTT GAT ATC CGC AG

S9:
                                  (SEQ ID NO: 44)
ACC TAA AGC TAG CAG CTG GC
```

DNA recovered from the Cu reactions and various controls was subjected to qPCR under slightly modified conditions. The starting concentration of DNA was 5 pM. PAGE Analysis DNA recovered from the Cu reactions and various controls was subjected to 24 cycles of PCR under slightly modified conditions. The starting concentration of DNA was 5 pM. The reactions were analyzed by PAGE (10% TBE gel, 200 V, 20 minutes).

Protease Activity Detection Model System (FIG. 7)

Primers

```
S1:
                                  (SEQ ID NO: 45)
GCA GTA CCA ACC CTG TAC AC

S10:
                                  (SEQ ID NO: 46)
CTG AGC TCG TTG ATA TCC GCA G
```

Sequences

3a=3'amino modifier C7 CPG

DNA-peptide 17.
GCA GTA CCA ACC CTG TAC ACC ATC TCA AGT TCT ATG-3a-Ala-Pro-Gly-Phe-Ala-NHAc (nucleic acid sequence: SEQ ID NO: 47; amino acid sequence: SEQ ID NO: 48)

Carboxylate 10c:
(SEQ ID NO: 49)
$CO_2H$-CTG AGC TCG TTG ATA TCC GCA GCA TAG AAC

Synthesis of DNA-Peptide Conjugate 17

Compound 17 was synthesized by solid-phase co-synthesis. 0.2 μmol of 3' amino modifier C7 CPG was subjected to solid-phase peptide synthesis to install the pentapeptide on the Fmoc-amine group. The peptide synthesis included iterated rounds of Fmoc deprotection (20% pipiridine/NMP), coupling (Fmoc-amino acid/HATU/DIPEA/NMP), and capping (5% acetic anhydride and 6% 2,6-lutidine in NMP).

The CPG was then subjected to standard solid-phase DNA synthesis to install the oligonucleotide at the site of the DMT-protected hydroxyl group. The substrate was cleaved from the resin by standard methods (NH4OH/methylamine). The 5'-DMT-protected DNA was then purified by HPLC. Following lyophilization and deprotection of the DMT group by standard methods (3% TFA), the DNA was repurified by HPLC to yield 17 (26.6 nmols).

DNA Detection of Bond Cleavage by Subtilisin A

DNA-peptide 17 (2.6 pmol/uL) was treated with subtilisin A (65 ng/uL) in PBS buffer (subsequent experiments demonstrated that lower concentrations (to 650 pg/uL)). of subtilisin A were sufficient to affect bond cleavage under otherwise identical conditions). After incubation at 37° C. for 90 minutes, the DNA and enzyme were separated by phenol/chloroform extraction. The DNA was recovered by ethanol precipitation, and taken up in the appropriate buffer (MOPS or MES) for acylation with 10c under the conditions described earlier. Quantitative PCR and PCR/PAGE analysis were performed as described earlier.

TABLE 1

LCMS characterization of functionalized oligonucleotides

| Compound | observed ion's charge | Expected m/z | Observed m/z |
|---|---|---|---|
| 9c (3'-NH2) | −6 | 1854.504 | 1854.484 |
| 10c (5'-CO2H) | −5 | 1899.930 | 1899.963 |
| 17 (DNA-peptide) | −7 | 1658.732 | 1658.683 |
| 4b (3'SSR) | −6 | 2290.563 | 2290.628 |
| 10b (5'SSR) | −6 | 2174.367 | 2174.353 |
| S20 | −6 | 2307.401 | 2307.337 |
| S21 | −5 | 2641.629 | 2641.669 |
| S22 | −6 | 2166.382 | 2166.339 |

REFERENCES

1. Seminal reports:

a. Tuerk C.; Gold L. Science 1990, 249, 505.

b. Ellington A. D.; Szostak J. W. Nature 1990, 346, 818.

c. Robertson D. L.; Joyce G. F. Nature 1990, 344, 467.

For a general review, see:

d. Wilson D. S.; Szostak J. W. Annu. Rev. Biochem. 1999, 68, 611.

2. Recent reviews of evolved DNA/RNA aptamers:

a. Shamah S. M.; Healy J. M.; Cload S. T. Acc. Chem. Res. 2008, 41, 130.

b. Gopinath S. H. B. Anal. Bioanal. Chem. 2007, 387, 171.

3. In vitro selections of DNA-linked small molecules:

a. Wrenn S. J.; Weisinger R. M.; Halpin D. R.; Harbury P. B. J. Am. Chem. Soc. 2007, 129, 13137.

b. Melkko S.; Zhang Y.; Dumelin C. E.; Scheuermann J.; Neri D. Angew. Chem., Int. Ed. 2007, 46, 4671.

Mock Selections:

c. Doyon J. B.; Snyder T. M.; Liu D. R. J. Am. Chem. Soc. 2003, 125, 12372.

d. Gartner Z. J.; Tse B. N.; Grubina R.; Doyon J. B.; Snyder T. M.; Liu D. R. Science 2004, 305, 1601.

4. a. Silverman S. Chem. Commun. 2008, 3467.

b. Joyce G. F. Annu. Rev. Biochem. 2004, 73, 791.

5. a. Kanan M. W.; Rozenman M. M.; Sakurai K.; Snyder T. M.; Liu D. R. Nature 2004, 431, 545.

b. Rozenman M. M.; Liu D. R. Chem Bio Chem 2006, 7, 253.

c. Rozenman M. M.; Kanan M. W.; Liu D. R. J. Am. Chem. Soc. 2007, 129, 14933.

6. a. Tarasow T. M.; Tarasow S. L.; Eaton B. E. Nature 1997, 389, 54.

b. Seelig B.; Jaschke A. Chem. Biol. 1999, 6, 167.

Other tags may be used. For selected examples, see:

c. Chandra M.; Silverman S. K. J. Am. Chem. Soc. 2008, 130, 2936.

d. Pradeepkumar P. I.; Hobartner C.; Baum D. A.; Silverman S. K. Angew Chem., Int. Ed. 2008, 47, 1753.

e. Johnston W. K.; Unrau P. J.; Lawrence M. S.; Glasner M. E.; Bartel D. P. Science 2001, 292, 1319.

7. a. Breaker R. R.; Joyce G. F. Chem. Biol. 1994, 1, 223.

b. Sheppard T. L.; Ordoukhanian P.; Joyce G. F. Proc. Natl. Acad. Sci. U.S.A. 2000, 97, 7802.

For an alternative approach, see:

c. Hobartner C.; Pradeepkumar P. I.; Silverman S. K. Chem. Commun. 2007, 2255.

8. a. Rozenman M. M.; McNaughton B. R.; Liu D. R. Curr. Opin. Chem. Biol. 2007, 11, 259.

See Also:

b. Wrenn S. J.; Harbury P. B. Annu. Rev. Biochem. 2007, 76, 331.

9. Note that in contrast with a conventional selection in which unfit library members are discarded and sequences encoding surviving members are replicated in a subsequent step, RD-PCR achieves the selective replication of only those sequences encoding desired library members.

10. Ogawa A.; Maeda M. Biorg. Med. Chem. Lett. 2007, 17, 3156.

11. Computation carried out using the Oligonucleotide Modeling Platform (OMP, DNA Software, Inc 12. For examples of phosphodiester bond formation-dependent PCR, see:

a. Bartel D. P.; Szostak J. W. Science 1993, 261, 1411.

b. Makrigiorgos G. M. Human Mut. 2004, 23, 406.

c. Troutt A. B.; McHeyzer-Williams M. G.; Pulendran B.; Nossal G. J. V. Proc. Natl. Acad. Sci. U.S.A. 1992, 89, 9823.

13. For a general review, see: Kubista M.; Andrade J. M.; Bengtsson M.; Forootan A.; Jonák J.; Lind K.; Sindelka R.; Sjöback R.; Sjögreen B.; Strömbom L.; Stœhlberg A.; Zoric N. Mol. Asp. Med. 2006, 27, 95.

14. Gartner Z. J.; Liu D. R. J. Am. Chem. Soc. 2001, 123, 6961.

15. Heck R. F. Org. React. 1982, 27, 345. See also ref 5a.

16. As little as 10 fmol of 9d and 9b could be carried through the process with similar results, suggesting that selections can be performed on a very small scale.

17. For approaches to protease substrate profiling by derivitization of free α-amines, see:

a. Mahrus S.; Trinidad J. C.; Barkan D. T.; Sali A.; Burlingame A. L.; Wells J. A. Cell 2008, 134, 866.

b. McDonald L.; Robertson D. H. L.; Hurst J. L.; Beynon R. J. Nat. Methods 2005, 2, 955.

c. Gevaert K.; Goethals M.; Martens, Van Damme J.; Staes A.; Thomas G. R.; Vandekerckhove J. Nat. Biotechnol. 2003, 21, 566.

18. Substrate designed in consultation with Sigma-Aldrich Protease finder (http://sigma-aldrich.com/proteasefinder).

19. DNA-templated amide bond formation with DMT-MM:

a. Li X. Y.; Gartner Z. J.; Tse B. N.; Liu D. R. J. Am. Chem. Soc. 2004, 126, 5090. With EDC/sNHS:

b. Gartner Z. J.; Kanan M. W.; Liu D. R. Angew. Chem., Int. Ed. 2002, 41, 1796. For a review of DTS, see:

c. Li X. Y.; Liu D. R. Angew. Chem., Int. Ed. 2004, 43, 4848.

Figure 17:
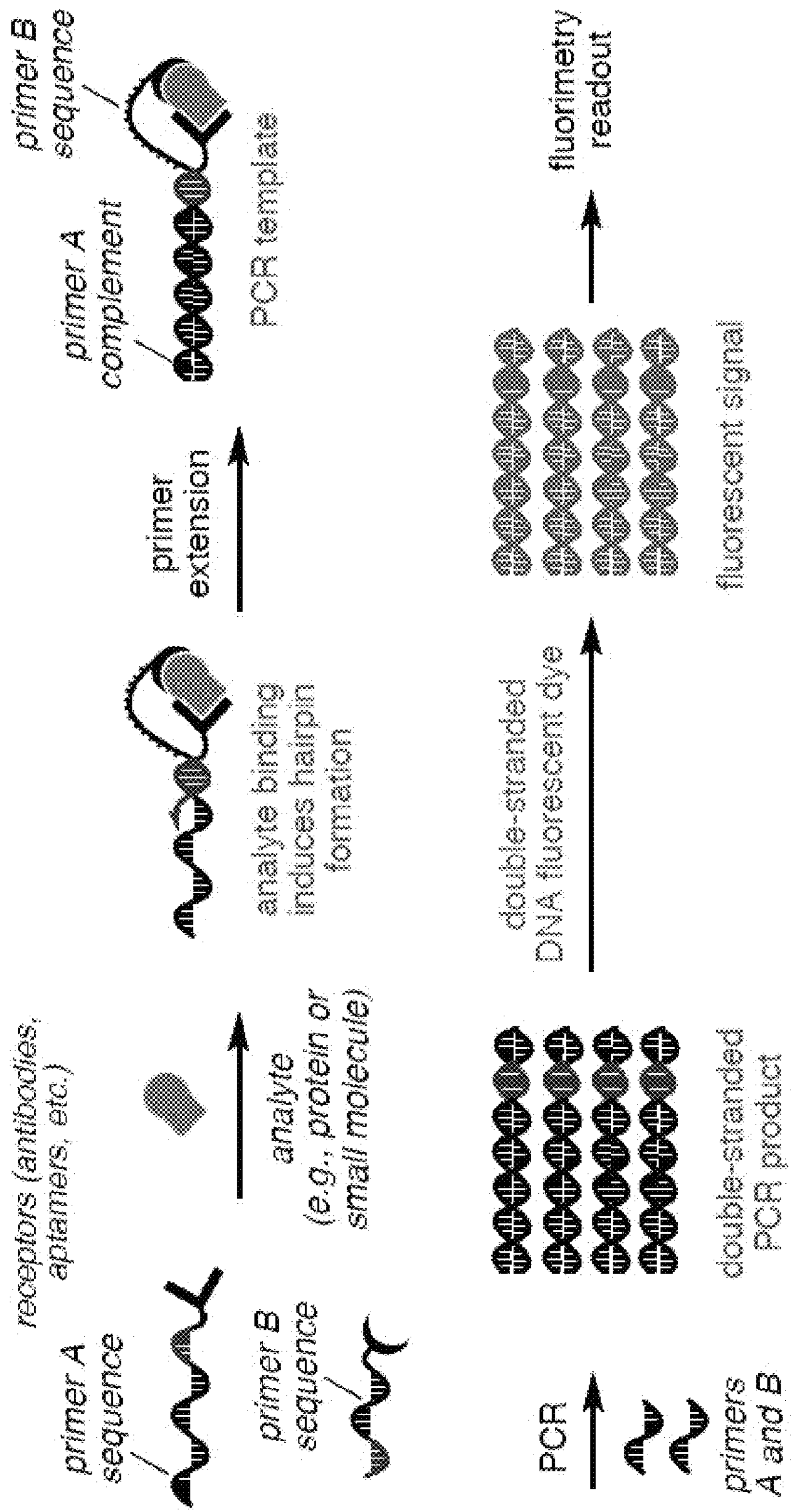
FIG. 17. ID-PCR-based reaction transducing non-covalent binding into a PCR template.

Example 2: Interaction-Dependent PCR: Direct, Solution-Phase In Vitro Selection for Non-Covalent Interaction ID-PCR (FIG. 16) resembles RD-PCR except that non-covalent binding of one or two receptor-linked DNA strands (nucleic acid template and first primer, respectively) to an analyte, rather than the covalent bonding of the two strands, allows primer extension to generate a double-stranded PCR template. Because binding of one or both DNA strands to the analyte is required for intramolecular primer extension to generate a double-stranded PCR template, reactions in the absence of analyte do not result in significant template formation and therefore in minimal PCR amplification. In the presence of the analyte, however, binding of the analyte to the DNA-linked receptors brings the nucleic acid template and the first primer into proximity. As a result, their base pairing takes place, enabling primer extension to generate a double-stranded DNA template (FIG. 17).

Figure 18:
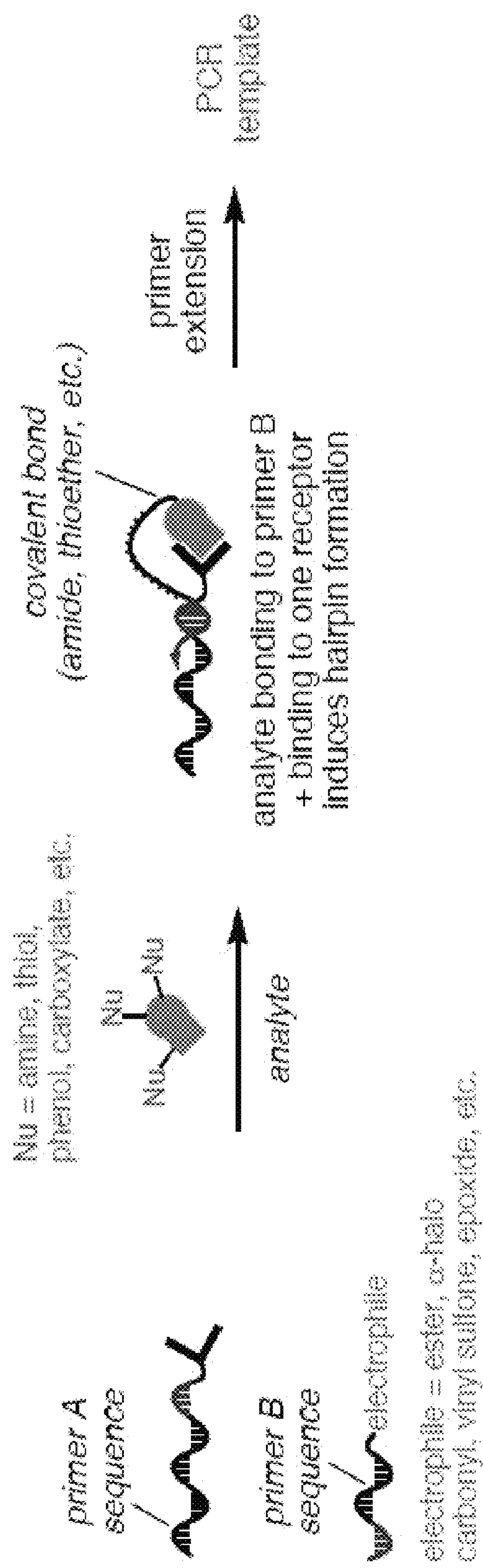
FIG. 18. ID-PCR analyte binding strategy: single-point analyte binding.
Figure 19:
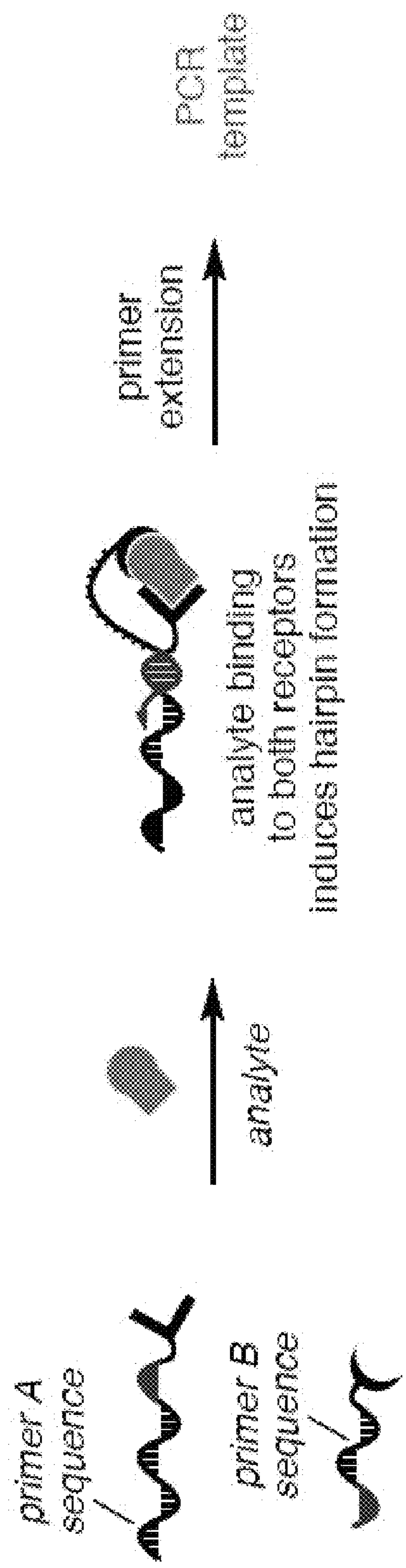
FIG. 19. ID-PCR analyte binding strategy: sandwich binding.

At least two different analyte binding schemes are provided by which ID-PCR transduces the presence of protein or small-molecule analytes into a PCR amplicon: single-point binding (FIG. 18) and sandwich binding (FIG. 19).

In the single-point binding approach, the nucleic acid template is covalently attached to the analyte, and the first primer is linked to an analyte, specific aptamer or antibody receptor (FIG. 18). Aptamers offer distinct advantages over antibodies in that they are evolved by researchers in the laboratory (as opposed to being selected in the immune system of an animal) and thus can be simultaneously evolved positively for binding to a target analyte and negatively against binding to specific false positive molecules. Aptamers are also less “sticky” (hydrophobic) than antibodies and thus may be less prone to non-specific binding. The covalent linkage between the nucleic acid template and a protein analyte can be established using any of several DNA-linked reactive groups including esters and alpha-halo carbonyls that are known to undergo facile reaction with nucleophilic groups at the surface of virtually all proteins. Compared with the sandwich binding method below, this approach offers the advantage that only a single analyte-binding receptor is required. Because the protein will be covalently attached to the nucleic acid template through a variety of regiochemistries and orientations, this approach also maximizes the likelihood that at least one of the protein attachment schemes will allow the key primer extension event that generates the double-stranded PCR template. The single-point binding strategy may not offer maximal sensitivity, however, for this same reason; because the protein is presented to the receptor in a heterogeneous mixture of orientations, some of the bound proteins may not support efficient primer extension. In these cases, a variety of DNA-protein linker lengths and compositions can be tested. The single-point binding approach can further be applied to small-molecule analytes that possess groups that are capable of being attached to DNA-linked nucleophiles or electrophiles.

In the sandwich binding approach, both the nucleic acid template and the first primer are linked to a receptor (for example, an aptamer or antibody) that binds to an analyte. Upon binding of the analyte to both receptors, the intramolecular hairpin is formed and primer hybridization and extension can take place. Compared with the single-point binding strategy, this approach requires a second receptor that is capable of binding the analyte simultaneously with the first receptor, but offers the advantages of (i) not requiring covalent attachment to one of the DNA strands; (ii) not being subject to sensitivity losses that might arise from heterogeneous DNA-bound analyte orientations, (iii) offering greater specificity since both receptors must simultaneously engage the target in order to initiate primer extension and PCR; and (iv) enabling, in principle, a single analyte molecule to give rise to multiple double-stranded PCR template molecules under conditions in which receptor-analyte binding is reversible and occurs concurrently with primer extension.

Importantly, in both approaches the binding affinities required between the receptor(s) and the analyte are lower than those required in traditional intermolecular binding platforms because in both cases the analyte and receptor(s) bind cooperatively. In the first case, receptor-analyte binding and DNA hybridization are cooperative. Our previous studies on DNA-templated synthesis (see Li, X.; Liu, D. R. Angew. Chem. Int. Ed. 43, 4848-4870 (2004) for a review) suggest that this increase in effective molarity can be quite substantial (e.g., ~$10^3$-$10^6$-fold). Likewise, in the sandwich binding mode two receptors can both simultaneously bind the analyte while forming a base-paired complex. As a result, even modest affinity receptors may be suitable for the sensing platform proposed here.

PCR and Readout of PCR Product Formation

Once primer extension generates a viable double-stranded PCR template in an analyte-dependent manner, standard PCR methods are used to exponentially amplify the template into many double-stranded DNA amplicons. PCR amplification is routinely used to amplify small numbers (≤~10,000) of molecules into more than billions of double-stranded copies. Palm-sized, battery powered PCR thermocyclers are commercially available and similar devices have already been integrated into many portable PCR-based nucleic acid sensing devices that are in use in the field. The presence and the abundance of the resulting PCR products can be read out in a portable, field-deployable way by using one of several commercially available double-strand-specific fluorescent DNA-binding dyes and a commercially available, hand-held fluorimeter. Only those PCR reactions in which product is generated will result in an increase in sample fluorescence, and the intensity of this fluorescence should correlate with the amount of starting template and therefore should be a function of the amount of the analyte and the efficiency of the transduction process. Standard curves can be generated for each analyte of interest to establish a relationship between absolute fluorescence intensity and absolute quantity of the analyte entering the ID-PCR process.

Operational Considerations

The ID-PCR-based detection platform described herein offers several potential operation advantages over existing systems. Since, in some embodiments, the analyte binding and primer extension events can take place in the same solution as the subsequent PCR reaction, a single small tube containing buffer, the DNA-linked receptors, primer extension reagents, double-stranded DNA fluorescent dye, and a wax capsule containing PCR reagents (which melts above ~80° C. during the melting step of the first PCR cycle, releasing its content) can be used for the entire assay. This one-pot assay format, featured in some embodiments of the invention, is operationally simple because it would require only that the operator add the analyte to a single tube and place the tube into the thermocycler. Since real-time PCR methods are already widely used have demonstrated the compatibility of double-stranded DNA fluorescent dyes with PCR reactions, some embodiments are envisioned, in which fluorimetry of the sample after PCR takes place in the same tube, and, in certain embodiments, even without moving the tube, for example in embodiments using a fluorimeter that is integrated into the portable device (as it is in a modern real-time PCR instruments). In such streamlined workflow embodiments, the sensing platform requires considerably less sample processing and fewer manipulations than most of the currently used protein and small-molecule sensing platforms. Because the PCR reactions used in some embodiments are not limited to DNA sequences determined by nature but instead amplify DNA sequences chosen by the researcher, their length and sequence can be optimized for rapid and highly efficient PCR amplification. For short sequences with tailor-made primer sequences, PCR amplification can currently be performed in 6 minutes (30 cycles, 6-second thermal ramp times between 95° C. and 70° C., no hold times necessary for short amplicons). If ramp times, which depend on the thermal inertia of the sample and instrument stage, as well as the effectiveness of the heating and cooling process, can be halved by doubling temperature change rates to ~8° C. per second then the PCR step would require only 3 minutes. The fluorescent dye addition and fluorimetry requires only seconds. Likewise, it is envisioned that the primer extension step to create the short double-stranded PCR template requires less than one minute. Thus the entire process from addition of the analyte to the ID-PCR reaction through PCR and fluorescence readout in principle can be accomplished in less than 10 minutes. In some embodiments, a handheld device is employed for thermocycling and fluorescence measurement. In some embodiments, an integrated handheld device is employed for both functions. Handheld, battery powered devices for thermocycling and fluorescence measurement are well known in the art and are commercially available, (see, for example, www.ahrambio.com/product.html and www.turnerbiosystems.com/instruments/PicoFluor-handheld-fluorometer-fluorimeter-DNA-RNA-protein.php).

Although the description of the platform thus far has focused on the detection of a single analyte, because DNA hybridization is sequence-specific and the DNA sequences linked to the receptors are chosen by researchers, it is in principle possible to implement the sensing system in a multiplexed format in which a single tube contains several sets of DNA-linked receptors, each of which bind to a different analyte of interest. In this case the readout system cannot simply rely on the presence of double-stranded DNA produced during PCR but instead must characterize the abundance of different sequences of DNA that are each produced in response to the presence of a different analyte. Several sequence-specific multiplex DNA readout systems are in current use, including Luminex bead-based systems and DNA microarray ("DNA chip")-based systems. These multiplexed DNA readout systems are more complex and more difficult to implement in a portable form; however, if single-sample multiplexing is highly desired, they may serve as a reasonable readout method. Alternatively, the operational simplicity of the sensing platform may make practical a simpler form of multiplexing in which one sample is simply added to several different tubes, each of which detects the presence of a different analyte. The tubes are processed in parallel and the abundance of PCR product is measured in each tube (a process that takes only small numbers of seconds) by fluorimetry.

REFERENCES

1. Jeffreys, A. J., Neumann, R. & Wilson, V. Repeat unit sequence variation in minisatellites: a novel source of DNA polymorphism for studying variation and mutation by single molecule analysis. Cell 60, 473-485 (1990).
2. Agrawal, N., Hassan, Y. A. & Ugaz, V. M. A pocket-sized convective PCR thermocycler. Angew Chem Int Ed Engl 46, 4316-4319, doi:10.1002/anie.200700306 (2007).
3. Joshi, U. M. R., Romi; Sheth, Anil, R.; Shah, Haresh P.; A Simple and Sensitive ColorTest for the Detection of Human Chorionic Gonadotropin. Obstetrics & Gynecology 57, 252-254 (1981).
4. Suebert, P. V., C; Esch, F; Lee, M; Dovey, H; Davis, D; Sinha, S; Schlossmacher, M; Whaley, J; Swindlehurst, C; McCormack, R; Wolfert, R; Selkoe, D; Lieberburg, I; Schenk, D Isolation and Quantification of Soluble Alzheimers Beta-Peptide from Biological Fluids. Nature 359, 325-327 (1992).

5. Vignali, D. A. Multiplexed particle-based flow cytometric assays. J Immunol Methods 243, 243-255 (2000).
6. Hill, H. D. & Mirkin, C. A. The bio-barcode assay for the detection of protein and nucleic acid targets using DTT-induced ligand exchange. Nat Protoc 1, 324-336, doi: 10.1038/nprot.2006.51 (2006).
7. Baker, B. R. et al. An electronic, aptamer-based small-molecule sensor for the rapid, label-free detection of cocaine in adulterated samples and biological fluids. J Am Chem Soc 128, 3138-3139, doi:10.1021/ja056957p (2006).
8. Hill, H. D., Vega, R. A. & Mirkin, C. A. Nonenzymatic detection of bacterial genomic DNA using the bio bar code assay. Anal Chem 79, 9218-9223, doi:10.1021/ac701626y (2007).
9. Sharon, E., Freeman, R., Tel-Vered, R. & Willner, I. Impedimetric or Ion-Sensitive Field-Effect Transistor (ISFET) Aptasensors Based on the Self-Assembly of Au Nanoparticle-Functionalized Supramolecular Aptamer Nanostructures. Electroanal 21, 1291-1296, doi:10.1002/elan.200804565 (2009).
10. Swensen, J. S. et al. Continuous, real-time monitoring of cocaine in undiluted blood serum via a microfluidic, electrochemical aptamer-based sensor. J Am Chem Soc 131, 4262-4266, doi:10.1021/ja806531z (2009).
11. Schwake, M., Jentsch, T. J. & Friedrich, T. A carboxy-terminal domain determines the subunit specificity of KCNQ K+ channel assembly. EMBO Rep 4, 76-81, doi:10.1038/sj.embor.embor715 (2003).
12. www.piercenet.com/Objects/View.cfm?type=ProductFamily&ID=01041107
13. Rose, A., Zhu, Z., Madigan, C. F., Swager, T. M. & Bulović, V. Sensitivity gains in chemosensing by lasing action in organic polymers. Nature 434, 876-879, doi: 10.1038/nature03438 (2005).
14. Evans, A. M. D., Corey, D; Barrett, Tom; Mitchell, Matt; Milgram, Eric; Integrated, Nontargeted Ultrahigh Performance Liquid Chromotogarphy/Electrospray Ionization Tandem Mass Spectrometry Platform for the Identification and Relative Quantification of the Small-Molecule Complement of Biological Systems. Anal Chem 81, 6656-6667 (2009).
15. Gorin, D. J., Kamlet, A. S. & Liu, D. R. Reactivity-Dependent PCR: Direct, Solution-Phase in Vitro Selection for Bond Formation. J Am Chem Soc 131, 9189-+, doi:10.1021/ja903084a (2009).
16. Ogawa, A. M., Mizuo. Aptazyme-based riboswitches as label-free and detector-free sensors for cofactors. Bioorganic & Medicinal Chemistry Letters 17, 3156-3160 (2007).
17. Computation carried out using the Oligonucleotide Modeling Platform (OMP, DNA Software, Inc.)
18. Commercially available (Bio-Rad, Invitrogen) real-time PCR reagents use SYBR Green I, a highly specific, double-stranded DNA binding fluorophore. www.bio-rad.com, www.invitrogen.com/site/us/en/home/Products-and-Services/Applications/Nucleic-Acid-Amplification-and-Expression-Profiling/qRT-PCR/Real-Time_PCR-Misc/TaqManvs-SYBR-Green-Chemistries.html

Example 3: Interaction-Dependent PCR: Identification of Ligand-Target Pairs from Libraries of Ligands and Libraries of Targets in a Single-Solution-Phase Experiment ID-PCR is based on the melting temperature ($T_m$) difference between duplex DNA formed intramolecularly versus duplex DNA formed intermolecularly. We hypothesized that binding of a target to its ligand would increase the effective molarity of single-stranded DNA (ssDNA) oligonucleotides linked to the target and ligand, promoting duplex formation between complementary regions on each strand that are otherwise too short to hybridize (FIG. 20*a*). The resulting hairpin could serve as starting point for primer extension. Only the newly extended hairpin contains in a single DNA strand two primer (or primer-binding) sequences that enable subsequent PCR amplification. ID-PCR therefore results in the selective amplification of those DNA sequences previously attached to, and therefore encoding, ligand-target pairs (FIG. 20*a*). In contrast to traditional target-based selections, which rely on the physical separation of active molecules from inactive ones, ID-PCR selectively amplifies DNA encoding active library members. ID-PCR can be applied to a wide variety of targets and potential ligands and to our knowledge is one of the first methods that can identify ligand-target pairs from libraries of small molecules and libraries of targets in a single solution.[14] The nucleic acid-linked (e.g., DNA-linked) ligands required by ID-PCR can be prepared by any suitable method known to those of skill in the art, including, but not limited to the methods described in the references listed under 12 and 15 in the reference section of this example. Similarly, those of skill in the art will readily envision other methods suitable to generate the nucleic acid-linked (e.g., DNA-linked) targets in addition to the simple non-specific conjugation methods described here. The invention is not limited in this respect.

Figure 23:
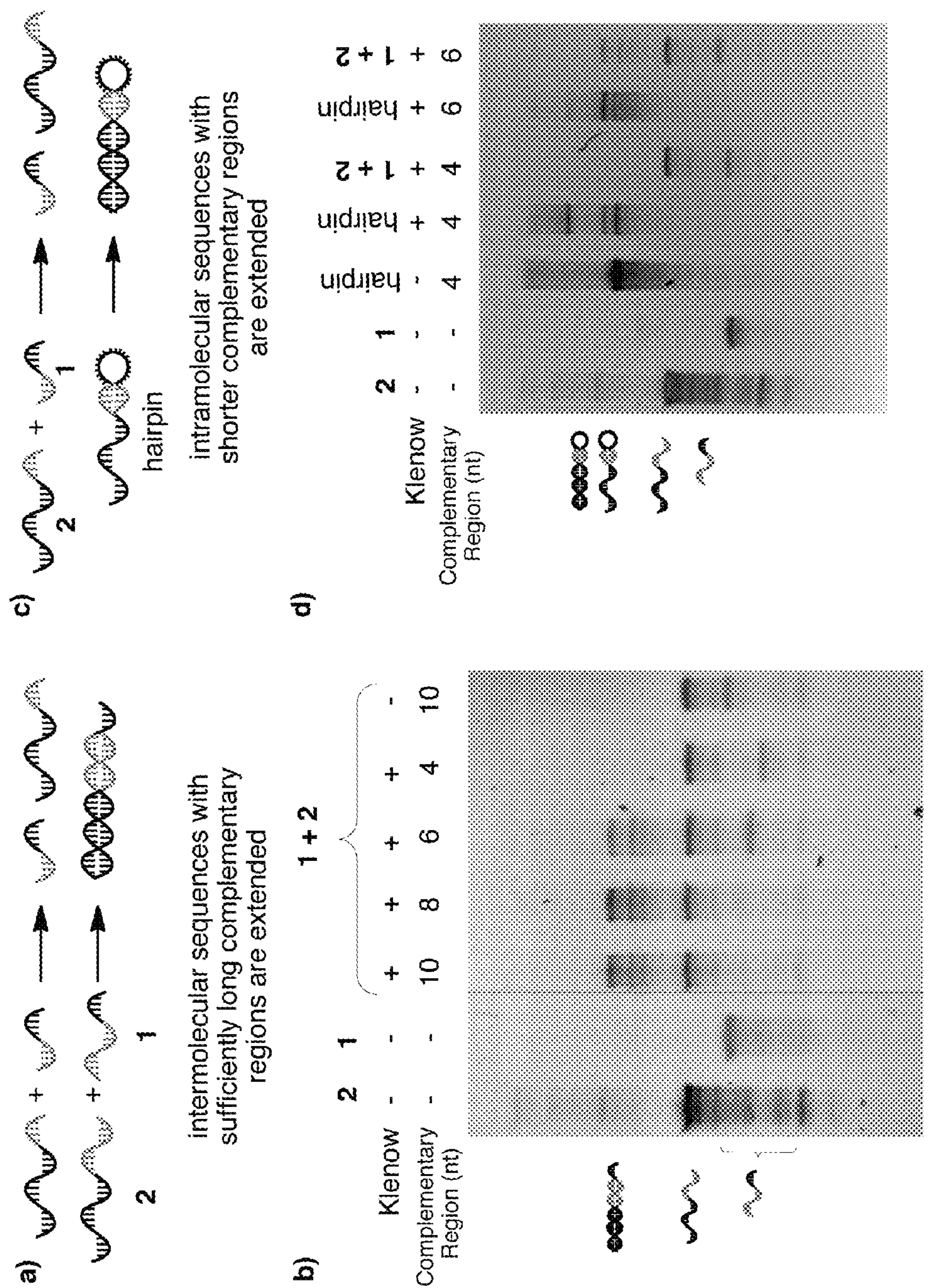
FIG. 23. Optimization of complementary region length.

In order for hairpin extension to report target-ligand binding, it must occur under conditions that both allow binding to take place and enable selective extension of intramolecular duplexes over intermolecular duplexes. Studies on DNA polymerase-mediated extension at 37° C. suggested that a 6-nt complementary region was optimal for enabling intramolecular but not intermolecular duplexes to be extended (FIG. 23). Complementary overlap regions 10 nt and 8 nt in length were efficiently extended intermolecularly, while analogous intermolecular constructs with 6 nt and 4 nt complementary regions were extended poorly or not at all (a and b). Incorporating the 6-nt and 4-nt complementary regions into intramolecular constructs, however, dramatically increased their extension efficiency compared with the corresponding intermolecular constructs (c and d). These results suggest that complementary regions shorter than 8 nt are best suited to benefit from the effective molarity increase caused by target-ligand binding.

FIG. 23 shows optimization of complementary region length. For hairpin extension to effectively report target-ligand binding, it must occur under conditions that both allow binding to take place and selectively extend intramolecular duplexes over intermolecular duplexes. We tested complementary regions of varying lengths to determine which can support the extension of intramolecular but not intermolecular duplexes. A variant of the primer extension protocol described herein was performed, such that an extension mixture consisting of 10×NEB Buffer 2 (1 μL), dNTPs (330 pmol each in 1 μL water), target strand or hairpin (10 pmol in 1 μL water), and 5.5 μL water was prepared. After incubating the reaction at 37° C. for 2 minutes, the ligand strand (10 pmol in 1 μL water) was added. For samples using hairpin oligonucleotides, 1 μL water was added instead. After incubating at 37° C. for 2 minutes, Klenow (2.5 U in 0.5 μL) was added (final reaction volume=10 μL). The reaction was incubated at 37° C. for 20 minutes and the enzyme was inactivated by heating to 75° C. for 20 minutes. The primer extension reaction was analyzed by PAGE (15% TBE-Urea, 200V, 20 minutes, stained with SYBRI, imaged on a ChemiImager).

We investigated whether binding between a small molecule and a protein could replace a covalent linkage in a DNA hairpin and support extension and PCR. Biotin and streptavidin (SA) ($K_d$=40 pM)[4] were chosen as an initial ligand-target pair. We reacted SA with NHS ester-linked ssDNA 1a (the target strand) to generate 1a-SA and also synthesized an oligonucleotide (the ligand strand) conjugated at its 3' end with biotin to provide 2a-biotin. The target and ligand strands shared a 6-nt complementary region. Negative control ligand-DNA conjugates lacking biotin (2) or incapable of hybridizing to 1 (3a-biotin) were also prepared. Each ligand-DNA conjugate (2, 2a-biotin, or 3a-biotin) was individually incubated under identical conditions with 1a-SA and Klenow fragment DNA polymerase at 37° C. and then subjected to qPCR to determine the threshold cycle ($C_T$) value.

Figure 24:
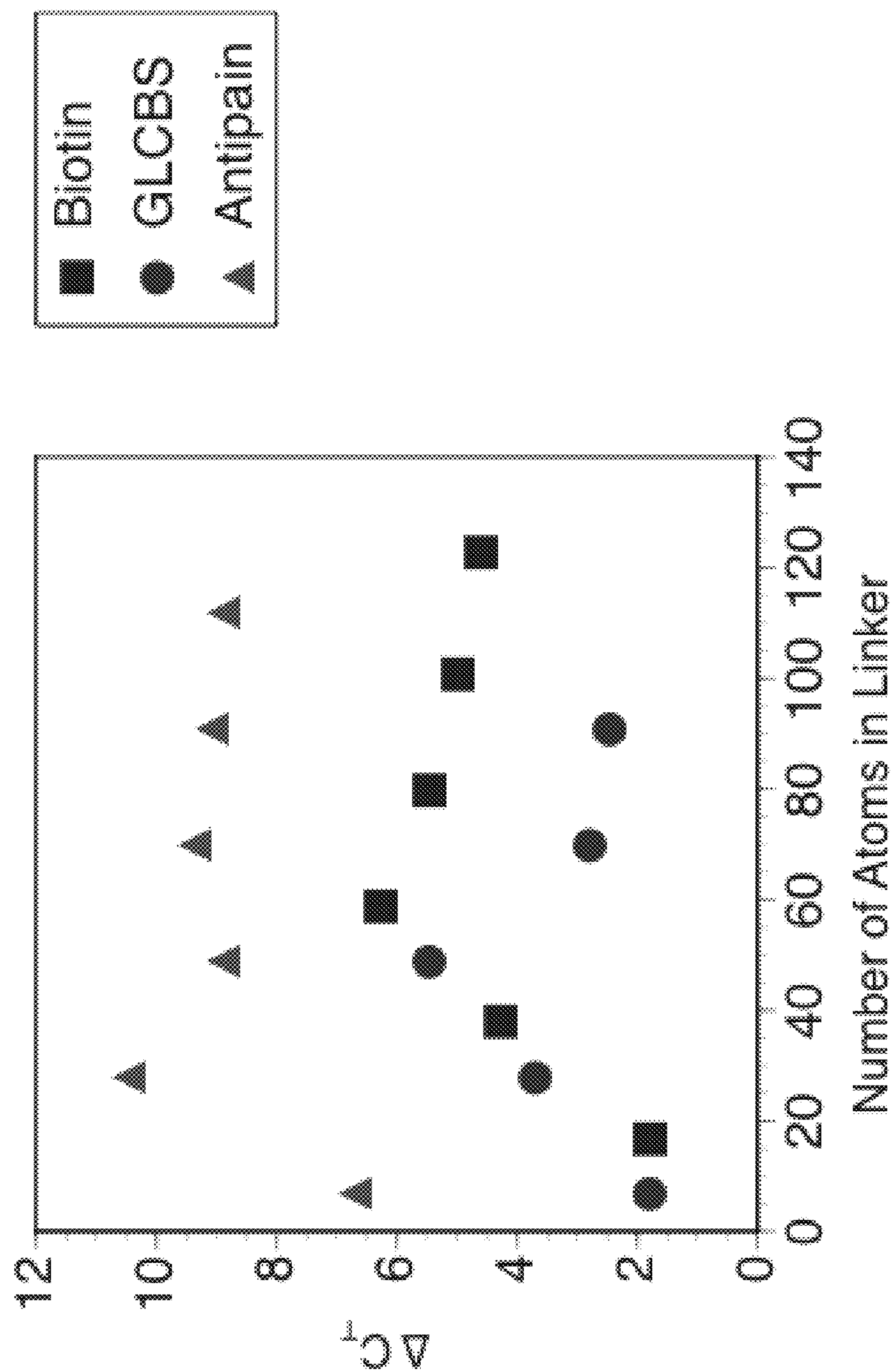
FIG. 24. The affect of ligand-oligonucleotide linker length on ID-PCR efficiency.

Consistent with our hypothesis, the sample containing 1a-SA and 2a-biotin underwent far more efficient PCR amplification than all of the negative controls, resulting in $C_T$ values ≥5 cycles lower (corresponding to ≥32-fold more extension product) than those of the 1a-SA+2 control, the 1a-SA+3a-biotin control, or a sample containing 1a-SA+2a-biotin but lacking Klenow (FIG. 20*b*). A positive control, containing a 10-nt complementary region that hybridizes to 2 independent of target-ligand binding, exhibited a comparable $C_T$ value to that of 1a-SA+2a-biotin sample. Importantly, the addition of excess free biotin abrogated the ID-PCR of 2a-biotin with 1a-SA (FIG. 20*b*). ID-PCR was surprisingly tolerant of ligand-DNA linker lengths between ~28 and 123 atoms (FIG. 24). Together, these results indicate that specific ligand-target binding can promote DNA extension and trigger the selective PCR amplification of DNA sequences linked to ligand-target pairs.

FIG. 24 shows the effect of ligand-oligonucleotide linker length on ID-PCR efficiency. Because target-ligand binding involves complexes of large and variable size that might influence complementary region hybridization in unanticipated ways, we sought to understand the structural requirements for successful ID-PCR. We performed ID-PCR on 1a-SA and 2a-biotin conjugates, while varying the length of the linker between the biotin group and the DNA oligonucleotide from 4 to 34 polyethyleneglycol (PEG) units. Primer extension and qPCR reactions were performed as described above (SI-9 and SI-10). For streptavidin (1a-SA), the following ligand strand sequences were used: 2-biotin-17, 2-biotin-38, 2a-biotin, 2-biotin-80, 2-biotin-101, and 2-biotin-123. For trypsin (1j-trypsin), the following ligand strand sequences were used: 2-antipain-7, 2-antipain-28, 2c-antipain, 2-antipain-70, 2-antipain-91, and 2-antipain-113. For carbonic anhydrase (1c-CA), the following ligand strand sequences were used: 2-GLCBS-7, 2-GLCBS-28, 2e-GLCBS, 2-GLCBS-70, and 2-GLCBS-91.

As linker length was increased from 4 to 16 PEG units (7 to 59 atoms), we observed an increase in $\Delta C_T$ values upon ligand-receptor binding towards the positive control value of 8 cycles, suggesting that the DNA-ligand linker must be sufficiently long to simultaneously accommodate ligand-target binding, primer-template hybridization, and DNA polymerase binding. As the length of the PEG linker was further increased from 16 to 34 PEG units, $\Delta C_T$ values slowly decreased, consistent with the expected decrease in effective molarity of the primer and template as the linker is further lengthened. Similar results were obtained from analogous experiments performed with 1b-trypsin and 2c-antipain sequences and with 1c-CA and 2e-GLCBS sequences. Collectively, these results demonstrate that a single linker structure is appropriate for the three targets investigated here and suggest that ID-PCR will be able to accommodate targets of varying size and relative orientation.

Next we tested the ability of ID-PCR to report ligand-target interactions of much lower affinity ($K_d$=~2 nM to ~3 μM; protein target affinities of DNA-linked ligands other than biotin were measured and found to be within 5-fold of the reported affinities for the free small molecules (FIG. 25)). Ligand strand 2 was conjugated to a lower affinity SA ligand, desthiobiotin ($K_d$=2 nM).[5,6] When 2b-desthiobiotin was combined with 1a-SA and subjected to Klenow extension and qPCR, 2b-desthiobiotin was amplified with efficiency comparable to that of 2a-biotin (FIG. 20*b*). Similarly, trypsin and antipain ($K_i$=100 nM)[7] were conjugated to DNA to form 1b-trypsin and 2c-antipain The 1b-trypsin+2c-antipain pair resulted in a seven-cycle $C_T$ advantage relative to negative controls lacking ligand, containing 2 conjugated to unrelated ligands, or containing an excess of free antipain (FIGS. 20*c*, 24, and 25).

Figure 25:
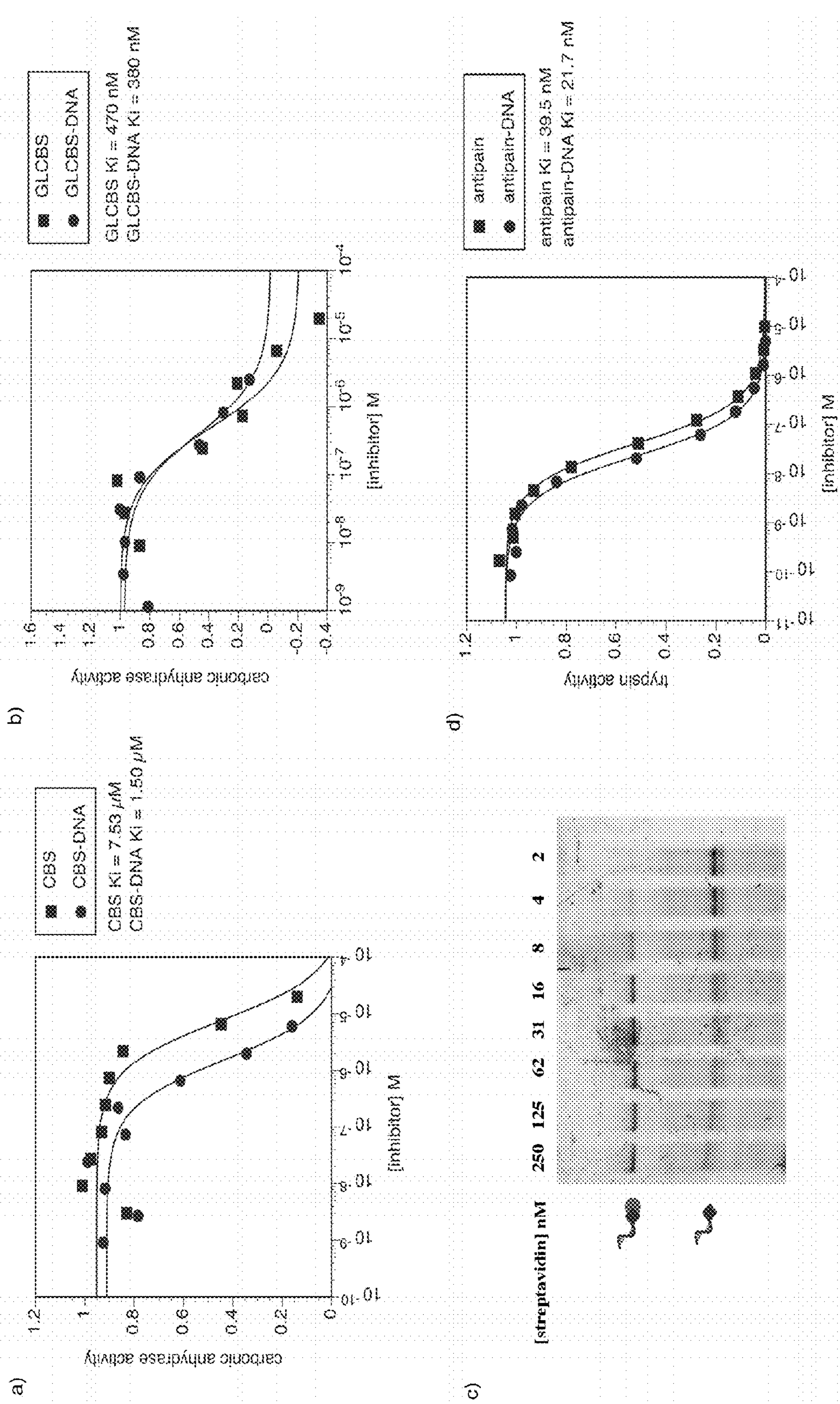
FIG. 25. Affinities of ligands and ligand-DNA conjugates for protein targets.

FIG. 25 shows affinities of ligands and ligand-DNA conjugates for protein targets. The binding, annealing, and extension steps of ID-PCR were performed at 37° C., and for this reason, the affinity measurements for carbonic anhydrase and trypsin were taken at this temperature. (a) The affinity of 2d-CBS for carbonic anhydrase is 1.50 μM, and is approximately 5-fold higher than the affinity of CBS for CA (7.53 μM). This difference is likely due to the presence of the hydrophobic hexylamine at the 3' end of the oligonucleotide, rather than an effect of the oligonucleotide itself; it is well known that derivatives of CBS containing hydrophobic groups at this position have increased affinities for carbonic anhydrase.[18] (b) As previously reported,[19] addition of a hydrophobic dipeptide (gly-leu) to CBS increased its affinity for CA (GLCBS $K_i$=470 nM). Conjugation of GLCBS to DNA did not greatly affect its affinity for CA (2s-GLCBS=380 nM). (c) The apparent $K_d$ of 2b-desthiobiotin for streptavidin is 8 nM. (d) Antipain and 2c-antipain have similar affinities for trypsin ($K_i$=39.5 nM and $K_i$=21.7 nM, respectively).

DNA encoding carbonic anhydrase II (CA) (1c-CA) and CA ligands 4-carboxy benzene sulfonamide (CBS) ($K_d$=3.2 μM)[8] (2d-CBS) and Gly-Leu-CBS ($K_d$=9 nM)[9] (2e-GLCBS) was amplified far more efficiently (six- to seven-cycle $\Delta C_T$) than control reactions lacking ligand (2), containing a mismatched complementary region (3b-CBS), or containing an excess of free GLCBS (FIGS. 20*d*, 24, and 25). Collectively, these results suggest that ID-PCR can serve as a general method to detect a wide variety of small molecule-protein interactions of varying affinities.

Any class of intermolecular interaction can be detected by ID-PCR. Next we tested the ability of ID-PCR to selectively amplify DNA sequences encoding nucleic acid aptamer-ligand pairs.[10] A 68-nt DNA aptamer that binds daunomycin ($K_d$=272 nM)[11] and doxorubicin was synthesized at the 5' end of the target strand to generate 1d-aptamer. Daunomycin or doxorubicin was conjugated to the ligand strand to afford 2g-Dn or 2h-Dx, respectively. Consistent with the above results for protein targets, ID-PCR reactions containing both 1d-aptamer and either 2g-Dn or 2h-Dx were amplified more efficiently than samples with 2f in place of 2g-Dn ($\Delta C_T$=8 cycles), or samples containing free doxorubicin ($\Delta C_T$=4 cycles) (FIG. 20*e*). These results indicate that ID-PCR can be used to selectively amplify DNA linked to small molecule-aptamer pairs.

Figure 26:
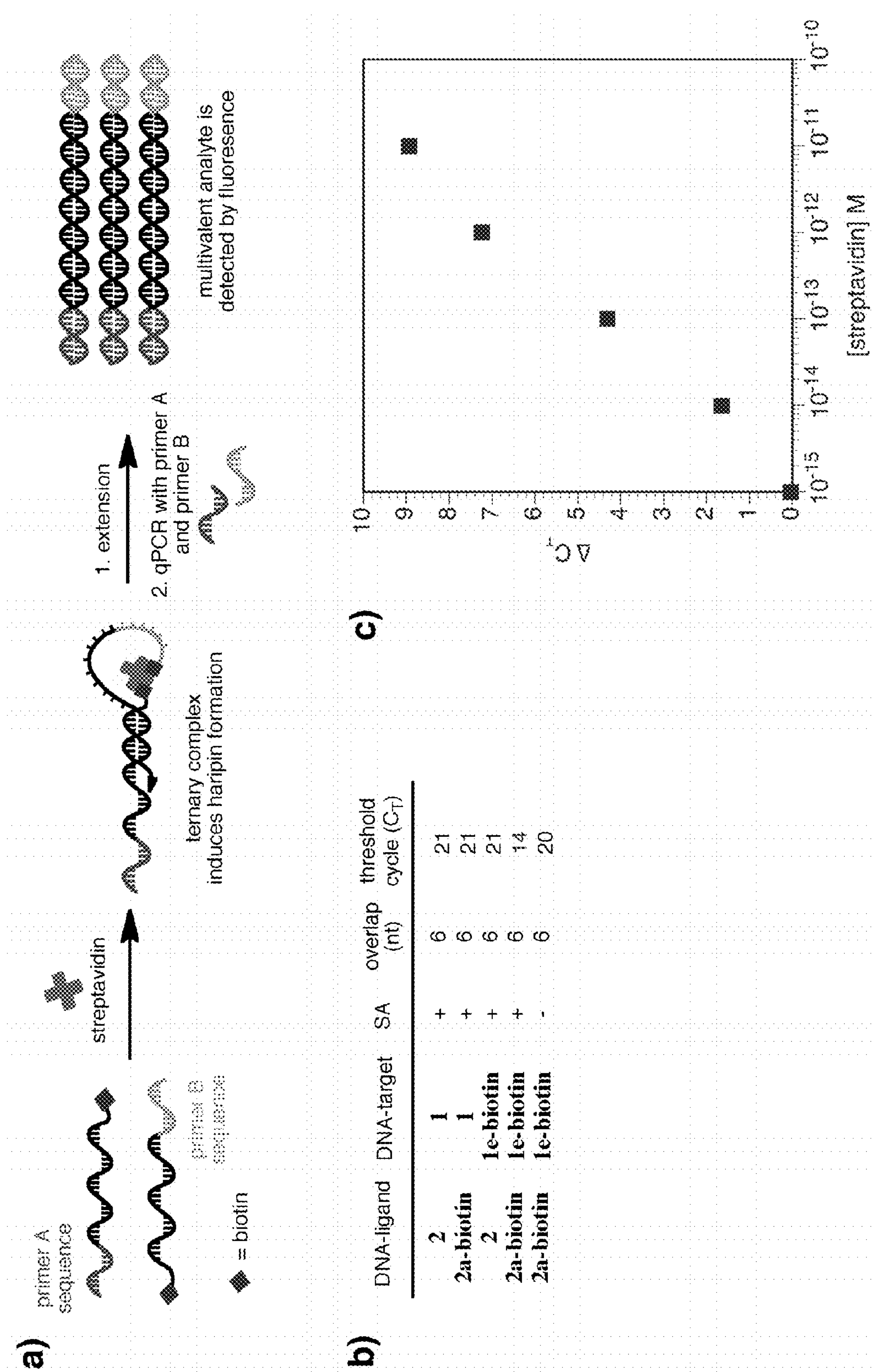
FIG. 26. Detection of multivalent analytes by ID-PCR.

We wondered if the covalent bond between the target and the target oligonucleotide could be replaced by a non-covalent interaction, resulting in ID-PCR of a ternary complex between two DNA-linked ligands and a multivalent target.[5,12,13] To test this possibility, we conjugated biotin to the target strand to generate 1e-biotin, which can hybridize with 2a-biotin. We hypothesized that in the presence of SA a ternary complex of SA and two DNA-linked biotin ligands would form, enabling DNA hybridization, extension, and amplification. Indeed, ID-PCR in this "sandwich" mode detected as little as $2\times10^{-19}$ moles (200 zeptomoles) SA (FIG. 26). These results suggest the potential of ID-PCR for the sensitive detection of multivalent analytes in sandwich assays.

FIG. 26 exemplifies the detection of multivalent analytes by ID-PCR. FIG. 26(*a*) shows a scheme for detection of multivalent analytes using ID-PCR. A non-covalent interaction can replace the covalent bond between the target and the target strand. In the presence of the analyte, a ternary complex comprising the analyte and two ligands forms, promoting hybridization of the complementary regions on the ligand-linked oligonucleotides and resulting in increased amplification efficiency of the DNA. (b) 200 fmol of 1e-biotin or 1 and 200 fmol of 2a-biotin or 2 were diluted in 14 μL of 1.5×NEB Buffer 2. After incubation at 94° C. for 5 minutes followed by 5 minutes at 37° C., 1 μL of $H_2O$ with or without 100 fmol of streptavidin was added. Following incubation at 37° C. for 15 minutes, 2.5 U of Klenow Fragment exo$^-$ in 5 μL $H_2O$ pre-equilibrated at 37° C. were added. The primer extension reaction was incubated at 37° C. for 15 minutes. The polymerase was inactivated by heating at 75° C. for 20 minutes. The extension reaction was subjected to qPCR as described above. Samples containing 1e-biotin, 2a-biotin, and streptavidin are amplified more efficiently than samples lacking streptavidin, or lacking one of the biotin moieties ($\Delta C_T$=6-7 cycles). (c) For the detection of sub-attomole quantities of streptavidin a slight variation of the protocol was applied: 200 amol of 1e-biotin and 2a-biotin were incubated with 200, 20, 2, 0.2, or 0.02 amol of streptavidin, followed by addition of Klenow as above. The primer extension mixture was not diluted for qPCR analysis. In this sandwich mode ID-PCR can be used to detect as little as $2\times10^{-19}$ moles (200 zeptomoles of streptavidin).

Since applications of ID-PCR include library screening, we performed a series of model selections to test the ability of ID-PCR to selectively enrich DNA encoding authentic ligands in the presence of an excess of non-binding small molecule-DNA conjugates (FIG. 21*a*). A 1:10, 1:100 or 1:1000 ratio of 2i-biotin:2k-GLCBS was combined with 1a-SA and subjected to Klenow extension and PCR. The same mixtures of 2i-biotin:2k-GLCBS were also subjected to ID-PCR in the presence of 1 (without SA) as a control. When ID-PCR was performed with 1a-SA, the biotin-encoding sequence 2i was strongly enriched among the resulting PCR products (FIG. 21*b*). In contrast, ID-PCR with 1 resulted in no enrichment of the biotin-linked strand. Similarly strong enrichment was observed for CA-GLCBS binding and for DNA aptamer-daunomycin binding in the presence of large excesses of non-binding conjugates (FIG. 21*c-e*). These findings demonstrate that ID-PCR can enrich DNA encoding a ligand ~100-fold over DNA encoding small molecules without target affinity for a variety of protein and nucleic acid targets.

Finally, we tested the ability of ID-PCR to simultaneously evaluate all possible combinations of multiple ligands and multiple targets in a single solution. We performed a model selection in which five small-molecule ligands (biotin, desthiobiotin, GLCBS, CBS, and antipain) and three targets (SA, CA, and trypsin), each conjugated to unique sequence tags, were present in one solution containing a 250-fold excess of DNA-linked ligand (hexylamine) and a 250-fold excess of a DNA-linked target (glutathione S-transferase) not known to interact with the other ligands or targets. The negative control ligand and target were conjugated to libraries of 256 different sequence tags. The resulting solution therefore contained equimolar quantities of each of 261 ligand sequences and each of 259 target sequences, collectively representing 67,599 possible ligand-target sequence combinations. A control sample was prepared identically except using DNA not conjugated to any protein targets. Both samples were subjected to ID-PCR followed by high-throughput DNA sequencing.

For each of the three different proteins in the library, the most highly enriched sequences relative to the control sample correspond to their known ligands (FIG. 22), despite the large excess of non-binding ligands and the fact that ligand-target affinities span five orders of magnitude. The mean enrichment factor across all 67,599 possibilities was 1.4, while the enrichment factors corresponding to the five known ligand-target pairs ranged from 75 to 3,000. Only three enrichment factors above 75 were observed among presumed non-binding pairs out of 67,594 possibilities, representing a low false positive rate (Tables 2 and 3). These results establish the ability of ID-PCR to evaluate a small-molecule library for affinity to a protein target library in a single experiment, and suggest that ID-PCR can identify ligand-target pairs across a wide range of affinities in a highly multiplexed format.

Materials and Methods

General Methods.

All chemical reagents were purchased from Sigma-Aldrich, unless otherwise noted. Water was purified with a Milli-Q purification system. DNA oligonucleotides were synthesized on a PerSeptive Biosystems Expedite 8909 DNA synthesizer or purchased from Integrated DNA Technologies. All reagents and phosphoramidites for DNA synthesis were purchased from Glen Research. All oligonucleotides were synthesized and deprotected according to manufacturer's protocols. Oligonucleotides were purified by reverse-phase high-pressure liquid chromatography (HPLC, Agilent 1200) using a C18 stationary phase (Eclipse-XDB C18, 5 μm, 9.4×200 mm) and an acetonitrile/100 mM triethylammonium acetate gradient. Oligonucleotide concentrations were quantitated by UV spectroscopy using a Nanodrop ND1000 spectrophotometer. Non-commercial oligonucleotides were characterized by LC/ESI-MS; reverse-phase separation was performed on an Alliance 2695 (Waters) HPLC system using a UPLC BEH C18 column (1.7 μm, 2.1×50 mm) stationary phase and 6 mM aqueous triethylammonium bicarbonate/MeOH mobile phase interfaced to a Q-Tof Micro mass spectrometer (Waters). Oligonucleotides greater than 70 nt in length were analyzed by PAGE.

DNA Sequences

In the sequences below: <3>=biotinTEG phosphoramidite (Glen Research, 10-1955); <4>=3' Thiol Modifier C6 S-S (20-2936); <5>=3'biotinTEG (20-2955); <6>=3'desthiobiotinTEG (20-2952); <7>=Spacer 18 (10-1918); <8>=5'CarboxyC10 (10-1935); <9>=3' aminoC6 (20-2956); <0>=Cy3 (10-5913) and N is an equimolar solution of A, T, C, and G phosphoramidites. Underlined sequences are barcodes or sequences recognized by restriction endonucleases. Italicized portions of primer sequences are adaptor sequences required for Illumina sequencing (©2007-2009. Illumina, Inc. All rights reserved). SEQ ID NOs are given in parentheses.

1, 1b, 1c:
5'-<8><7>CGGCGATCGTGAAGGAGGCTAGACTGAGTGAG-3' (51)

1a:
5'-<8><7><0>CGGCGATCGTGAAGGAGGCTAGACTGAGTGAG-3' (52)

positive control:
5'-TGGATCGTGATGACTGTCCCGACAAGCATACGTATCTCACTCAGT<9>-3' (53)

2:
5'-TGGATCGTGATGACTGTCCCGACAAGCATACGTATCTCACT<7><7><9>-3' (54)

2a-biotin:
5'-TGGATCGTGATGACTGTCCCGACAAGCATACGTATCTCACT<7><7><5>-3' (55)

3a-biotin:
5'-TGGATCGTGATGACTGTCCCGACAAGCATACGTATTACTAG<7><7><5>-3' (56)

2b-desthiobiotin:
5'-TGGATCGTGATGACTGTCCCGACAAGCATACGTATCTCACT<7><7><6>-3' (57)

2c-antipain, 2d-CBS, 2e-GLCBS:
5'-TGGATCGTGATGACTGTCCCGACAAGCATACGTATCTCACT<7><7><9>-ligand-3' (58)

3b-CBS:
5'-TGGATCGTGATGACTGTCCCGACAAGCATACGTATTACTAG<7><7><9>-CBS-3' (59)

1d-aptamer:
5'-ACCATCTGTGTAAGGGGTAAGGGGTGGGGGTGGGTACGTCTCGGCGATCGTGAAGGAGACT GAGTGAG-3' (60)

2f:
5'-GGATTCTGTATGACTGTCCCACGTATCTCACT<7><4>-3' (61)

2g-Dn, 2h-Dx:
5'-GGATTCTGTATGACTGTCCCACGTATCTCACT<7><4>-linker-ligand-3' (62)

2i-biotin:
5'-TGGATCGTGATGACTGTCCCGACAAGAATTCGTATCTCACT<7><7><5>-3' (63)

2k-GLCBS:
5'-TGGATCGTGATGACTGTCCCGACAAGCTTACGTATCTCACT<7><7><9>-GLCBS-3' (64)

1f-aptamer:
5'-ACCATCTGTGTAAGGGGTAAGGGGTGGGGGTGGGTACGTCTCGGCGATCGTGAAGGAGTAAGCTACTG
AGTGAG-3' (65)

1g-aptamer:
5'-ACCATCTGTGTAAGGGGTAAGGGGTGGGGGTGGGTACGTCTCGGCGATCGTGAAGGAGATGCATAC
TGAGTGAG-3' (66)

1h-unstructured DNA:
5'-ATTGATCACTTGATTTCTGCCCATTGATTAAAGTCGCAAGTCGGCGATCGTGAAGGAGTAAG
CTACTGAGTGAG-3' (67)

21:
5'-TGGATCGTGATGACTGTCCCGACAAGCATACGTATCTCACT<7><4>-3' (68)

2m:
5'-TGGATCGTGATGACTGTCCCGACAAATGCATGTATCTCACT<7><4>-3' (69)

2n-Dn:
5'-TGGATCGTGATGACTGTCCCGACAAATGCATGTATCTCACT<7><4>-linker-Dn-3' (70)

1i:
5'-<8><7>CGGCGATCGTGAAGGAGGCTCGAGTGAGTGAG-3' (71)

1k:
5'-<8><7>CGGCGATCGTGAAGGAGGCTAGCCTGAGTGAG-3' (72)

1j:
5'-<8><7>CGGCGATCGTGAAGGAGGANNNNTTGAGTGAG-3' (73)

2o-CBS:
5'-TGGATCGTGATGACTGTCCCGACAAGCTTACGTATCTCACT<7><7><9>-CBS-3' (74)

2p:
5'-TGGATCGTGATGACTGTCCCGACAACCATGGGTATCTCACT<7><7><9>-3' (75)

2q-desthiobiotin:
5'-TGGATCGTGATGACTGTCCCGACAACCATGGGTATCTCACT<7><7><9>-desthloblotin-3' (76)

-continued

2r:
5'-TGGATCGTGATGACTGTCCCGACAAGGATCCGTATCTCACT<7><7><9>-3' (77)

2s-GLCBS:
5'-TGGATCGTGATGACTGTCCCGACAAGGATCCGTATCTCACT<7><7><9>-GLCBS-3' (78)

2t:
5'-TGGATCGTGATGACTGTCCCGACAAAGTACTGTATCTCACT<7><7><9>-3' (79)

2u-antipain:
5'-TGGATCGTGATGACTGTCCCGACAAAGTACTGTATCTCACT<7><7><9>-antipain-3' (80)

2v-amine:
5'-TGGATCGTGATGACTGTCCCGACAATNNNNAGTATCTCACT<7><7><9>-3' (81)

Primer A:
5'-TGGATCGTGATGACTGTCCC-3' (82)

Primer B:
5'-CGGCGATCGTGAAGGAG-3' (83)

Primer C:
5'-*AATGATACGGCGACCACCGAGATCTACACTCTTTCCCTACACGACGCTCTTCCGATCTT*TCTCGCGGCGATCGTGAAGGAG-3' (84)

Primer D:
5'-*AATGATACGGCGACCACCGAGATCTACACTCTTTCCCTACACGACGCTCTTCCGATCTT*CTACCCGGCGATCGTGAAGGAG-3' (85)

Primer E:
5'-*CAAGCAGAAGACGGCATACGAGCTCTTCCGATCT*TGGATCGTGATGACTGTCCC-3' (86)

FIG. 23:
1-4 nt overlap:
5'-<8><7>CGGGGATCGTGAAGGAGGCTAGACTG-3' (87)

1-6 nt overlap:
5'-<8><7>CGGGGATCGTGAAGGAGGCTAGACTGAG-3' (88)

1-8 nt overlap:
5'-<8><7>CGGGGATCGTGAAGGAGGCTAGACTGAGTG-3' (89)

1-10 nt overlap:
5'-<8><7>CGGGGATCGTGAAGGAGGCTAGACTGAGTGAG-3' (90)

2:
5'-TGAGTCGTGATGACTGTCCCGACAAGCTTACGTATCTCACTCAGT<9>-3' (91)

hairpin-4 nt overlap:
5'-TGAGTCGTGATGACTGTCCCGACAAGCTTACGTATCTCACTCAG<7>CGGGGATCGTGAAGGAGGCTAGACTG-3' (92)

hairpin-6 nt overlap:
5'-TGAGTCGTGATGACTGTCCCGACAAGCTTACGTATCTCACTCAG<7>CGGGGATCGTGAAGGAGGCTAGACTGAG-3' (93)

FIG. 24:
2-biotin-17:
5'-TGGATCGTGATGACTGTCCCGACAAGCATACGTATCTCACT<5>-3' (94)

2-biotin-38:
5'-TGGATCGTGATGACTGTCCCGACAAGCATACGTATCTCACT<7><5>-3' (94)

2-biotin-80:
5'-TGGATCGTGATGACTGTCCCGACAAGCATACGTATCTCACT<7><7><7><5>-3' (94)

2-biotin-101:
5'-TGGATCGTGATGACTGTCCCGACAAGCATACGTATCTCACT<7><7><7><7><5>-3' (94)

2-biotin-123:
5f-TGGATCGTGATGACTGTCCCGACAAGCATACGTATCTCACT<7><7><7><7><7><5>-3' (94)

2-amine-7:
5'-TGGATCGTGATGACTGTCCCGACAAGCATACGTATCTCACT<9>-3' (94)

2-amine-28:
5'-TGGATCGTGATGACTGTCCCGACAAGCATACGTATCTCACT<7><9>-3' (94)

2-amine-70:
5'-TGGATCGTGATGACTGTCCCGACAAGCATACGTATCTCACT<7><7><7><9>-3' (94)

-continued

```
2-amine-91:
5'-TGGATCGTGATGACTGTCCCGACAAGCATACGTATCTCACT<7><7><7><7><9>-3'(94)

2-amine-112:
5'-TGGATCGTGATGACTGTCCCGACAAGCATACGTATCTCACT<7><7><7><7><7><9>-3' (94)

2-antipain-7:
5'-TGGATCGTGATGACTGTCCCGACAAGCATACGTATCTCACT<9>-antipain-3' (94)

2-antipain-28:
5'-TGGATCGTGATGACTGTCCCGACAAGCATACGTATCTCACT<7><9>-antipain-3' (94)

2-antipain-70:
5'-TGGATCGTGATGACTGTCCCGACAAGCATACGTATCTCACT<7><7><7><9>-antipain-3' (94)

2-antipain-91:
5'-TGGATCGTGATGACTGTCCCGACAAGCATACGTATCTCACT<7><7><7><7><9>-antipain-3' (94)

2-antipain-112:
5'-TGGATCGTGATGACTGTCCCGACAAGCATACGTATCTCACT<7><7><7><7><7><9>-antipain-3' (94)

2-GLCBS-7:
5'-TGGATCGTGATGACTGTCCCGACAAGCATACGTATCTCACT<9>-GLCBS-3' (94)

2-GLCBS-28:
5'-TGGATCGTGATGACTGTCCCGACAAGCATACGTATCTCACT<7><9>-GLCBS-3' (94)

2-GLCBS-70:
5'-TGGATCGTGATGACTGTCCCGACAAGCATACGTATCTCACT<7><7><7><9>-GLCBS-3' (94)

2-GLCBS-91:
5'-TGGATCGTGATGACTGTCCCGACAAGCATACGTATCTCACT<7><7><7><7><9>-GLCBS-3' (94)

2-GLCBS-112:
5'-TGGATCGTGATGACTGTCCCGACAAGCATACGTATCTCACT<7><7><7><7><7><9>-GLCBS-3' (94)

FIG. 25:
1e-biotin:
5'-<3><7>CGGCGATCGTGAAGGAGGCTAGACTGAGTGAG-3' (95)

FIG. 26:
complementary 20mer:
5'-GGGACAGTCATCACGA<0>TCCA-3' (96)
```

Synthesis of Ligand-DNA Conjugates 2a-biotin, 2b-desthiobiotin, and 3a-biotin were prepared directly during oligonucleotide synthesis using commercially available phosphoramidites. 2c, 2d, 2e, 2k, 2o, 2q, 2s, 2u, and 3c were prepared by conjugating antipain, CBS, GLCBS, or desthiobiotin (referred to below as the "ligand") to the corresponding 3'-amine modified oligonucleotide (sequences 2 or 3 above). To 215 μL DMSO was added the ligand (1.25 μmol in 12.5 μL DMSO), sulfo-NHS (3.33 μmol in 10 μL 2:1 DMSO:$H_2O$), and 1-ethyl-3-(3-dimethylaminopropyl carbodiimide) (EDC, 1.2 μmol in 12 μL DMSO). After the reaction mixture (final volume=249.5 μL) was stirred at room temperature for 30 minutes, 3'-amine modified oligonucleotide (5 nmol in 10 μL $H_2O$) and triethylamine/HCl pH 10 (50 μL of a 500 mM stock solution) were added. The reaction was stirred at room temperature for 12 hours. Tris-HCl, pH 8.0 (20 μL of a 500 mM stock solution) was added and the reaction mixture was incubated for 1 h at room temperature. The products were purified by reverse-phase HPLC, precipitated with ethanol, and characterized by UV/Vis spectroscopy and LC/MS.

Synthesis of DNA-Daunomycin and DNA-Doxorubicin Conjugates

To 3'-dithiol-modified DNA (4 nmol in 37.5 μL 1×PBS buffer, sequence 2f or 2m above) were added 7.5 μL of 500 mM pH 8 HEPES buffer and 5 μL of 1 M aqueous DTT. After 30 minutes at room temperature, the DNA fraction was isolated by size exclusion chromatography (SEC) using Centri-Sep spin columns (Princeton Separations, Inc.). To the deprotected 3' thiol-modified DNA was then added 29 μL of 3×PBS buffer supplemented with 3 mM EDTA and the appropriate small molecule (daunomycin or doxorubicin) (200 nmol in 20 μL of 10 mM pH 7.4 Tris-HCl buffer). The bifunctional linker SM(PEG)$_{24}$ (Piercenet) was then added (100 nmol in 1 μL of DMSO). After brief agitation, the reaction mixture was incubated at room temperature for 90 minutes, and then purified by SEC using a Nap-5 column (GE Healthcare). The product was further purified by HPLC, and characterized by UV/Vis spectroscopy and LCMS.

LC/MS Characterization of Oligonucleotides and Ligand-Oligonucleotide Conjugate

All raw data were processed using MassLynx MaxEnt1 (Waters Micromass) to obtain the deconvoluted mass using m/z 1500-5000 and the following MaxEnt1 parameters: 5000 Da output mass range around expected mass (from 5000 to 25000 Da, depending on construct); 0.1 Da output resolution; minimum intensity ratio left and right, 33%; width at half height for uniform Gaussian model, 0.75; number of iterations, 10.

| Oligonucleotide | Expected Mass (Da) | Observed Mass (Da) |
|---|---|---|
| 1 | 10614.2 | 10612.0 |
| 1a | 11121.7 | 11119.0 |
| positive control | 13975.2 | 13973.4 |
| 2 | 13427.9 | 13425.5 |
| 2a-biotin | 13818.4 | 13815.2 |
| 2b-desthiobiotin | 13788.4 | 13786.0 |
| 2c-antipain | 14014.6 | 14012.7 |
| 2e-GLCBS | 13771.9 | 13770.0 |

-continued

| Oligonucleotide | Expected Mass (Da) | Observed Mass (Da) |
|---|---|---|
| 2d-CBS | 13601.9 | 13601.8 |
| 3a-biotin | 13882.5 | 13879.7 |
| 3b | 13492.1 | 13489.3 |
| 3c-CBS | 13675.1 | 13675.5 |
| 2f | 10437.0 | 10437.0 |
| 2g-Dn | 12113.8 | 12112.0 |
| 2h-Dx | 12129.8 | 12127.1 |
| 2i-biotin | 13833.4 | 13831.4 |
| 2j | 13419.0 | 13415.8 |
| 2k-GLCBS | 13771.9 | 13770.1 |
| 1e-biotin | 10933.3 | 10932.8 |
| 2l | 13232.8 | 13232.7 |
| 2m | 13246.8 | 13246.2 |
| 2n-Dn | 14923.6 | 14919.7 |
| 1i | 10630.1 | 10628.6 |
| 1j | 10590.5 | 10589.2 |
| 1k | 10629.2 | 10626.0 |
| 2o-CBS | 13601.9 | 13598.8 |
| 2p | 13443.8 | 13441.8 |
| 2q-desthiobiotin | 13640.2 | 13636.4 |
| 2r | 13443.9 | 13440.6 |
| 2s-GLCBS | 13796.9 | 13797.3 |
| 2t | 13442.9 | 13440.1 |
| 2u-antipain | 14029.6 | 14026.9 |
| 2v | 13443.0 | 13441.2 |
| 2-for FigS1 | 13966.2 | 13965.0 |
| 1-4 nt overlap | 8735.9 | 8734.1 |
| 1-6 nt overlap | 9378.4 | 9377.1 |
| 1-8 nt overlap | 10011.8 | 10008.4 |
| 1-10 nt overlap | 10654.2 | 10651.4 |
| hairpin-4 nt overlap | 22334.3 | 22331.0 |
| hairpin-6 nt overlap | 22976.3 | 22971.5 |
| 2-biotin-17 | 13129.8 | 13126.6 |
| 2-biotin-38 | 13474.1 | 13470.1 |
| 2-biotin-80 | 14162.7 | 14159.6 |
| 2-biotin-101 | 14507.0 | 14503.4 |
| 2-biotin-123 | 14851.3 | 14847.2 |
| 2-amine-7 | 12739.4 | 12740.0 |
| 2-amine-28 | 13083.7 | 13082.0 |
| 2-amine-70 | 13772.3 | 13770.0 |
| 2-amine-91 | 14116.6 | 14113.1 |
| 2-amine-112 | 14460.9 | 14458.6 |
| 2-antipain-7 | 13328.1 | 13322.0 |
| 2-antipain-28 | 13672.4 | 13667.0 |
| 2-antipain-70 | 14361.0 | 14355.0 |
| 2-antipain-91 | 14705.3 | 14700.9 |
| 2-antipain-112 | 15049.6 | 15044.4 |
| 2-GLCBS-7 | 13092.4 | 13088.9 |
| 2-GLCBS-28 | 13436.7 | 13435.2 |
| 2-GLCBS-70 | 14125.3 | 14124.8 |
| 2-GLCBS-91 | 14469.6 | 14466.8 |
| complementary 20mer | 6631.6 | 6616.1 |

Synthesis of Protein-DNA Conjugates

To 50 μL of sodium MES buffer (50 mM, pH 5.4) was added sNHS (1.6 mmol in 5 μL 2:1 DMSO: $H_2O$), EDC (500 nmol in 5 μL DMSO), and the corresponding 5'-carboxylate modified oligonucleotide (0.8-7 nmol in 22-35 μL water, sequences 1, 1a, 1b, 1c, 1i, 1k, or 1j above). The resulting solution was incubated at room temperature for 30 minutes and then subjected to SEC using an Illustra MicroSpin G-25 spin column (GE Healthcare). The corresponding protein (0.4-5.7 nmol protein in 5-50 μL PBS of streptavidin (New England Biolabs), bovine carbonic anhydrase II, bovine trypsin, or glutathione S-transferase (Sigma Aldrich)) was added to a final stoichiometry of ~0.7:1 protein:DNA. The reaction mixture was incubated at room temperature for 4 hours, then quenched by addition of Tris-HCl pH 8.0 (10 μL of a 500 mM stock solution). The protein-DNA conjugates were purified by SEC on a Sephadex 75 10/300 column (GE Healthcare) using an AKTA FPLC (Amersham Biosciences) over 1.5 column volumes at a flow rate of 0.8 mL/min in 1×PBS. Fractions were characterized by SDS-PAGE (FIG. 27). 1a-SA was quantitated by UV-Vis spectroscopy using absorption of the Cy3 chromophore.

Figure 27:
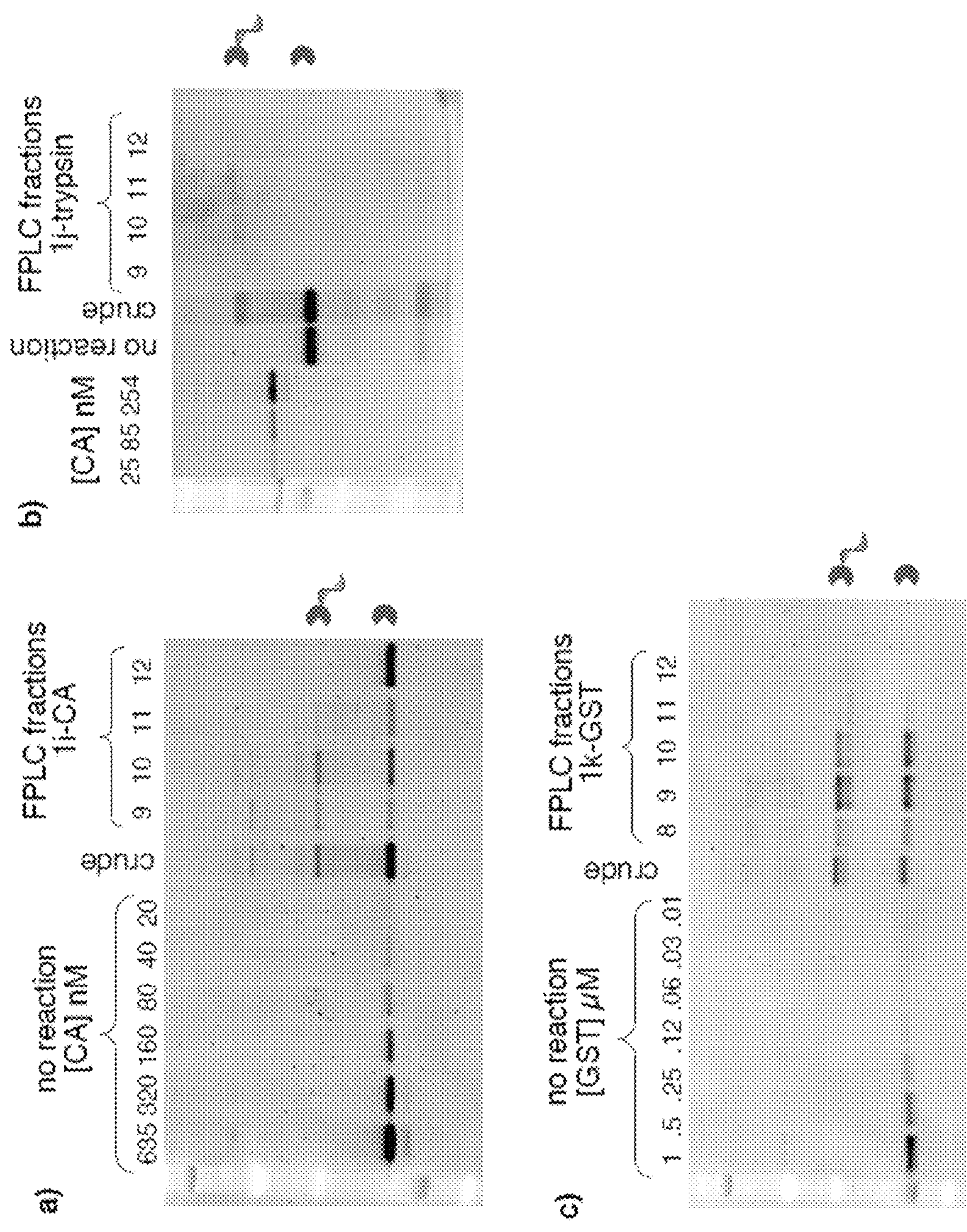
FIG. 27. PAGE characterization of DNA-target conjugates.

PAGE Characterization of DNA-Target Conjugates (FIG. 27).

Protein-DNA conjugates were synthesized and fractionated as described in the Methods section. Protein-DNA conjugates were characterized and quantitated by SDS-PAGE and densitometry. Representative gels are shown here. Aliquots (12 μL) of fractions collected from the FPLC were diluted in 4× NuPAGE Sample Loading Buffer (4 μL) (Invitrogen), heated to 95° C. for 5 minutes and analyzed by electrophoresis (12% Bis-Tris gel, 150V, 45 minutes). The gel was stained with Sypro Ruby Gel Stain and imaged on a Chemilmager. Conjugation of the oligonucleotide to the protein results in the appearance of higher molecular weight bands after conjugation. Protein dilution series standards were used to quantitate the protein-DNA conjugates. (a) Conjugation of 1i to CA. Fractions 9 and 10 were pooled for use in ID-PCR experiments. (b) Conjugation of 1j to trypsin. Fractions 10 and 11 were pooled for use in ID-PCR experiments. (c) Conjugation of 1k to GST. Fractions 8, 9, and 10 were pooled for use in ID-PCR experiments.

TABLE 2

Enrichment factors observed for the five expected interactions as well as the mean enrichment of all 67,599 possible combinations of ligand and target sequences.

| Ligand | Target | Enrichment Factor |
|---|---|---|
| biotin | streptavidin | 860 |
| desthiobiotin | streptavidin | 3078 |
| antipain | trypsin | 331 |
| GLCBS | carbonic anhydrase | 225 |
| CBS | carbonic anhydrase | 75 |
| mean of all enrichment factors | | 1.4 |

TABLE 3

The number of presumed false positives (out of 67,594 possibilities) at a variety of enrichment factor thresholds.

| Enrichment Factor | Number of Presumed False Positives |
|---|---|
| 10 | 1117 |
| 25 | 82 |
| 50 | 7 |
| 75 | 3 |
| 100 | 0 |

Synthesis of Gly-Leu-CBS

Carboxy benzene sulfonamide (20 μmol in 20 μL dry DMF (J. T. Baker), N-hydroxysuccinimide (22 μmol in 22 μL dry DMF), and EDC-HCl (14 μmol in 140 μL dry DMF) were mixed together and stirred at room temperature for 4 hours. The dipeptide H-leucine-glycine-OH (2 μmol in 20 μL dry DMF) and DIPEA (1.2 μL, 8 μmols) were added and the resulting mixture was stirred overnight at room temperature. ESI-MS calculated for $[M-H^+]^-$: 370.41 Found: 369.97. $^1H$ NMR (DMSO-$d^6$, 500 MHz) δ 8.72 (d, 1H, J=8.5 Hz), 8.30 (t, 1H, J=5.5 Hz), 8.09 (d, 2H, J=8 Hz), 7.94 (d, 2H, J=8 Hz), 7.52 (s, 2H), 4.61 (m, 1H), 3.77 (m, 2H), 1.72 (m, 2H), 1.62 (m, 1H), 0.95 (d, 3H, J=6.5 Hz), 0.92 (d, 3H, J=6.5 Hz). $^{13}C$ NMR (DMSO-$d^6$, 125 MHz) δ 173.0, 171.8, 166.0, 147.0, 137.7, 128.9, 126.2, 52.4, 41.5, 41.0, 25.1, 23.8, 22.0.

Primer Extension with Klenow Fragment

An extension mixture consisting of 10×NEB Buffer 2 (2 μL), dNTPs (660 pmol each in 2 μL water), and the target strand (200 fmol in 9 μL PBS) was incubated at 37° C. for 5 minutes. The appropriate ligand strand (200 fmol in 2 μL water) was added and the reaction mixture was incubated at 37° C. for 15 minutes. Klenow fragment exo$^-$ (2.5 U in 5 μL of 1×NEB Buffer 2, New England Biolabs) was added. The primer extension reaction (final volume=20 μL) was incubated at 37° C. for 15 minutes. The polymerase was inactivated by heating to 75° C. for 20 minutes.

Primer Extension Conditions for Aptamer Experiments

The aptamer-DNA conjugate, (1d-aptamer, 1f-aptamer, 1g-aptamer, or 1h-unstructured listed above) (200 pmol), was diluted into 18 μL extension buffer (lx NEB Buffer 2 supplemented with 1 mM $CaCl_2$, 5 mM KCl, and 33 μM dNTPs). This solution was heated to 95° C., then gradually cooled to 37° C. and incubated for 15 minutes. If required, excess small molecule was then added and the resulting solution was incubated for 15 minutes at 37° C. The DNA-ligand conjugate (200 pmol in 2 μL) was added and the resulting solution was incubated for 15 minutes at 37° C. The extension reaction was initiated by the addition of Klenow fragment exo$^-$ (1 U in 2 μL 1×NEB Buffer 2). After 15 minutes, the polymerase was inactivated by heating to 75° C. for 20 minutes.

Quantitative PCR (qPCR) Analysis of Primer Extension Reactions

For each 25 μL qPCR reaction, 12.5 μL of 2×SYBR Green iQ Supermix (Bio-Rad) was combined with 1 μL of 10 μM Primer A, 1 μL of 10 μM Primer B, and 9.5 μL Milli Q $H_2O$. Unless otherwise stated, the primer extension products were diluted 1:100 into $H_2O$ and 1 μL of this solution was added to the mixture described above. Quantitative PCR was performed using a CFX-96 Real-Time System with a C1000 Thermal Cycler (Bio-Rad). PCR conditions: 5 min at 95° C., then 40 cycles of [30 sec at 95° C., 30 sec at 50° C., 30 sec at 72° C.].

Figure 20:
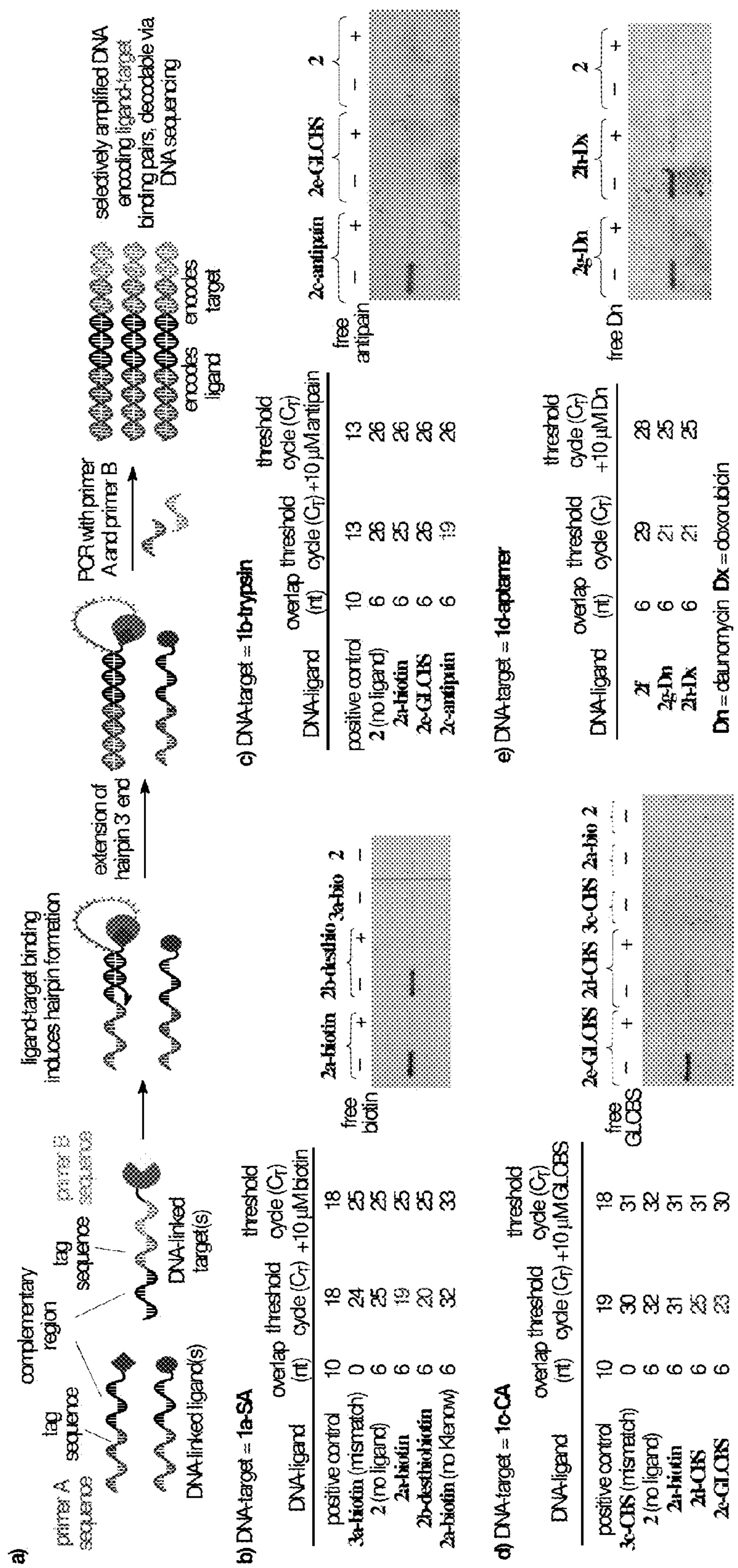
FIG. 20. (a) Overview of ID-PCR. (b) ID-PCR with SA (streptavidin) as the target (1a-SA) and biotin (2a-biotin, $K_d$=40 pM) or desthiobiotin (2b-desthiobiotin, $K_d$=2 nM) as ligands was analyzed by qPCR and PAGE (21 cycles of PCR). ID-PCR reports the interaction of (c) trypsin and antipain ($K_i$=100 nM); (d) CA and carboxy benzene sulfonamide (CBS, $K_i$=3.2 μM) or Gly-Leu-CBS (GLCBS, $K_i$=9 nM); and (e) a DNA aptamer and daunomycin (Dn) (Dn, $K_d$=272 nM) or doxorubicin (Dx). PAGE gels in (c), (d), and (e) show DNA after 20, 24, and 23 cycles of PCR, respectively.
Figure 21:
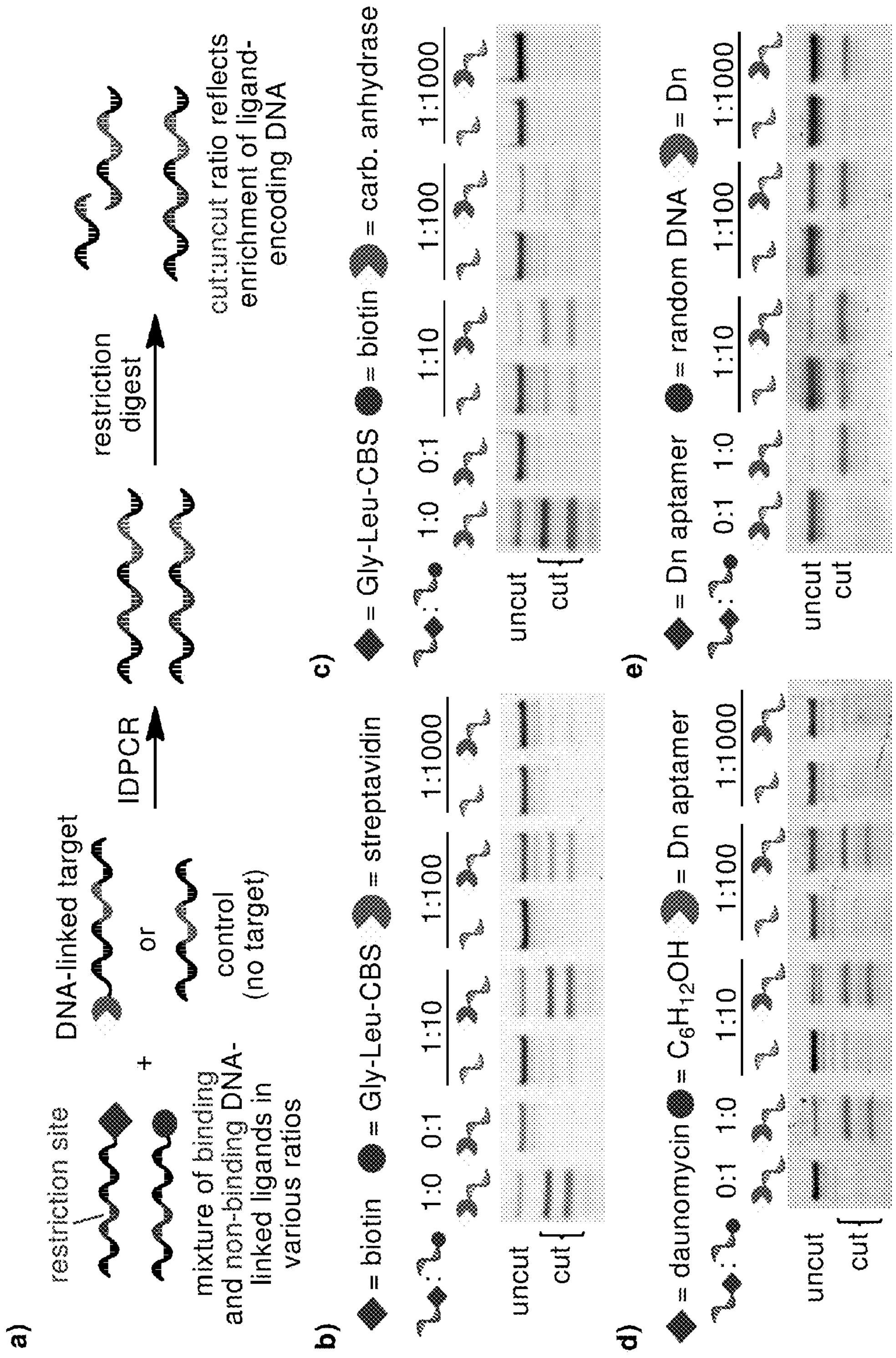
FIG. 21. (a) ID-PCR with a single target in the presence of mock ligand library. (b) Mixtures of 2i-biotin and excess 2k-GLCBS were subjected to ID-PCR with 1a-SA or 1. (c) Mixtures of 2k-GLCBS and excess 2i-biotin were subjected to ID-PCR with 1c-CA or 1. (d) Mixtures of 2n-Dn and excess 2l were subjected to ID-PCR against 1f-aptamer or 1h. (e) Mixtures of 1g-aptamer and excess unstructured DNA (1h) were subjected to ID-PCR with 2g-Dn or 2f. The DNA in (b), (c), (d), and (e) was digested with EcoRI, HindIII, NsiI, or NsiI, respectively.

ID-PCR on Single Target-Ligand Pairs (FIGS. 20 and 21)

All primer extension and qPCR reactions were performed as described above, except that free ligand (200 pmol in 2 μL 10% DMSO) or DMSO (2 μL of 10% DMSO) was added when appropriate. To verify that the observed qPCR threshold cycles correlated with formation of PCR product, we performed gel electrophoresis analyses of PCR reactions halted at the cycle threshold value of the matched ligand-target Klenow extension. Unless otherwise noted, PCR products were analyzed by PAGE on 10% TBE gels at 200 V for 25 minutes staining with ethidium bromide and imaging on a ChemiImager (AlphaInnotech).

The ligand strands, targets, and PCR conditions were as follows. For streptavidin (1a-SA), the following ligand strand sequences were used: positive control, 3a-biotin, 2, 2a-biotin and 2b-desthiobiotin; PCR was performed for 20 cycles (FIG. 20*b*). For trypsin (1b-trypsin), the following ligand strand sequences were used: positive control, 2, 2a-biotin, 2e-GLCBS, and 2c-antipain; PCR was performed for 20 cycles (FIG. 20*c*). For carbonic anhydrase (1c-CA), the following ligand strand sequences were used: positive control, 3b-CBS, 2, 2a-biotin, 2d-CBS and 2e-GLCBS; PCR was performed for 24 cycles (FIG. 20*d*). For the aptamer (1d-aptamer), the following sequences were used: 2f, 2g-Dn, and 2h-Dx; PCR was performed for 23 cycles (FIG. 20*e*). In this case, the products were stained with SYBRI (Invitrogen) and imaged on a Typhoon Trio Imager (Amersham).

In order to investigate the enrichment of DNA encoding ligand-target pairs in the presence of excess non-binding ligand conjugates, a series of ID-PCR experiments were conducted with mixtures of binding conjugate and non-binding conjugates (see FIG. 21). These mixtures were subjected to Klenow extension either in the presence of the target conjugate (the "selection" case) or a target strand lacking protein (the "negative control" case). Primer extension reactions were performed with constant concentrations of a non-binding ligand-DNA conjugate (10 nM) and varying concentrations of a binding ligand-DNA conjugate (1 nM, 100 pM, 10 pM). The appropriate cycle number for each reaction was determined by qPCR evaluation, such that preparative PCR reactions (50 μL total volume) were stopped in the exponential amplification phase, in order to minimize dynamic compression during PCR. An aliquot (16 μL) of the PCR reaction mixture was then incubated with the appropriate restriction enzyme (FIG. 21*b*: EcoRI: FIG. 21*c*: HindIII; FIG. 21*d,e*: NsiI). All restriction enzymes were purchased from New England Biolabs. The resulting samples were analyzed by PAGE as described above (10% TBE, 200 V, 25 minutes).

FIG. 21*b*:

| Binding | Non-binding | Ratio | Target Strand | PCR Cycles | Gel Lane |
|---|---|---|---|---|---|
| 2i-biotin | — | 1:0 | 1a-SA | 22 | 1 |
| — | 2k-GLCBS | 0:1 | 1a-SA | 26 | 2 |
| 2i-biotin | 2k-GLCBS | 1:10 | 1 | 32 | 3 |
| 2i-biotin | 2k-GLCBS | 1:10 | 1a-SA | 22 | 4 |
| 2i-biotin | 2k-GLCBS | 1:100 | 1 | 32 | 5 |
| 2i-biotin | 2k-GLCBS | 1:100 | 1a-SA | 25 | 6 |
| 2i-biotin | 2k-GLCBS | 1:1000 | 1 | 32 | 7 |
| 2i-biotin | 2k-GLCBS | 1:1000 | 1a-SA | 26 | 8 |

FIG. 21*c*:

| Binding | Non-binding | Ratio | Target Strand | PCR Cycles | Gel Lane |
|---|---|---|---|---|---|
| 2k-GLCBS | — | 1:0 | 1c-CA | 25 | 1 |
| — | 2i-biotin | 0:1 | 1c-CA | 32 | 2 |
| 2k-GLCBS | 2i-biotin | 1:10 | 1 | 30 | 3 |
| 2k-GLCBS | 2i-biotin | 1:10 | 1c-CA | 25 | 4 |
| 2k-GLCBS | 2i-biotin | 1:100 | 1 | 30 | 5 |
| 2k-GLCBS | 2i-biotin | 1:100 | 1c-CA | 28 | 6 |
| 2k-GLCBS | 2i-biotin | 1:1000 | 1 | 30 | 7 |
| 2k-GLCBS | 2i-biotin | 1:1000 | 1c-CA | 31 | 8 |

FIG. 21*d*:

| Binding | Non-binding | Ratio | Target Strand | PCR Cycles | Gel Lane |
|---|---|---|---|---|---|
| — | 21 | 0:1 | 1f-aptamer | 28 | 1 |
| 2n-Dn | — | 1:0 | 1f-aptamer | 20 | 2 |
| 2n-Dn | 21 | 1:10 | 1h-unstructured | 28 | 3 |
| 2n-Dn | 21 | 1:10 | 1f-aptamer | 24 | 4 |
| 2n-Dn | 21 | 1:100 | 1h-unstructured | 28 | 5 |
| 2n-Dn | 21 | 1:100 | 1f-aptamer | 28 | 6 |
| 2n-Dn | 21 | 1:1000 | 1h-unstructured | 28 | 7 |
| 2n-Dn | 21 | 1:1000 | 1f-aptamer | 28 | 8 |

FIG. 21*e*:

| Binding | Non-binding | Ratio | Target Strand | PCR Cycles | Gel Lane |
|---|---|---|---|---|---|
| — | 1h-unstructured | 0:1 | 2g-Dn | 30 | 1 |
| 1f-aptamer | — | 1:0 | 2g-Dn | 21 | 2 |
| 1f-aptamer | 1h-unstructured | 1:10 | 2f | 30 | 3 |
| 1f-aptamer | 1h-unstructured | 1:10 | 2g-Dn | 25 | 4 |
| 1f-aptamer | 1h-unstructured | 1:100 | 2f | 30 | 5 |

-continued

| Binding | Non-binding | Ratio | Target Strand | PCR Cycles | Gel Lane |
|---|---|---|---|---|---|
| 1f-aptamer | 1h-unstructured | 1:100 | 2g-Dn | 28 | 6 |
| 1f-aptamer | 1h-unstructured | 1:1000 | 2f | 22* | 7 |
| 1f-aptamer | 1h-unstructured | 1:1000 | 2g-Dn | 22* | 8 |

*indicates samples that were not diluted 100-fold prior to qPCR

Figure 22:
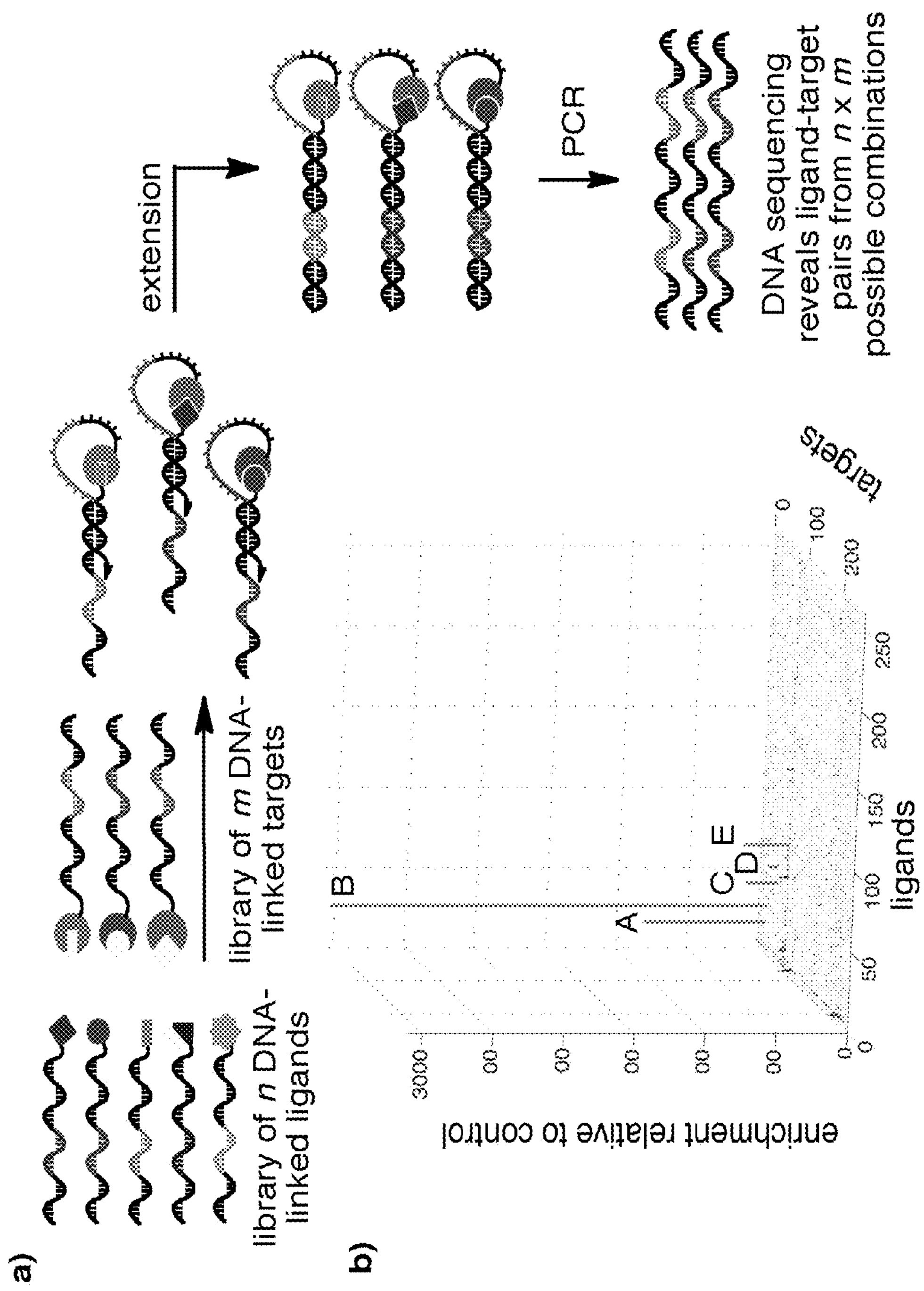
FIG. 22. (a) A model library of DNA-encoded ligands mixed with a model library of DNA-encoded targets allows multiplexed detection of binding pairs. (b) ID-PCR was used to perform a model selection on an equimolar 261-membered DNA-ligand library and an equimolar 259-member DNA-target library containing five known protein-ligand pairs out of 67,599 possible combinations. For each protein target, the most highly enriched sequences (A-E) relative to a control lacking proteins corresponded to the known protein-ligand pairs, labeled A-E in the plot. A: biotin+SA; B: desthiobiotin+SA; C: GLCBS+CA; D: CBS+CA; E: trypsin+antipain.

ID-PCR of a Ligand Library and Target Library in a Single Solution (FIG. 22)

Primer extension was performed with ligand sequences (40 pM each 2i-biotin, 2q-desthiobiotin, 2s-GLCBS, 2o-CBS, and 2u-antipain and 9.8 nM 2v) and target sequences (60 pM each 1a-SA, 1i-CA and 1j-trypsin and 9.8 nM 1k-GST) such that the reaction contained an equimolar quantity of each of 261 ligand sequences and 259 target sequences. A control primer extension reaction was also performed using the same pool of ligand strands, but with a pool of target strands lacking conjugated proteins (1, 1i, 1j, 60 pM each and 1k, 9.8 nM). Adapter sequences required for Illumina sequencing, as well as barcodes identifying the input and selection experiments, were installed by PCR with either Primer C (input control) or Primer D (selection) and Primer E. The appropriate cycle number for each reaction was determined by qPCR evaluation, such that preparative PCR reactions (50 μL total volume) were stopped in the exponential amplification phase in order to minimize dynamic compression during PCR. PCR product was purified by gel (3% agarose, 200V, 20 min followed by Qiagen Extraction Kit), quantitated using PicoGreen (Invitrogen), and pooled in equimolar amounts (10 nM total DNA) for sequencing. Sequencing was performed on an Illumina (Solexa) Genome Analyzer II (FAS Center for Systems Biology, Harvard University).

Approximately 500,000 sequence reads were obtained after sequencing and data processing using MATLAB (The MATLAB script was run on the Odyssey Cluster supported by the FAS Sciences Division Research Computing Group.): 286,784 from the selection experiment, and 189,133 from the control (no protein) experiment. Due to the large number of possible sequences, many of the 67,599 possible sequences were not observed. A value of 1 was therefore added to the number of observed counts in the input and selection datasets for every sequence. The observed sequence counts were normalized (results from selection were divided by 286,784 and results from control were divided by 189,133). Enrichment factors were determined by dividing the fraction of total counts observed for each sequence after selection by the fraction of total counts observed for that sequence in the input control. The resulting set of enrichment factors are plotted in FIG. 21 and described in Tables 2 and 3.

FIG. 25 shows Ligand-Target Affinity Measurements. FIGS. 25 *a* and *b* show ligand-target affinity measurements of a CBS, 2d-CBS, GLCBS and 2s-GLCBS/carbonic anhydrase complex. Enzymatic activity was measured by adopting a previously described method:[16] carbonic anhydrase (20 pmol for CBS and 2d-CBS, 4 pmol for GLCBS and 2s-GLCBS) was diluted in 180 μL assay buffer (PBS, 5% DMSO) and incubated with various concentrations of inhibitor for 10 minutes at room temperature and then for 5 minutes at 37° C. before addition of a chromogenic substrate, 4-nitrophenyl acetate (2 mmol in 20 μL acetonitrile). The change in absorbance signal (400 nm) was measured over 10 minutes at 37° C. using a SpectraMax microplate reader. The data obtained at various inhibitor concentrations was plotted and the $K_i$ was determined by fitting the equation below.

FIG. 25 *d* shows ligand-target affinity measurements of a Antipain, 2e-antipain/trypsin complex. Conditions were adopted from a previously reported protocol.[17] Trypsin (200 fmol) was diluted in 90 μL PBS and was incubated with various concentrations of antipain, a known inhibitor of tryptic proteolysis, or 2e-antipain. The solution was equilibrated at room temperature for 10 minutes and at 35° C. for 5 minutes before addition of the fluorogenic proteolytic substrate Z-Arg-AMC (Bachem) (10 nmol in 10 μL 50% DMSO) (final volume=100 μL). The change in fluorescence signal (ex: 383 nm; em: 455 nm; cutoff filter: 420 nm) was measured over 10 minutes at 35° C. using a SpectraMax microplate reader, and fitting of results obtained at various concentrations of inhibitor enabled determination of $K_i$ (see equation below).

Equation Used to Fit $K_i$ from Inhibitory Curves (FIGS. 25*a*, *b*, *d*).

The $K_i$ was determined by fitting the following equation to the plot of normalized activity vs. inhibitor concentration: $V_o$=c+d(([E]$_{tot}$+[i]$_{tot}$+K$_i$)−sqrt((−[E]$_{tot}$−[I]$_{tot}$−K$_i$)^2−4*[E]$_{tot}$*[I]$_{tot}$))/(2*[E]$_{tot}$), where $V_o$ is initial reaction velocity, $[E]_{tot}$ is total enzyme concentration, $[I]_{rot}$ is total inhibitor concentration; c and d are variable parameters for the maximum $V_o$ and for the difference between the minimum and maximum $V_o$, respectively.

FIG. 25 *c* shows measurement of 2b-desthiobiotin/streptavidin complex by gel shift. The DNA-ligand conjugate 2b-desthiobiotin was hybridized to a complementary 20-mer carrying a Cy3 label at the 3'-end. The resulting duplex (10 nM) was incubated with increasing concentrations of streptavidin in binding buffer (145 mM NaCl, 10 mM Tris/HCl, 10 mM $MgCl_2$, 7 mM $Na_2PO_4$, 1.9 mM KCl, 1 mM dithiothreitol, pH 7.4), for 1 h and analyzed on a 20% TBE polyacrylamide gel. The appearance of a higher molecular weight band indicated formation of a streptavidin-2b-desthiobiotin complex. The apparent $K_d$ was determined from the streptavidin concentration for which the bands corresponding to free DNA and to the complex were of approximately equal intensity.

REFERENCES (1) a) Inglese, J.; Johnson, R. L.; Simeonov, A.; Xia, M.; Zheng, W.; Austin, C. P.; Auld, D. S. Nat. Chem. Biol. 2007, 3, 466. b) Zhu, Z.; Cuozzo, J. J. Biomol. Screening 2009, 14, 1157.

(2) Vijayendran, R. A.; Leckband, D. E. Anal. Chem. 2001, 73, 471.

(3) Gorin, D. J.; Kamlet, A. S.; Liu, D. R. J. Am. Chem. Soc. 2009, 131, 9189.

(4) Green, N. M. Methods in Enzymol. 1990, 184, 62.

(5) Dumelin, C. E.; Scheuermann, J.; Melkko, S.; Neri, D. Bioconjugate Chem. 2006, 17, 366.

(6) Torreggiani, A.; Fini, G. Biospectroscopy 1998, 4, 197.

(7) Otto, H. H.; Schirmeister, T. Chem. Rev. 1997, 97, 133.

(8) West, G. M.; Tang, L.; Fitzgerald, M. C. Anal. Chem. 2008, 80, 4175.

(9) Mincione, F.; Starnotti, M.; Menabuoni, L.; Scozzafava, A.; Casini, A.; Supuran, C. T. Bioorg. Med. Chem. Lett. 2001, 11, 1787.

(10) a) Ellington, A. D.; Szostak, J. W. Nature 1990, 346, 818. b) Robertson, D. L.; Joyce, G. F. Nature 1990, 344, 467. c) Tuerk, C.; Gold, L. Science 1990, 249, 505. For a general review see: d) Wilson, D. S.; Szostak, J. W. Annu. Rev. in Biochem. 1999, 68, 611.

(11) Wochner, A.; Menger, M.; Orgel, D.; Cech, B.; Rimmele, M.; Erdmann, V. A.; Gloekler, J. Anal. Biochem. 2008, 373, 34.

(12) Melkko, S.; Scheuermann, J.; Dumelin, C. E.; Neri, D. Nat. Biotechnol. 2004, 22, 568

(13) Sprinz, K. I.; Tagore, D. M.; Hamilton, A. D. Bioorg. Med. Chem. Lett. 2005, 15, 3908.

(14) a) Bowley, D. R.; Jones, T. M.; Burton, D. R.; Lerner, R. A. P. Natl. Acad. Sci. U.S.A 2009, 106, 1380. b) Fredriksson, S.; Gullberg, M.; Jarvius, J.; Olsson, C.; Pietras, K.; Gustafsdottir, S. M.; Ostman, A.; Landegren, U. Nat. Biotechnol. 2002, 20, 473. c) Hofstadler, S. A.; Griffey, R. H. Chem. Rev. 2001, 101, 377.

(15) a) Clark, M. A. et al. Nat. Chem. Biol. 2009, 1. b) Mannocci, L.; Zhang, Y.; Scheuermann, J.; Leimbacher, M.; De Bellis, G.; Rizzi, E.; Dumelin, C. E.; Melkko, S.; Neri, D. P. Natl. Acad. Sci. U.S.A. 2008, 105, 17670. c) Gorska, K.; Huang, K.-T.; Chaloin, O.; Winssinger, N. Angew. Chem. Int. Ed. 2009, 48, 7695. d) Halpin, D. R.; Harbury, P. B. PLoS Biol. 2004, 2, 1022. e) Hansen, M. H.; Blakskjaer, P.; Petersen, L. K.; Hansen, T. H.; Hojfeldt, J. W.; Gothelf, K. V.; Hansen, N. J. V. J. Am. Chem. Soc. 2009, 131, 1322. f) Kanan, M. W.; Rozenman, M. M.; Sakurai, K.; Snyder, T. M.; Liu, D. R. Nature 2004, 431, 545. g) Kleiner, R. E.; Dumelin, C. E.; Tiu, G. C.; Sakurai, K.; Liu, D. R. J. Am. Chem. Soc. 2010, 1. h) Tse, B. N.; Snyder, T. M.; Shen, Y.; Liu, D. R. J. Am. Chem. Soc. 2008, 130, 15611. i) Doyon, J. B.; Snyder, T. M.; Liu, D. R. J. Am. Chem. Soc. 2003, 125, 12372. j) Gartner, Z. J.; Liu, D. R. J. Am. Chem. Soc. 2001, 123, 6961. k) Gartner, Z. J.; Tse, B. N.; Grubina, R.; Doyon, J. B.; Snyder, T. M.; Liu, D. R. Science 2004, 305, 1601.1) Clark, M. A.; Acharya, R. A.; Arico-Muendel, C. C.; Belyanskaya, S. L.; Benjamin, D. R.; Carlson, N. R.; Centrella, P. A.; Chiu, C. H.; Creaser, S. P.; Cuozzo, J. W.; Davie, C. P.; Ding, Y.; Franklin, G. J.; Franzen, K. D.; Gefter, M. L.; Hale, S. P.; Hansen, N. J. V.; Israel, D. I.; Jiang, J.; Kavarana, M. J.; Kelley, M. S.; Kollmann, C. S.; Li, F.; Lind, K.; Mataruse, S.; Medeiros, P. F.; Messer, J. A.; Myers, P.; O'keefe, H.; Oliff, M. C.; Rise, C. E.; Satz, A. L.; Skinner, S. R.; Svendsen, J. L.; Tang, L.; Van Vloten, K.; Wagner, R. W.; Yao, G.; Zhao, B.; Morgan, B. A. Nat. Chem. Biol. 2009, 5, 647.

(16) Pocker, Y.; Stone, J. T. Biochemistry 1967, 6, 668.

(17) Melkko, S.; Zhang, Y.; Dumelin, C. E.; Scheuermann, J.; Neri, D. Angew. Chem. Int. Ed. 2007, 46, 4671.

(18) Jain, A.; Whitesides, G. M.; Alexander, R. S.; Christianson, D. W. J. Med. Chem. 1994, 37, 2100.

(19) Mincione, F.; Starnotti, M.; Menabuoni, L.; Scozzafava, A.; Casini, A.; Supuran, C. T. Bioorg. Med. Chem. Lett. 2001, 11, 1787.

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method for reactivity-dependent polymerase chain reaction, comprising:

(i) providing a nucleic acid template, wherein the nucleic acid template comprises:

a first primer hybridization site, optionally, a sequence tag, a second primer hybridization site, and a candidate reactive moiety;

(ii) contacting the nucleic acid template with a first primer, wherein the first primer comprises:

a sequence complementary to the first primer hybridization site, a third primer hybridization site, and a target reactive moiety;

(iii) incubating the nucleic acid template contacted with the first primer under conditions suitable for the candidate reactive moiety to form a covalent bond with the target reactive moiety;

(iv) incubating the nucleic acid template contacted with the first primer under conditions suitable for covalently bound first primer to hybridize with the first primer hybridization site of the nucleic acid template it is covalently bound to and for primer extension;

(v) contacting the nucleic acid template contacted with the first primer with a PCR primer complementary to the second primer hybridization site and a PCR primer complementary to the third primer hybridization site or with a PCR primer complementary to the second and third primer hybridization site; and (vi) performing a polymerase chain reaction to amplify the nucleic acid template or a fragment thereof.

2. A method for reactivity-dependent polymerase chain reaction, comprising:

(i) providing a first nucleic acid molecule, wherein the first nucleic acid molecule comprises a first primer hybridization site, a second primer hybridization site optionally, a sequence tag, and a candidate reactive moiety;

(ii) contacting the first nucleic acid molecule with a second nucleic acid molecule, wherein the second nucleic acid molecule comprises a nucleic acid sequence complementary to the first primer hybridization site of the first nucleic acid molecule, and a third primer hybridization site, and a target reactive moiety;

(iii) incubating the first nucleic acid molecule contacted with the second nucleic acid molecule under conditions suitable for the candidate reactive moiety to form a covalent bond with the target reactive moiety;

(iv) incubating the first nucleic acid molecule covalently bound to the second nucleic acid molecule under conditions suitable for hybridization of the nucleic acid sequence complementary to the first primer hybridization site to the first primer hybridization site and for primer extension;

(v) contacting the first nucleic acid molecule covalently bound to the second nucleic acid molecule with a primer complementary to the second primer hybridization site and a primer complementary to the third primer hybridization site; and (vi) performing a polymerase chain reaction (PCR) to amplify the nucleic acid template or a fragment thereof.

3. A method for reactivity-dependent polymerase chain reaction, comprising:

(i) providing a first nucleic acid molecule, wherein the first nucleic acid molecule comprises a first primer hybridization site, optionally, a sequence tag adjacent to the first primer hybridization site, optionally, a restriction site adjacent to the sequence tag, and a candidate reactive moiety;

(ii) contacting the first nucleic acid molecule with a second nucleic acid molecule, wherein the second nucleic acid molecule comprises a nucleic acid sequence complementary to the first primer hybridization site of the first nucleic acid molecule, a third primer hybridization site, and a target reactive moiety;

(iii) incubating the first nucleic acid molecule contacted with the second nucleic acid molecule under conditions suitable for the candidate reactive moiety to form a covalent bond with the target reactive moiety;

(iv) incubating the first nucleic acid molecule covalently bound to the second nucleic acid molecule under conditions suitable for hybridization of the nucleic acid sequence complementary to the first primer hybridization site to the first primer hybridization site and for primer extension;

(v) optionally, contacting the first nucleic acid molecule covalently bound to the second nucleic acid molecule with a restriction enzyme under conditions suitable for restriction enzyme digest;

(vi) contacting the first nucleic acid molecule covalently bound to the second nucleic acid molecule with a nucleic acid linker, wherein the linker comprises a second primer hybridization site;

(vii) incubating the first nucleic acid contacted with the linker under conditions suitable to ligate the linker to the first nucleic acid molecule;

(viii) contacting the first nucleic acid molecule contacted with the second nucleic acid molecule with a PCR primer complementary to the second primer hybridization site and a PCR primer complementary to the third primer hybridization site; and (ix) performing a polymerase chain reaction (PCR) to amplify the nucleic acid template or a portion thereof.

4. The method of claim 1, wherein the first primer hybridization site is between 5 and 16 nucleotides long.

5. The method of claim 1, wherein the second and the third primer hybridization site comprise the same nucleic acid sequence.

6. The method of claim 1, wherein the primer complementary to the second primer hybridization site and the primer complementary to the third primer hybridization site comprise the same nucleic acid sequence.

7. The method of claim 1, wherein the second and the third primer hybridization site comprise different nucleic acid sequences.

8. The method of claim 1, wherein the first primer hybridization site and the third primer hybridization site overlap or are identical.

9. The method of claim 1, wherein the sequence tag sequence is 5-30 nucleotides long.

10. The method of claim 1, wherein the candidate and/or the target reactive moiety is a functional group selected from the group consisting of alkenyl, alkynyl, phenyl, benzyl, halo, haloformyl, hydroxyl, carbonyl, aldehyde, carbonate ester, carboxylate, carboxyl, ether, ester, carboxyamide, amine, ketimine, aldimine, imide, azido, diimide, cyanate, isocyanide, isocyanate, isothiocyanate, nitrile, sulfide, and disulfide groups.

11. The method of claim 1, wherein the covalent bond formed between the candidate and the target reactive moiety is an amide bond, an acyl bond, a disulfide bond, an alkyl bond, an ether bond, or an ester bond.

12. The method of claim 1, wherein the covalent bond formed between the candidate and the target reactive moiety is a carbon-carbon bond, a carbon-oxygen bond, a carbon-nitrogen bond, a carbon-sulfur bond, a sulfur-sulfur bond, a carbon-phosphorus bond, a phosphorus-oxygen bond, a phosphorus-nitrogen bond.

13. The method of claim 1, wherein the covalent bond between the candidate and the target reactive moiety is formed by an acylation, an addition, a nucleophilic substitution, a Huisgen cycloaddition, a carbonyl chemistry reaction, a "non aldol"-type carbonyl chemistry reaction, or an addition to carbon-carbon double or triple bonds.

14. The method of claim 1, further comprising contacting the first nucleic acid molecule contacted with the second nucleic acid molecule with a catalyst or reagent catalyzing a covalent bond-forming reaction between the candidate reactive moiety and the target reactive moiety under suitable conditions.

15. The method of claim 1, further comprising contacting the nucleic acid template contacted with the first primer with a catalyst or reagent catalyzing a covalent bond-forming reaction between the candidate reactive moiety and the target reactive moiety under suitable conditions.

16. The method of claim 1, wherein the conditions suitable for hybridization of the nucleic acid sequence complementary to the first primer hybridization site to the first primer hybridization site and primer extension are conditions not allowing for efficient primer site hybridization and primer extension of the first and second nucleic acid molecules not connected by a covalent bond.

17. The method of claim 1, wherein the conditions suitable for hybridization of the nucleic acid sequence complementary to the first primer hybridization site to the first primer hybridization site and primer extension are conditions not allowing for efficient primer site hybridization and primer extension of first primer not covalently bound to the nucleic acid template.

18. The method of claim 1, wherein the PCR is quantitative, real-time PCR.

19. A method for reactivity-dependent polymerase chain reaction screening of a reactive moiety library, comprising:

(i) providing a library of nucleic acid templates, wherein each nucleic acid template comprises:

a first primer hybridization site, a sequence tag, and a second primer hybridization site, and a candidate reactive moiety, and wherein the candidate reactive moiety of any specific nucleic acid template can be identified by its sequence tag sequence;

(ii) contacting the nucleic acid templates of said library with a first primer comprising:

a sequence complementary to the first primer hybridization site, a third primer hybridization site, and a target reactive moiety;

(iii) incubating the nucleic acid templates contacted with the first primer under conditions suitable for the candidate reactive moiety to form a covalent bond with the target reactive moiety;

(iv) incubating the nucleic acid templates of the library contacted with the first primer under conditions suitable for covalently bound first primer to hybridize with the first primer hybridization site of the nucleic acid template it is covalently bound to and for primer extension;

(v) contacting the nucleic acid templates contacted with the first primer with a PCR primer complementary to the second primer hybridization site and a PCR primer complementary to the third primer hybridization site, or a PCR primer complementary to the second and the third primer hybridization site; and (vi) performing a polymerase chain reaction amplifying a nucleic acid template sequence tag identifying a candidate reactive moiety able to form a covalent bond to the second reactive moiety.

20. A method for reactivity-dependent polymerase chain reaction, comprising:

(i) providing a nucleic acid template, wherein the nucleic acid template comprises a first primer hybridization site, optionally, a sequence tag, a second primer hybridization site, and a reactive moiety;

(ii) contacting the nucleic acid template with a first primer, wherein the first primer comprises:

a sequence complementary to the first primer hybridization site, a third primer hybridization site, and a reactive moiety;

(iii) incubating the nucleic acid template contacted with the first primer under conditions suitable for the candidate reactive moiety to form a covalent bond with the target reactive moiety either only in the presence or only in the absence of an environmental parameter or analyte;

(iv) incubating the nucleic acid template contacted with the first primer under conditions suitable for covalently bound first primer to hybridize with the first primer hybridization site of the nucleic acid template it is covalently bound to and for primer extension;

(v) contacting the nucleic acid template contacted with the first primer with a PCR primer complementary to the second primer hybridization site and a PCR primer complementary to the third primer hybridization site or with a PCR primer complementary to the second and third primer hybridization site; and (vi) performing a polymerase chain reaction to amplify the nucleic acid template, or a fragment thereof.

* * * * *

SEQUENCE LISTING

```
<160> NUMBER OF SEQ ID NOS: 96

<210> SEQ ID NO 1
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 1

Ala Pro Gly Phe Ala
1               5


<210> SEQ ID NO 2
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 2

gcagtaccaa ccctgtacac catctcaagt tctatgtctg actacagagt gggatgcata     60

gaac                                                                  64


<210> SEQ ID NO 3
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 3

tctgactaca gagtgggatg catagaac                                        28


<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4

gctgactaca gagtgggatg                                                 20


<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5

gcagtaccaa ccctgtacac                                                 20


<210> SEQ ID NO 6
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 6
```

gcagtaccaa ccctgtacac catctcaagt tctatg 36

<210> SEQ ID NO 7
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 7
gctgactaca gagtgggatg catagaactt 30

<210> SEQ ID NO 8
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 8
gctgactaca gagtgggatg catagaac 28

<210> SEQ ID NO 9
<211> LENGTH: 66
<212> TYPE: DNA
<213> ORGANISM: Artificial Sequence
<220> FEATURE:
<223> OTHER INFORMATION: synthetic polynucleotide

<400> SEQUENCE: 9
gcagtaccaa ccctgtacac catctcaagt tctatggctg actacagagt gggatgcata 60
gaactt 66

<210> SEQ ID NO 10
<211> LENGTH: 64
<212> TYPE: DNA
<213> ORGANISM: Artificial Sequence
<220> FEATURE:
<223> OTHER INFORMATION: synthetic polynucleotide

<400> SEQUENCE: 10
gcagtaccaa ccctgtacac catctcaagt tctatggctg actacagagt gggatgcata 60
gaac 64

<210> SEQ ID NO 11
<211> LENGTH: 62
<212> TYPE: DNA
<213> ORGANISM: Artificial Sequence
<220> FEATURE:
<223> OTHER INFORMATION: synthetic polynucleotide

<400> SEQUENCE: 11
gcagtaccaa ccctgtacac catctcaagt tctatggctg actacagagt gggatgcata 60
ga 62

<210> SEQ ID NO 12
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 12
gcagtaccaa ccctgtacac 20

<210> SEQ ID NO 13
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 13
cctgactaca gagtgggatg 20

<210> SEQ ID NO 14
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 14
gcagtaccaa ccctgtacac catctcaagt tctatg 36

<210> SEQ ID NO 15
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 15
cctgactaca gagtgggatg catagaac 28

<210> SEQ ID NO 16
<211> LENGTH: 29
<212> TYPE: DNA
<213> ORGANISM: Artificial Sequence
<220> FEATURE:
<223> OTHER INFORMATION: synthetic polynucleotide

<400> SEQUENCE: 16
cctgactaca gagtgggatg catagaatt 29

<210> SEQ ID NO 17
<211> LENGTH: 66
<212> TYPE: DNA
<213> ORGANISM: Artificial Sequence
<220> FEATURE:
<223> OTHER INFORMATION: synthetic polynucleotide

<400> SEQUENCE: 17
gcagtaccaa ccctgtacac catctcaagt tctatgcctg actacagagt gggatgcata 60
gaactt 66

<210> SEQ ID NO 18
<211> LENGTH: 64
<212> TYPE: DNA
<213> ORGANISM: Artificial Sequence
<220> FEATURE:
<223> OTHER INFORMATION: synthetic polynucleotide

<400> SEQUENCE: 18
gcagtaccaa ccctgtacac catctcaagt tctatgcctg actacagagt gggatgcata 60
gaac 64

<210> SEQ ID NO 19
<211> LENGTH: 62
<212> TYPE: DNA
<213> ORGANISM: Artificial Sequence
<220> FEATURE:
<223> OTHER INFORMATION: synthetic polynucleotide

<400> SEQUENCE: 19
gcagtaccaa ccctgtacac catctcaagt tctatgcctg actacagagt gggatgcata 60
ga 62

<210> SEQ ID NO 20
<211> LENGTH: 43
<212> TYPE: DNA
<213> ORGANISM: Artificial Sequence
<220> FEATURE:
<223> OTHER INFORMATION: synthetic polynucleotide

<400> SEQUENCE: 20
gagctcgttg atatccgcag acatgagccc cactacacac acc 43

<210> SEQ ID NO 21
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 21
acctaaagct agcagctggc cgtgatcagc ttggtgtgtg 40

<210> SEQ ID NO 22
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 22
gagctcgttg atatccgcag 20

<210> SEQ ID NO 23
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 23
acctaaagct agcagctggc 20

<210> SEQ ID NO 24
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 24
gcagtaccaa ccctgtacac catctcaagt tctatg 36

<210> SEQ ID NO 25
<211> LENGTH: 30
<212> TYPE: DNA
<213> ORGANISM: Artificial Sequence
<220> FEATURE:

<223> OTHER INFORMATION: synthetic polynucleotide

<400> SEQUENCE: 25
ctgagctcgt tgatatccgc agcatagaac 30

<210> SEQ ID NO 26
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 26
gcagtaccaa ccctgtacac 20

<210> SEQ ID NO 27
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 27
ctgagctcgt tgatatccgc ag 22

<210> SEQ ID NO 28
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 28
gcagtaccaa ccctgtacac catctcaagt tctatc 36

<210> SEQ ID NO 29
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 29
cctgactaca gagtgggatg catagaac 28

<210> SEQ ID NO 30
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 30
cctgactaca gagtgggatg ttgaccgt 28

<210> SEQ ID NO 31
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 31
gctgactaca gagtgggatg 20

<210> SEQ ID NO 32
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 32
ctgagctcgt tgatatccgc ag 22

<210> SEQ ID NO 33
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 33
gctgactaca gagtgggatg aatcttcatc tcaagttcta tg 42

<210> SEQ ID NO 34
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 34
ctgagctcgt tgatatccgc agcatagaac 30

<210> SEQ ID NO 35
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 35
gctgactaca gagtgggatg aagcttcatc tcaagttcta tgctgagctc gttgatatcc 60
gcagcataga ac 72

<210> SEQ ID NO 36
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 36
gctgactaca gagtgggatg caagtgcatc tcaagttcta tg 42

<210> SEQ ID NO 37
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 37
gctgactaca gagtgggatg cagctgcatc tcaagttcta tgctgagctc gttgatatcc 60
gcagcataga ac 72

<210> SEQ ID NO 38
<211> LENGTH: 43
<212> TYPE: DNA

<213> ORGANISM: Artificial Sequence
<220> FEATURE:
<223> OTHER INFORMATION: synthetic polynucleotide

<400> SEQUENCE: 38
gagctcgttg atatccgcag agcgttatgg tccgacacac acc 43

<210> SEQ ID NO 39
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 39
acctaaagct agcagctggc gaggttccag atggtgtgtg 40

<210> SEQ ID NO 40
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 40
acctaaagct agcagctggc cgcacacttt ctggtgtgtg 40

<210> SEQ ID NO 41
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 41
gagctcgttg atatccgcag 20

<210> SEQ ID NO 42
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 42
acctaaagct agcagctggc 20

<210> SEQ ID NO 43
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 43
gagctcgttg atatccgcag 20

<210> SEQ ID NO 44
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 44
acctaaagct agcagctggc 20

<210> SEQ ID NO 45
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 45
gcagtaccaa ccctgtacac 20

<210> SEQ ID NO 46
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 46
ctgagctcgt tgatatccgc ag 22

<210> SEQ ID NO 47
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 47
gcagtaccaa ccctgtacac catctcaagt tctatg 36

<210> SEQ ID NO 48
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 48

Ala Pro Gly Phe Ala
1               5

<210> SEQ ID NO 49
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 49
ctgagctcgt tgatatccgc agcatagaac 30

<210> SEQ ID NO 50
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 50
gcagtaccaa ccctgtacac catctcaagt tctatg 36

<210> SEQ ID NO 51
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 51
cggcgatcgt gaaggaggct agactgagtg ag 32

<210> SEQ ID NO 52
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 52
cggcgatcgt gaaggaggct agactgagtg ag 32

<210> SEQ ID NO 53
<211> LENGTH: 45
<212> TYPE: DNA
<213> ORGANISM: Artificial Sequence
<220> FEATURE:
<223> OTHER INFORMATION: synthetic polynucleotide

<400> SEQUENCE: 53
tggatcgtga tgactgtccc gacaagcata cgtatctcac tcagt 45

<210> SEQ ID NO 54
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 54
tggatcgtga tgactgtccc gacaagcata cgtatctcac t 41

<210> SEQ ID NO 55
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 55
tggatcgtga tgactgtccc gacaagcata cgtatctcac t 41

<210> SEQ ID NO 56
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 56
tggatcgtga tgactgtccc gacaagcata cgtattacta g 41

<210> SEQ ID NO 57
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 57
tggatcgtga tgactgtccc gacaagcata cgtatctcac t 41

<210> SEQ ID NO 58
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 58
tggatcgtga tgactgtccc gacaagcata cgtatctcac t 41

<210> SEQ ID NO 59
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 59
tggatcgtga tgactgtccc gacaagcata cgtattacta g 41

<210> SEQ ID NO 60
<211> LENGTH: 68
<212> TYPE: DNA
<213> ORGANISM: Artificial Sequence
<220> FEATURE:
<223> OTHER INFORMATION: synthetic polynucleotide

<400> SEQUENCE: 60
accatctgtg taaggggtaa ggggtggggg tgggtacgtc tcggcgatcg tgaaggagac 60
tgagtgag 68

<210> SEQ ID NO 61
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 61
ggattctgta tgactgtccc acgtatctca ct 32

<210> SEQ ID NO 62
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 62
ggattctgta tgactgtccc acgtatctca ct 32

<210> SEQ ID NO 63
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 63
tggatcgtga tgactgtccc gacaagaatt cgtatctcac t 41

<210> SEQ ID NO 64
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 64
tggatcgtga tgactgtccc gacaagctta cgtatctcac t 41

<210> SEQ ID NO 65
<211> LENGTH: 74
<212> TYPE: DNA
<213> ORGANISM: Artificial Sequence
<220> FEATURE:
<223> OTHER INFORMATION: synthetic polynucleotide

<400> SEQUENCE: 65
accatctgtg taaggggtaa ggggtggggg tgggtacgtc tcggcgatcg tgaaggagta 60
agctactgag tgag 74

<210> SEQ ID NO 66
<211> LENGTH: 74
<212> TYPE: DNA
<213> ORGANISM: Artificial Sequence
<220> FEATURE:
<223> OTHER INFORMATION: synthetic polynucleotide

<400> SEQUENCE: 66
accatctgtg taaggggtaa ggggtggggg tgggtacgtc tcggcgatcg tgaaggagat 60
gcatactgag tgag 74

<210> SEQ ID NO 67
<211> LENGTH: 74
<212> TYPE: DNA
<213> ORGANISM: Artificial Sequence
<220> FEATURE:
<223> OTHER INFORMATION: synthetic polynucleotide

<400> SEQUENCE: 67
attgatcact tgatttctgc ccattgatta aagtcgcaag tcggcgatcg tgaaggagta 60
agctactgag tgag 74

<210> SEQ ID NO 68
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 68
tggatcgtga tgactgtccc gacaagcata cgtatctcac t 41

<210> SEQ ID NO 69
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 69
tggatcgtga tgactgtccc gacaaatgca tgtatctcac t 41

<210> SEQ ID NO 70
<211> LENGTH: 41
<212> TYPE: DNA
<213> ORGANISM: Artificial Sequence
<220> FEATURE:

<223> OTHER INFORMATION: synthetic polynucleotide

<400> SEQUENCE: 70
tggatcgtga tgactgtccc gacaaatgca tgtatctcac t 41

<210> SEQ ID NO 71
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 71
cggcgatcgt gaaggaggct cgagtgagtg ag 32

<210> SEQ ID NO 72
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 72
cggcgatcgt gaaggaggct agcctgagtg ag 32

<210> SEQ ID NO 73
<211> LENGTH: 32
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (20)..(23)
<223> OTHER INFORMATION: n is a, c, g, or t

<400> SEQUENCE: 73
cggcgatcgt gaaggaggan nnnttgagtg ag 32

<210> SEQ ID NO 74
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 74
tggatcgtga tgactgtccc gacaagctta cgtatctcac t 41

<210> SEQ ID NO 75
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 75
tggatcgtga tgactgtccc gacaaccatg ggtatctcac t 41

<210> SEQ ID NO 76
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 76

```
tggatcgtga tgactgtccc gacaaccatg ggtatctcac t                  41


<210> SEQ ID NO 77
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 77

tggatcgtga tgactgtccc gacaaggatc cgtatctcac t                  41


<210> SEQ ID NO 78
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 78

tggatcgtga tgactgtccc gacaaggatc cgtatctcac t                  41


<210> SEQ ID NO 79
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 79

tggatcgtga tgactgtccc gacaaagtac tgtatctcac t                  41


<210> SEQ ID NO 80
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 80

tggatcgtga tgactgtccc gacaaagtac tgtatctcac t                  41


<210> SEQ ID NO 81
<211> LENGTH: 41
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (27)..(30)
<223> OTHER INFORMATION: n is a, c, g, or t

<400> SEQUENCE: 81

tggatcgtga tgactgtccc gacaatnnnn agtatctcac t                  41


<210> SEQ ID NO 82
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 82

tggatcgtga tgactgtccc                                          20
```

```
<210> SEQ ID NO 83
<211> LENGTH: 17
<212> TYPE: DNA
<213> ORGANISM: Artificial Sequence
<220> FEATURE:
<223> OTHER INFORMATION: synthetic polynucleotide

<400> SEQUENCE: 83

cggcgatcgt gaaggag                                                   17


<210> SEQ ID NO 84
<211> LENGTH: 81
<212> TYPE: DNA
<213> ORGANISM: Artificial Sequence
<220> FEATURE:
<223> OTHER INFORMATION: synthetic polynucleotide

<400> SEQUENCE: 84

aatgatacgg cgaccaccga gatctacact ctttccctac acgacgctct tccgatcttt     60

ctcgcggcga tcgtgaagga g                                              81


<210> SEQ ID NO 85
<211> LENGTH: 81
<212> TYPE: DNA
<213> ORGANISM: Artificial Sequence
<220> FEATURE:
<223> OTHER INFORMATION: synthetic polynucleotide

<400> SEQUENCE: 85

aatgatacgg cgaccaccga gatctacact ctttccctac acgacgctct tccgatcttc     60

tacccggcga tcgtgaagga g                                              81


<210> SEQ ID NO 86
<211> LENGTH: 54
<212> TYPE: DNA
<213> ORGANISM: Artificial Sequence
<220> FEATURE:
<223> OTHER INFORMATION: synthetic polynucleotide

<400> SEQUENCE: 86

caagcagaag acggcatacg agctcttccg atcttggatc gtgatgactg tccc           54


<210> SEQ ID NO 87
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 87

cggggatcgt gaaggaggct agactg                                         26


<210> SEQ ID NO 88
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 88

cggggatcgt gaaggaggct agactgag                                       28


<210> SEQ ID NO 89
<211> LENGTH: 30
```

<212> TYPE: DNA
<213> ORGANISM: Artificial Sequence
<220> FEATURE:
<223> OTHER INFORMATION: synthetic polynucleotide

<400> SEQUENCE: 89
cggggatcgt gaaggaggct agactgagtg 30

<210> SEQ ID NO 90
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 90
cggggatcgt gaaggaggct agactgagtg ag 32

<210> SEQ ID NO 91
<211> LENGTH: 45
<212> TYPE: DNA
<213> ORGANISM: Artificial Sequence
<220> FEATURE:
<223> OTHER INFORMATION: synthetic polynucleotide

<400> SEQUENCE: 91
tgagtcgtga tgactgtccc gacaagctta cgtatctcac tcagt 45

<210> SEQ ID NO 92
<211> LENGTH: 70
<212> TYPE: DNA
<213> ORGANISM: Artificial Sequence
<220> FEATURE:
<223> OTHER INFORMATION: synthetic polynucleotide

<400> SEQUENCE: 92
tgagtcgtga tgactgtccc gacaagctta cgtatctcac tcagcgggga tcgtgaagga 60
ggctagactg 70

<210> SEQ ID NO 93
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 93
tgagtcgtga tgactgtccc gacaagctta cgtatctcac tcagcgggga tcgtgaagga 60
ggctagactg ag 72

<210> SEQ ID NO 94
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 94
tggatcgtga tgactgtccc gacaagcata cgtatctcac t 41

<210> SEQ ID NO 95
<211> LENGTH: 32
<212> TYPE: DNA
<213> ORGANISM: Artificial Sequence
<220> FEATURE:

-continued

```
<223> OTHER INFORMATION: synthetic polynucleotide

<400> SEQUENCE: 95

cggcgatcgt gaaggaggct agactgagtg ag                                   32


<210> SEQ ID NO 96
<211> LENGTH: 16
<212> TYPE: DNA
<213> ORGANISM: Artificial Sequence
<220> FEATURE:
<223> OTHER INFORMATION: synthetic polynucleotide

<400> SEQUENCE: 96

gggacagtca tcacga                                                     16
```